US008540515B2

(12) United States Patent  (10) Patent No.: US 8,540,515 B2
Williams et al.  (45) Date of Patent: *Sep. 24, 2013

(54) OPTIMIZING BEHAVIORAL CHANGE BASED ON A POPULATION STATISTICAL PROFILE

(75) Inventors: Randall E. Williams, Winnetka, IL (US); Russell Fulling, Northbrook, IL (US); Timothy J. Heuer, Arlington Heights, IL (US); John Anthony Pitocco, Saint Charles, IL (US)

(73) Assignee: Pharos Innovations, LLC, Northfield, IL (US)

( * ) Notice: Subject to any disclaimer, the term of this patent is extended or adjusted under 35 U.S.C. 154(b) by 420 days.

This patent is subject to a terminal disclaimer.

(21) Appl. No.: 11/604,568

(22) Filed: Nov. 27, 2006

(65) Prior Publication Data

US 2008/0126276 A1 May 29, 2008

(51) Int. Cl.
 G09B 19/00 (2006.01)
(52) U.S. Cl.
 USPC ........... 434/236; 434/238; 600/300; 600/301; 705/2; 705/3; 705/7.11; 705/7.12; 705/7.13; 705/7.14; 705/7.15; 705/7.16; 705/7.17; 705/7.18; 705/7.19; 705/7.21; 705/7.22; 705/7.23; 705/7.24; 705/7.25; 705/7.26; 706/14
(58) Field of Classification Search
 USPC ................... 434/238, 236; 706/14; 600/300, 600/301; 705/2, 3, 7.11–7.19, 7.21–7.26
See application file for complete search history.

(56) References Cited

U.S. PATENT DOCUMENTS

| | | | |
|---|---|---|---|
| 3,986,136 A | 10/1976 | Hurlburt | |
| 4,130,881 A | 12/1978 | Haessler et al. | |
| 4,654,482 A | 3/1987 | DeAngelis | |
| 4,731,726 A | 3/1988 | Allen, III | |
| 4,766,542 A | 8/1988 | Pilarczyk | |
| 4,839,822 A | 6/1989 | Dormond et al. | |
| 4,853,854 A | 8/1989 | Behar et al. | |
| 4,984,155 A | 1/1991 | Geier et al. | |
| 5,025,374 A | 6/1991 | Roizen et al. | |
| 5,036,462 A | 7/1991 | Kaufman et al. | |

(Continued)

FOREIGN PATENT DOCUMENTS

| | | |
|---|---|---|
| DE | 44 30 164 A1 | 2/1996 |
| EP | 0 214 347 A1 | 3/1987 |

(Continued)

OTHER PUBLICATIONS

The prosecution history of U.S. Appl. No. 11/604,569, printed Mar. 4, 2009, including a listing for an issued Office Action.

(Continued)

*Primary Examiner* — Jack Yip
(74) *Attorney, Agent, or Firm* — Lempia Summerfield Katz LLC

(57) ABSTRACT

A system for directing behavior of a first patient of a plurality of patients towards a behavioral objective includes a patient behavioral path calculator, a patient goal calculator, and a patient monitoring processor. The system also includes an information communication processor and a statistical processor. The patient behavioral path calculator calculates a patient behavioral path based on a statistical profile. The patient goal calculator calculates patient goals along the patient behavioral path toward a behavioral objective. The statistical processor can modify the statistical profile based on a response to a targeted message sent by the information communication processor.

34 Claims, 55 Drawing Sheets

(56) References Cited

U.S. PATENT DOCUMENTS

| | | | |
|---|---|---|---|
| 5,047,614 A | 9/1991 | Bianco | |
| 5,084,819 A | 1/1992 | Dewey et al. | |
| 5,207,580 A | 5/1993 | Strecher | |
| 5,255,305 A | 10/1993 | Sattar | |
| RE34,587 E | 4/1994 | Crane et al. | |
| 5,307,263 A | 4/1994 | Brown | |
| 5,339,821 A | 8/1994 | Fujimoto | |
| 5,357,596 A | 10/1994 | Takebayashi et al. | |
| 5,369,699 A | 11/1994 | Page et al. | |
| 5,390,238 A | 2/1995 | Kirk et al. | |
| 5,435,324 A * | 7/1995 | Brill | 128/897 |
| 5,459,306 A | 10/1995 | Stein et al. | |
| 5,465,291 A | 11/1995 | Barrus et al. | |
| 5,471,382 A | 11/1995 | Tallman et al. | |
| 5,474,090 A | 12/1995 | Begun et al. | |
| 5,569,212 A | 10/1996 | Brown | |
| 5,596,994 A | 1/1997 | Bro | |
| 5,601,435 A | 2/1997 | Quy | |
| 5,628,309 A | 5/1997 | Brown | |
| 5,633,910 A | 5/1997 | Cohen | |
| 5,660,176 A | 8/1997 | Iliff | |
| 5,664,110 A | 9/1997 | Green et al. | |
| 5,678,571 A | 10/1997 | Brown | |
| 5,682,525 A | 10/1997 | Bouve et al. | |
| 5,704,922 A | 1/1998 | Brown | |
| 5,711,297 A | 1/1998 | Iliff | |
| 5,720,733 A | 2/1998 | Brown | |
| 5,722,418 A | 3/1998 | Bro | |
| 5,724,968 A | 3/1998 | Iliff | |
| 5,730,654 A | 3/1998 | Brown | |
| 5,764,923 A | 6/1998 | Tallman et al. | |
| 5,782,814 A | 7/1998 | Brown et al. | |
| 5,792,117 A | 8/1998 | Brown | |
| 5,794,219 A | 8/1998 | Brown | |
| 5,812,776 A | 9/1998 | Gifford | |
| 5,821,512 A | 10/1998 | O'Hagan et al. | |
| 5,821,513 A | 10/1998 | O'Hagan et al. | |
| 5,822,715 A | 10/1998 | Worthington et al. | |
| 5,827,180 A | 10/1998 | Goodman | |
| 5,828,943 A | 10/1998 | Brown | |
| 5,832,448 A | 11/1998 | Brown | |
| 5,848,413 A | 12/1998 | Wolff | |
| 5,868,669 A | 2/1999 | Iliff | |
| 5,879,163 A | 3/1999 | Brown et al. | |
| 5,887,133 A | 3/1999 | Brown et al. | |
| 5,894,119 A | 4/1999 | Tognazzini | |
| 5,897,493 A | 4/1999 | Brown | |
| 5,899,855 A | 5/1999 | Brown | |
| 5,902,234 A | 5/1999 | Webb | |
| 5,908,301 A | 6/1999 | Lutz | |
| 5,908,383 A | 6/1999 | Brynjestad | |
| 5,910,107 A | 6/1999 | Iliff | |
| 5,913,310 A | 6/1999 | Brown | |
| 5,918,603 A | 7/1999 | Brown | |
| 5,933,136 A | 8/1999 | Brown | |
| 5,933,829 A | 8/1999 | Durst et al. | |
| 5,935,060 A | 8/1999 | Iliff | |
| 5,938,726 A | 8/1999 | Reber et al. | |
| 5,940,801 A | 8/1999 | Brown | |
| 5,951,300 A | 9/1999 | Brown | |
| 5,956,501 A | 9/1999 | Brown | |
| 5,960,403 A | 9/1999 | Brown | |
| 5,964,700 A | 10/1999 | Tallman et al. | |
| 5,967,789 A | 10/1999 | Segel et al. | |
| 5,978,773 A | 11/1999 | Hudetz et al. | |
| 5,985,559 A | 11/1999 | Brown | |
| 5,986,651 A | 11/1999 | Reber et al. | |
| 5,987,519 A | 11/1999 | Peifer et al. | |
| 5,995,105 A | 11/1999 | Reber et al. | |
| 5,997,476 A | 12/1999 | Brown | |
| 6,014,626 A | 1/2000 | Cohen | |
| 6,023,686 A | 2/2000 | Brown | |
| 6,024,699 A | 2/2000 | Surwit et al. | |
| 6,032,119 A | 2/2000 | Brown et al. | |
| 6,039,688 A | 3/2000 | Douglas et al. | |
| 6,053,866 A | 4/2000 | McLeod | |
| 6,055,506 A | 4/2000 | Frasca, Jr. | |
| 6,063,028 A * | 5/2000 | Luciano | 600/300 |
| 6,068,615 A | 5/2000 | Brown et al. | |
| 6,071,236 A | 6/2000 | Iliff | |
| 6,080,106 A | 6/2000 | Lloyd et al. | |
| 6,083,173 A | 7/2000 | Grant et al. | |
| 6,097,927 A | 8/2000 | LaDue | |
| 6,101,478 A | 8/2000 | Brown | |
| 6,102,862 A | 8/2000 | Grunwald et al. | |
| 6,108,656 A | 8/2000 | Durst et al. | |
| 6,108,665 A * | 8/2000 | Bair et al. | 1/1 |
| 6,110,148 A | 8/2000 | Brown et al. | |
| 6,113,578 A | 9/2000 | Brown | |
| 6,120,440 A * | 9/2000 | Goknar | 600/300 |
| 6,123,259 A | 9/2000 | Ogasawara | |
| 6,126,596 A | 10/2000 | Freedman | |
| 6,134,548 A | 10/2000 | Gottsman et al. | |
| 6,144,837 A | 11/2000 | Quy | |
| 6,144,848 A | 11/2000 | Walsh et al. | |
| 6,149,585 A | 11/2000 | Gray | |
| 6,151,586 A | 11/2000 | Brown | |
| 6,161,095 A | 12/2000 | Brown | |
| 6,167,362 A | 12/2000 | Brown et al. | |
| 6,167,386 A | 12/2000 | Brown | |
| 6,168,563 B1 | 1/2001 | Brown | |
| 6,177,940 B1 | 1/2001 | Bond et al. | |
| 6,186,145 B1 | 2/2001 | Brown | |
| 6,190,313 B1 | 2/2001 | Hinkle | |
| D439,242 S | 3/2001 | Brown et al. | |
| 6,196,970 B1 | 3/2001 | Brown | |
| 6,199,048 B1 | 3/2001 | Hudetz et al. | |
| 6,210,272 B1 | 4/2001 | Brown | |
| 6,233,539 B1 | 5/2001 | Brown | |
| 6,234,964 B1 | 5/2001 | Iliff | |
| 6,240,393 B1 | 5/2001 | Brown | |
| 6,246,992 B1 | 6/2001 | Brown | |
| 6,248,065 B1 | 6/2001 | Brown | |
| 6,259,889 B1 | 7/2001 | LaDue | |
| 6,260,022 B1 | 7/2001 | Brown | |
| 6,261,230 B1 | 7/2001 | Bardy | |
| 6,270,455 B1 | 8/2001 | Brown | |
| 6,317,731 B1 * | 11/2001 | Luciano | 706/21 |
| 6,330,426 B2 | 12/2001 | Brown et al. | |
| 6,334,778 B1 | 1/2002 | Brown | |
| 6,338,039 B1 * | 1/2002 | Lonski et al. | 705/3 |
| 6,338,628 B1 | 1/2002 | Smith | |
| 6,352,523 B1 | 3/2002 | Brown et al. | |
| 6,366,871 B1 | 4/2002 | Geva | |
| 6,368,273 B1 | 4/2002 | Brown | |
| 6,375,469 B1 | 4/2002 | Brown | |
| 6,379,301 B1 | 4/2002 | Worthington et al. | |
| 6,381,577 B1 | 4/2002 | Brown | |
| 6,409,662 B1 | 6/2002 | Lloyd et al. | |
| 6,468,210 B1 | 10/2002 | Iliff | |
| 6,478,737 B2 | 11/2002 | Bardy | |
| 6,482,156 B2 | 11/2002 | Iliff | |
| 6,524,241 B2 | 2/2003 | Iliff | |
| 6,551,266 B1 * | 4/2003 | Davis, Jr. | 604/6.09 |
| 6,553,386 B1 | 4/2003 | Alabaster | |
| 6,569,093 B2 | 5/2003 | Iliff | |
| 6,607,482 B1 | 8/2003 | Teitelbaum | |
| 6,609,068 B2 | 8/2003 | Cranley et al. | |
| 6,641,532 B2 | 11/2003 | Iliff | |
| 6,687,685 B1 | 2/2004 | Sadeghi et al. | |
| 6,723,046 B2 | 4/2004 | Lichtenstein et al. | |
| 6,725,209 B1 | 4/2004 | Iliff | |
| 6,769,915 B2 | 8/2004 | Murgia et al. | |
| 6,816,807 B2 | 11/2004 | Kriger | |
| 6,879,163 B2 | 4/2005 | Örmin | |
| 6,974,328 B2 * | 12/2005 | Aspe et al. | 434/262 |
| 7,077,806 B2 * | 7/2006 | Ackermann et al. | 600/300 |
| 7,206,632 B2 * | 4/2007 | King | 600/544 |
| 7,297,108 B2 * | 11/2007 | Iliff | 600/300 |
| 7,367,956 B2 * | 5/2008 | King | 600/554 |
| 7,725,842 B2 * | 5/2010 | Bronkema | 715/866 |
| 7,765,113 B2 * | 7/2010 | Ware et al. | 705/3 |
| 7,787,946 B2 * | 8/2010 | Stahmann et al. | 607/3 |
| 2001/0000810 A1 * | 5/2001 | Alabaster | 707/104 |

| | | |
|---|---|---|
| 2001/0011224 A1 | 8/2001 | Brown |
| 2001/0023419 A1* | 9/2001 | Lapointe et al. ............... 706/15 |
| 2001/0025246 A1 | 9/2001 | Haines et al. |
| 2001/0047252 A1 | 11/2001 | Brown |
| 2001/0053875 A1 | 12/2001 | Iliff |
| 2002/0002325 A1 | 1/2002 | Iliff |
| 2002/0016529 A1 | 2/2002 | Iliff |
| 2002/0019747 A1* | 2/2002 | Ware et al. ....................... 705/2 |
| 2002/0029157 A1 | 3/2002 | Marchosky |
| 2002/0050538 A1 | 5/2002 | Fabio |
| 2002/0052540 A1 | 5/2002 | Iliff |
| 2002/0052562 A1 | 5/2002 | Lipman |
| 2002/0065758 A1* | 5/2002 | Henley ........................... 705/37 |
| 2002/0099275 A1 | 7/2002 | Schmidt et al. |
| 2002/0111539 A1 | 8/2002 | Cosentino et al. |
| 2002/0115913 A1 | 8/2002 | Christ et al. |
| 2002/0128992 A1* | 9/2002 | Alabaster .......................... 707/1 |
| 2002/0133377 A1 | 9/2002 | Brown |
| 2002/0133502 A1 | 9/2002 | Rosenthal et al. |
| 2003/0045782 A1 | 3/2003 | Iliff |
| 2003/0050538 A1 | 3/2003 | Naghavi et al. |
| 2003/0092972 A1 | 5/2003 | Mantilla et al. |
| 2003/0092976 A1 | 5/2003 | Murase et al. |
| 2003/0097279 A1 | 5/2003 | deLusignan et al. |
| 2003/0127390 A1* | 7/2003 | Davis, Jr. ...................... 210/646 |
| 2003/0135095 A1 | 7/2003 | Iliff |
| 2003/0163351 A1 | 8/2003 | Brown et al. |
| 2003/0182163 A1 | 9/2003 | Tice et al. |
| 2003/0186202 A1 | 10/2003 | Isenberg |
| 2003/0199740 A1 | 10/2003 | Iliff |
| 2003/0212579 A1 | 11/2003 | Brown et al. |
| 2003/0229513 A1* | 12/2003 | Spertus ............................. 705/2 |
| 2003/0229514 A2 | 12/2003 | Brown |
| 2004/0015337 A1* | 1/2004 | Thomas et al. ................. 703/11 |
| 2004/0016437 A1 | 1/2004 | Cobb et al. |
| 2004/0018476 A1 | 1/2004 | LaDue |
| 2004/0034286 A1 | 2/2004 | Kasper et al. |
| 2004/0034289 A1 | 2/2004 | Teller et al. |
| 2004/0044545 A1 | 3/2004 | Wiesmann et al. |
| 2004/0059196 A1 | 3/2004 | Abraham-Fuchs et al. |
| 2004/0059200 A1 | 3/2004 | Iliff |
| 2004/0059599 A1 | 3/2004 | McIvor |
| 2004/0106855 A1 | 6/2004 | Brown |
| 2004/0107116 A1 | 6/2004 | Brown |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0177053 A1 | 9/2004 | Donoho et al. |
| 2004/0181433 A1 | 9/2004 | Blair |
| 2004/0210117 A1 | 10/2004 | Ueno et al. |
| 2004/0221855 A1 | 11/2004 | Ashton |
| 2004/0230549 A1 | 11/2004 | Freer et al. |
| 2004/0247748 A1* | 12/2004 | Bronkema ..................... 426/106 |
| 2004/0267565 A1 | 12/2004 | Grube |
| 2005/0021240 A1* | 1/2005 | Berlin et al. ..................... 702/20 |
| 2005/0043965 A1* | 2/2005 | Heller et al. ....................... 705/2 |
| 2005/0058970 A1 | 3/2005 | Perlman et al. |
| 2005/0059895 A1 | 3/2005 | Brown |
| 2005/0060194 A1 | 3/2005 | Brown |
| 2005/0075669 A1* | 4/2005 | King ................................. 607/2 |
| 2005/0080462 A1* | 4/2005 | Jenkins et al. ................... 607/58 |
| 2005/0080652 A1 | 4/2005 | Brown |
| 2005/0086083 A1 | 4/2005 | Brown |
| 2005/0113649 A1 | 5/2005 | Bergantino |
| 2005/0113650 A1 | 5/2005 | Pacione et al. |
| 2005/0115561 A1* | 6/2005 | Stahmann et al. ........ 128/200.24 |
| 2005/0198095 A1 | 9/2005 | Du et al. |
| 2005/0203773 A1* | 9/2005 | Soto et al. ......................... 705/2 |
| 2005/0240434 A1* | 10/2005 | Wooten et al. .................... 705/2 |
| 2005/0240444 A1 | 10/2005 | Wooten et al. |
| 2005/0246185 A1 | 11/2005 | Brown |
| 2006/0004603 A1 | 1/2006 | Peterka et al. |
| 2006/0004611 A1 | 1/2006 | Brown |
| 2006/0019225 A1 | 1/2006 | Orman et al. |
| 2006/0024654 A1 | 2/2006 | Goodkovsky |
| 2006/0074708 A1* | 4/2006 | Woods .............................. 705/2 |
| 2006/0085223 A1* | 4/2006 | Anderson et al. ................. 705/2 |
| 2006/0136142 A1* | 6/2006 | Berlin et al. ..................... 702/20 |
| 2006/0161850 A1 | 7/2006 | Seaberg |
| 2006/0205564 A1* | 9/2006 | Peterson ........................... 482/8 |
| 2006/0252600 A1* | 11/2006 | Grogan et al. .................... 482/8 |
| 2006/0270944 A1* | 11/2006 | King ............................. 600/554 |
| 2006/0271405 A1* | 11/2006 | Cipolle et al. .................... 705/3 |
| 2007/0072156 A1* | 3/2007 | Kaufman et al. ............. 434/236 |

FOREIGN PATENT DOCUMENTS

| | | |
|---|---|---|
| JP | 58-37765 A | 3/1983 |
| JP | 2000-148889 A | 5/2000 |
| WO | WO 95/21419 A1 | 8/1995 |
| WO | WO 96/18260 A1 | 6/1996 |
| WO | WO 98/02836 A2 | 1/1998 |
| WO | WO 00/75748 A2 | 12/2000 |
| WO | WO 01/33314 A2 | 5/2001 |
| WO | WO 02/054947 A2 | 7/2002 |
| WO | WO 03/044629 A2 | 5/2003 |
| WO | WO 2007/005622 A2 | 1/2007 |

OTHER PUBLICATIONS

The prosecution history of U.S. Appl. No. 11/604,570, printed Mar. 4, 2009.

Adomeit, Alin et al., "A new model for disease management", *McKinsey Quarterly*, No. 4, 2001, pp. 92-101.

Agency for Health Care Policy & Research, "AHCPR to Demonstrate Use of Computerized Decision-Support Software in Clinical Practice", obtained at internet address <http://www.hhs.gov/news/press/1996pres/961218.html> on Jan. 3, 2007, dated Dec. 18, 1996, 3 pages.

Arbogast, James G. et al., "Home Diabetes Monitoring Through Touch-Tone Computer Data Entry and Voice Synthesizer Response", *Proceedings of the 8th Annual Symposium on Computer Applications in Medical Care*, 1984, pp. 841-844.

Bell, M.D., Douglas S. et al., "Health Status Assessment via the World Wide Web", *Proceedings of the AMIA Annual Fall Symposium*, Philadelphia: Hanley & Belfus, 1996, pp. 338-342.

British Columbia Institute of Technology, "Home Monitoring Technologies in the Community/Home Care Environment", Mar. 2006, 62 pages.

California Health Care Foundation, "E-Disease Management", prepared by First Consulting Group, Nov. 2001, 50 pages.

California Health Care Foundation, "Patient Self-Management Tools: An Overview", prepared by Critical Mass Consulting, Jun. 2005, 25 pages.

Clayton, Richard L. et al., "Using E-Mail/World Wide Web for Establishment Survey Data Collection", *Proceedings of the Section on Survey Research Methods, American Statistical Association*, and Abstract, 1995, 6 pages.

Dintruff, Diane L. et al., "Evaluation of Speech Technology in Mental Health Assessment", *Speech Technology*, Mar./Apr. 1987, pp. 32-38.

Fitzmaurice, PhD, J. Michael et al., "Three Decades of Research on Computer Applications in Health Care: Medical Informatics Support at the Agency of Healthcare Research and Quality", *Journal of the American Medical Informatics Association*, vol. 9, No. 2, Mar./Apr. 2002, pp. 144-160.

Gómez, E. J. et al., "Telemedicine for diabetes care: the DIABTel approach towards diabetes telecare", *Med. Inform.* (1996), vol. 21, No. 4, 1996, pp. 283-295.

IBM, "Simultaneous Use of Dual Tone Multi-Frequency and Voice Recognition in Voice Response Unit Applications", *IBM Technical Disclosure Bulletin*, vol. 39, No. 3, Mar. 1996, pp. 31-32.

Khan, Charles, "Announcing: Rand-36 Health Survey", Google Group Chat Page, sci.med, obtained from a google internet address, Jul. 1995, 2 pages.

Kim, Michelle Y., "A Multimedia Information System for Home Health-Care Support", *IEEE Multimedia*, Winter 1995, pp. 83-87.

Langen, Pauline, "The Benefits of Integrating Voice Technology and Artificial Intelligence to Home Health Monitoring Services", *Group Health Institute Proceedings*, Jun. 8, 1992, pp. 139-145.

Lenert, MD, MS, Leslie et al., "Design and Pilot Evaluation of an Internet Smoking Cessation Program", *Journal of the American Medical Informatics Association*, vol. 10, No. 1, Jan./Feb. 2003, pp. 16-20.

Liang, Huigang et al., "Web-based intervention support system for health promotion", *Decision Support Systems*, 42, 2006, pp. 435-449.

Lindberg, Christopher C. S., "Implementation of In-home Telemedicine in Rural Kansas: Answering an Elderly Patient's Needs", *Journal of the American Medical Informatics Association*, vol. 4, No. 1, Jan./Feb. 1997, pp. 14-17.

Marshall, M.D., Barry J. et al., "The Automatic Patient Symptom Monitor (APSM): A Voice Mail System for Clinical Research", *Proceedings of the 17th Annual Symposium on Computer Applications in Medical Care*, Conference Date: Oct. 30-Nov. 3, 1993, Proceedings Published: 1994, pp. 32-36.

Medical College of Wisconsin, "About the SF-36", *Medical College of Wisconsin*, obtained at internet address <http://www.mcw.edu/midas/health/SF-36.html> on Mar. 5, 2007, 5 pages.

Nigrin, M.D., Daniel J. et al., "Glucoweb: A Case Study of Secure, Remote Biomonitoring and Communication", *Proceedings of the AMIA Symposium*, Nov. 4-8, 2000, 5 pages.

Patel, Umesh et al., "A Computer-Based, Automated, Telephonic System to Monitor Patient Progress in the Home Setting", *Journal of Medical Systems*, vol. 16, Nos. 2/3, 1992, pp. 101-112.

Pollack, Martha E., "Intelligent Technology for an Aging Population: The Use of AI to Assist Elders with Cognitive Impairment", *AI Magazine*, Summer 2005, pp. 9-24.

Prochaska, James O. et al., "Stage-based expert systems to guide a population of primary care patients to quit smoking, eat healthier, prevent skin cancer, and receive regular mammograms", *Preventive Medicine*, 41, 2005, pp. 406-416.

Ramelson, Harley Z. et al., "An automated telephone-based smoking cessation education and counseling system", *Patient Education and Counseling*, 36, 1999, pp. 131-144.

Reiter, Ehud et al., "Lessons from a failure: Generating tailored smoking cessation letters", *Artificial Intelligence*, 144, 2003, pp. 41-58.

Revere, MA, Mlis, Debra et al., "Review of Computer-generated Outpatient Health Behavior Interventions: Clinical Encounters 'In Absentia'", *Journal of the American Medical Informatics Association*, vol. 8, No. 1, Jan./Feb. 2001, pp. 62-79.

Riva, Alberto, "A Web-Based Architecture for the Intelligent Management of Chronic Patients", *Proceedings of the AMIA Annual Fall Symposium*, Philadelphia: Hanley & Belfus, 1996, 6 pages.

Riva, Alberto et al., "Distributed AI Technologies for Patient Management", *Proceedings of the AMIA Annual Fall Symposium*, Philadelphia: Hanley & Belfus, 1996, 5 pages.

Riva, Alberto et al., "A Web-based System for the Intelligent Management of Diabetic Patients", *M.D. Computing*, 14(5), Nov. 1997, pp. 364-364 (12 pages).

Schwartz, M.D., Marc D., "Network: Using the Ordinary Telephone as a Computer Terminal for Professional or Research Offices", *Computers in Psychiatry/Psychology*, vol. 8, No. 3, Fall 1986, 3 pages.

Shimoda, Todd, "An Interactive Software-Agent Smoking Cessation Program", *Proceedings of the 36th Hawaii International Conference on System Sciences*, 2003, 9 pages.

Siegel, Karolynn et al., "Computerized Telephone Assessment of the 'Concrete' Needs of Chemotherapy Outpatients: A Feasibility Study", *Journal of Clinical Oncology*, vol. 6, No. 11, Nov. 1988, pp. 1760-1767.

Silverman, Barry G. et al., "Web-Based Health Care Guideline Agents: The Case of Reminders of ToDos-II(R2Do2)", George Washington University, Feb. 1997, 40 pages.

Smith, Mary Beth et al., "The Voice-Based Telephone-Linked Computer System", *MUG Quarterly*, vol. XVIII, No. 1, pp. 54-61.

Suh, Sang C. et al., "Intelligent Medical Patient Interviewer", *Proceedings of the ISCA International Conference*, 1995, pp. 249-252.

Szolovits, Peter et al., "Guardian Angel: Patient-Centered Health Information Systems", Massachusetts Institute of Technology, May 1994, 39 pages.

Terziyan, Vagan et al., "The decision support system for telemedicine based on multiple expertise", *International Journal of Medical Informatics*, 49, 1998, pp. 217-229.

Tetzlaff, Linda et al., "Home Health Care Support", *The First Society in Computing*, obtained at internet address <http://www1.acm.org/sigchi/chi95/proceedings/demos/1st_bdy.htm> on Oct. 4, 2006, 3 pages.

Velicer, Wayne F. et al., "An expert system intervention for smoking cessation", *Patient Education and Counseling*, 36, 1999, pp. 119-129.

Wang, M.P.H., Jen et al., "Administering an effective health intervention for smoking cessation online: the international users of StopTabac", *Preventive Medicine*, 39, 2004, pp. 962-968.

Written Opinion in International Application No. PCT/US 07/85491, dated Jun. 5, 2008, 8 pages.

International Search Report in International Application No. PCT/US 07/85491, dated Jun. 5, 2008, 2 pages.

International Search Report and Written Opinion in International Application No. PCT/US07/85334 dated Nov. 3, 2008, 9 pages.

International Preliminary Report on Patentability mailed Jun. 3, 2009, in PCT App. No. PCT/US2007/085334, 7 pages.

Non-Final Office Action mailed Mar. 5, 2009, in copending U.S. Appl. No. 11/604,570, 6 pages.

Non-Final Office Action mailed Apr. 23, 2009, in copending U.S. Appl. No. 11/604,570, 19 pages.

International Preliminary Report on Patentability issued Jun. 3, 2009, in PCT App. No. PCT/US2007/085106, 8 pages.

International Preliminary Report on Patentability issued Jun. 11, 2009, in PCT App. No. PCT/US2007/085491, 8 pages.

\* cited by examiner

Pharos Innovations CHF Tel-Assurance Patient Support
Monthly Summary Report For June 2006

| | | | |
|---|---|---|---|
| Patient | Wanda, Wanda | | |
| Telephone | Home: 630-303-3039 | DOB | 1/1/1953 |
| Physician | Boone, Daniel | Start Of Care | 8/8/2005 |
| Clinical Weights | | Min Weight | 188 lbs |
| Best Weight | 190 lbs | Max Weight | 194 lbs |

No Data Available

No Graph Available

Printed 7/19/2006   Tel-Assurance is a trademark licensed to Pharos Innovations

Pharos Innovations CHF Tel-Assurance Patient Support
Monthly Summary Report For June 2006

| | | | |
|---|---|---|---|
| Patient | Wyman, Jane | | |
| Telephone | Home: (555)555-1212 | DOB | 6/19/1935 |
| Physician | Davidson, Donell<br>Fax: 515-323-4446 | Start Of Care | 9/22/2003 |
| Clinical Weights | 2/23/2005 | Min Weight | 167 lbs |
| Best Weight | 172 lbs | Max Weight | 175 lbs |

| Survey Date | Status | Weight | SOB | Edema | PND | Orthopnea | Lightheaded | Fatigue |
|---|---|---|---|---|---|---|---|---|
| 06/01/2006 | Active | 168 | No | No | No | No | No | No |
| 06/02/2006 | Active | - | - | - | - | - | - | - |
| 06/03/2006 | Active | 165 | No | No | No | No | No | No |
| 06/04/2006 | Active | 167 | No | No | No | No | No | No |
| 06/05/2006 | Active | 170 | No | No | No | No | No | No |
| 06/06/2006 | Active | 168 | No | No | No | No | No | No |
| 06/07/2006 | Active | 170 | No | No | No | No | No | No |
| 06/08/2006 | Active | 169 | No | No | No | No | No | No |
| 06/09/2006 | Active | 166 | No | No | No | No | No | No |
| 06/10/2006 | Active | 166 | No | No | No | No | No | No |
| 06/11/2006 | Active | 170 | No | Yes | No | No | No | No |
| 06/12/2006 | Active | 171 | Yes | Yes | No | No | No | Yes |
| 06/13/2006 | Active | 171 | Yes | Yes | No | Yes | No | Yes |
| 06/14/2006 | Active | 170 | Yes | Yes | No | Yes | No | No |
| 06/15/2006 | Active | 169 | No | No | No | Yes | No | Yes |
| 06/16/2006 | Active | 168 | No | No | No | No | No | No |
| 06/17/2006 | Active | 168 | No | No | No | No | No | No |
| 06/18/2006 | Active | 168 | No | No | No | No | No | No |
| 06/19/2006 | Active | 168 | No | No | No | No | No | No |
| 06/20/2006 | Active | 168 | No | No | No | No | No | No |
| 06/21/2006 | Active | 168 | No | No | No | No | No | No |
| 06/22/2006 | Active | 168 | No | No | No | No | No | No |
| 06/23/2006 | Active | 168 | No | No | No | No | No | No |
| 06/24/2006 | Active | 170 | No | No | No | Yes | No | No |
| 06/25/2006 | Active | 169 | No | No | No | Yes | No | No |
| 06/26/2006 | Active | 168 | No | No | No | No | No | No |
| 06/27/2006 | Active | 168 | No | No | No | No | No | No |
| 06/28/2006 | Active | 168 | No | No | No | No | No | No |
| 06/29/2006 | Active | 168 | No | No | No | No | No | No |
| 06/30/2006 | Active | 168 | No | No | No | No | No | No |

Monthly Weight Trend

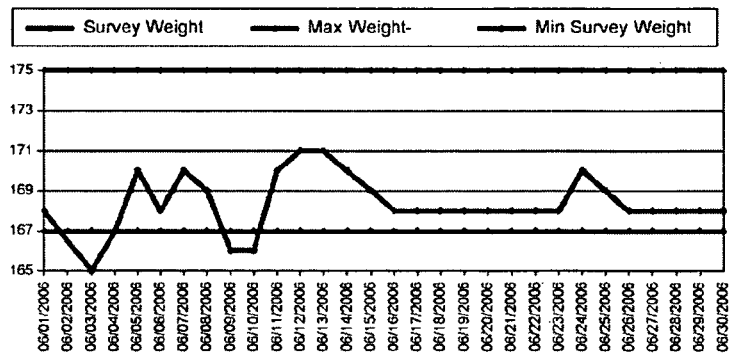

Printed 7/19/2006    Tel-Assurance is a trademark licensed to Pharos Innovations

FIG. 54

OPTIMIZING BEHAVIORAL CHANGE BASED ON A POPULATION STATISTICAL PROFILE

REFERENCE TO RELATED APPLICATIONS

The following co-pending and commonly assigned U.S. Patent Applications have been filed on the same date as the present application: U.S. patent application Ser. No. 11/604,570, "Calculating a Behavioral Path Based on a Statistical Profile", filed herewith and U.S. patent application Ser. No. 11/604,569, "Optimizing Behavioral Change Based on a Patient Statistical Profile", filed herewith.

These applications relate to and further describes other aspects of the embodiments disclosed in the present application and are herein incorporated by reference.

BACKGROUND

Behavior monitoring and altering systems focus on encouraging a particular patient behavior, whether that behavior is to stop an unhealthy activity, such as smoking, or whether that behavior is to encourage a healthy activity, such as exercising, dieting, adhering to a prescribed medical treatment regimen or maintaining a regular scheduled intake of medication, e.g. insulin. These systems often focus on an individual and that individual's behavior, resulting in a regimen of behavior tailored for that particular person.

However, in the context of chronic disease management, as more and more people are recovering outside the purview of human interaction, there is an increased risk that a prescribed regimen will be ignored. As today's lifestyle has become increasingly busier and fast-paced, there remains very little time for an individual clinician to ensure that a particular recommended regimen is followed by his or her patients. Furthermore, there is no guarantee that two people with similar conditions will respond to a monitoring system, and its accompanying recommendations, in exactly the same way. For example, in the case of two individuals who wish to stop smoking, many individual-specific variables will determine the likelihood of success that either individual has to actually achieve the goal of stopping smoking, such as their lifestyle or their availability to the monitoring system, such as their accessibility to a communication medium for reporting back to the monitoring system. Additionally, there is no guarantee that either individual will be more successful than the other at stopping a smoking behavior.

Many behavior monitoring and altering systems are established solely around a pre-determined behavioral regimen and do not evolve according to the individual's needs. Other than through institutional changes, these behavior monitoring and altering systems do not take into account that individual's behavior or whether other similarly situated individuals have been successful at a particular behavioral change.

Therefore, a need exists for a behavior monitoring and altering system that not only evolves according to an individual's behavior and responses, but also takes into account the likelihood of success of that individual achieving his or her desired goal as compared with other similarly situated individuals and encourages that individual into achieving his or her desired goal.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 27-54 depict examples of individual monthly reports generated by one embodiment of the disclosed patient monitoring system.

DETAILED DESCRIPTION

Figure 1:
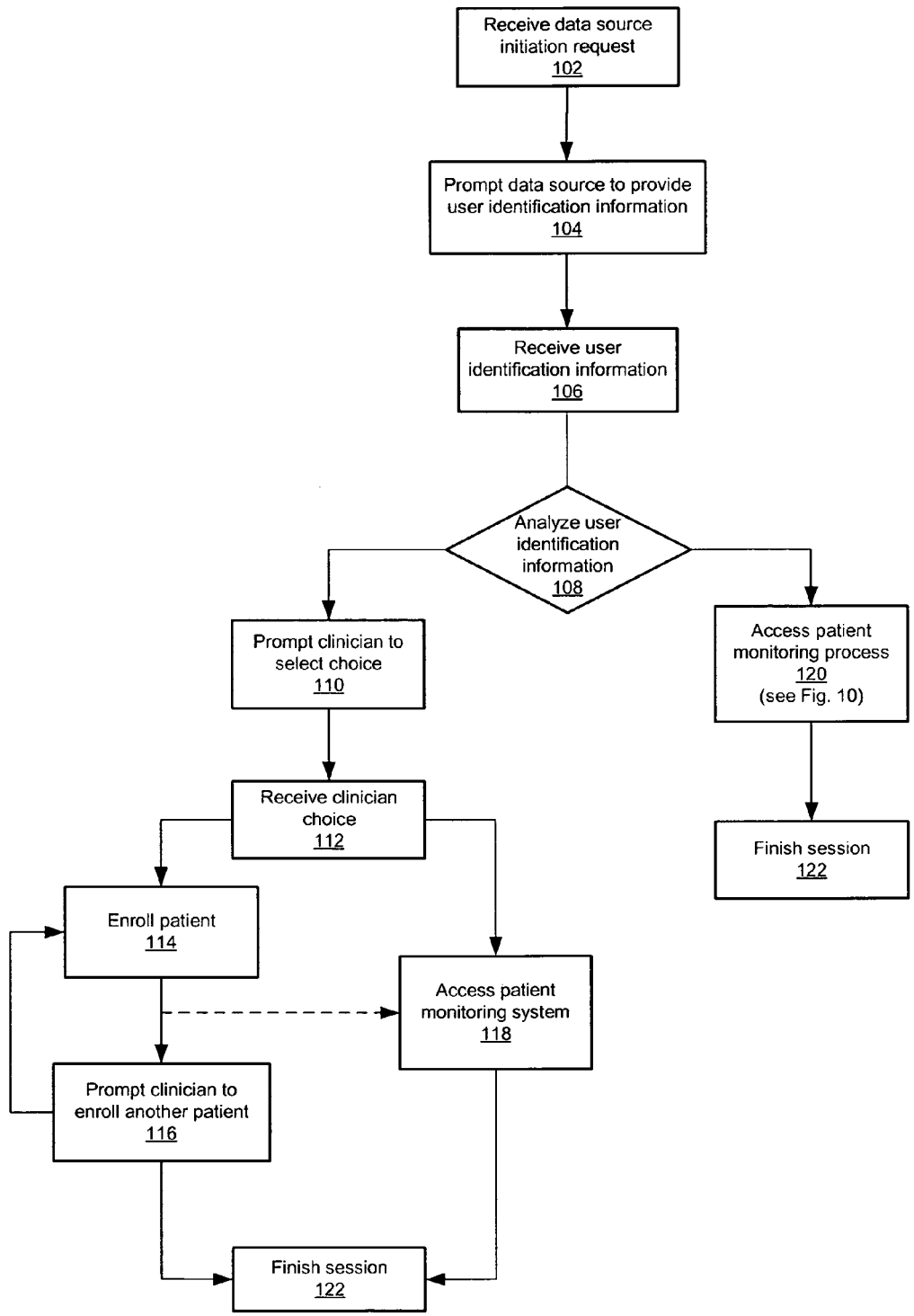
FIG. 1 is a flowchart of one embodiment of accessing a patient enrollment and monitoring system.

The patient monitoring system disclosed herein is directed to implementing methods of statistical process control in helping patients achieve a desired behavioral objective and/or outcome. In general, statistical process control ("SPC"), is a method for measuring, understanding and controlling variation in a process. SPC has many aspects, from control charting to process capability studies and improvement. SPC may be categorized into four basic steps: 1) measuring the process; 2) eliminating variances within the process to make it consistent; 3) monitoring the process; and 4) improving the process. This four-step cycle may be employed over and over again for continuous improvement.

SPC is used in the disclosed patient monitoring system to help patients achieve a desired behavioral objective and/or outcome by monitoring current patient responses to surveys based on and refining the process used to encourage the current patient and/or other patients to achieve that desired behavioral objective and/or outcome. For example, the patient monitoring system may use a statistical profile of a patient-population to generate goals, objectives, and fault limits for an individual patient. A patient-population may be a set of patients similarly situated based on specified criteria, such as demographics, medical condition(s), symptom(s), medicinal prescriptions, prior treatments currently being administered or previously received, economic data, or other specified criteria or combinations thereof.

Based on the generated goals, objectives and/or fault limits, the patient monitoring system prepares one or more targeted messages or surveys to be delivered to a patient to help the patient achieve the goals and/or objectives. By monitoring the patient's response to the one or more targeted messages and/or surveys, the patient monitoring system refines the statistical profile of the patient-population to re-calculate the goals, objectives, and fault limits for the patient, other future patients, or a combination thereof. The patient monitoring system can further, or alternatively, use the refined or redefined statistical profile of the group of patients to help future patients achieve similar goals and/or objectives. Thus, by using statistical process control, the patient monitoring system can help current and/or future patients maximize their ability to achieve a desired goal and/or objective.

The embodiments herein relate to a system and method for directing and encouraging behavior of a first patient of a plurality of patients towards a behavioral objective. The system includes a patient behavioral path calculator, a patient goal calculator, and a patient monitoring processor. The system also includes an information communication processor and a statistical processor. The patient behavioral path calculator calculates a patient behavioral path based on a statistical profile. The patient goal calculator calculates patient goals along the patient behavioral path toward a behavioral objective. The statistical processor can modify the statistical profile based on a response to a targeted message sent by the information communication processor.

Figure 21:
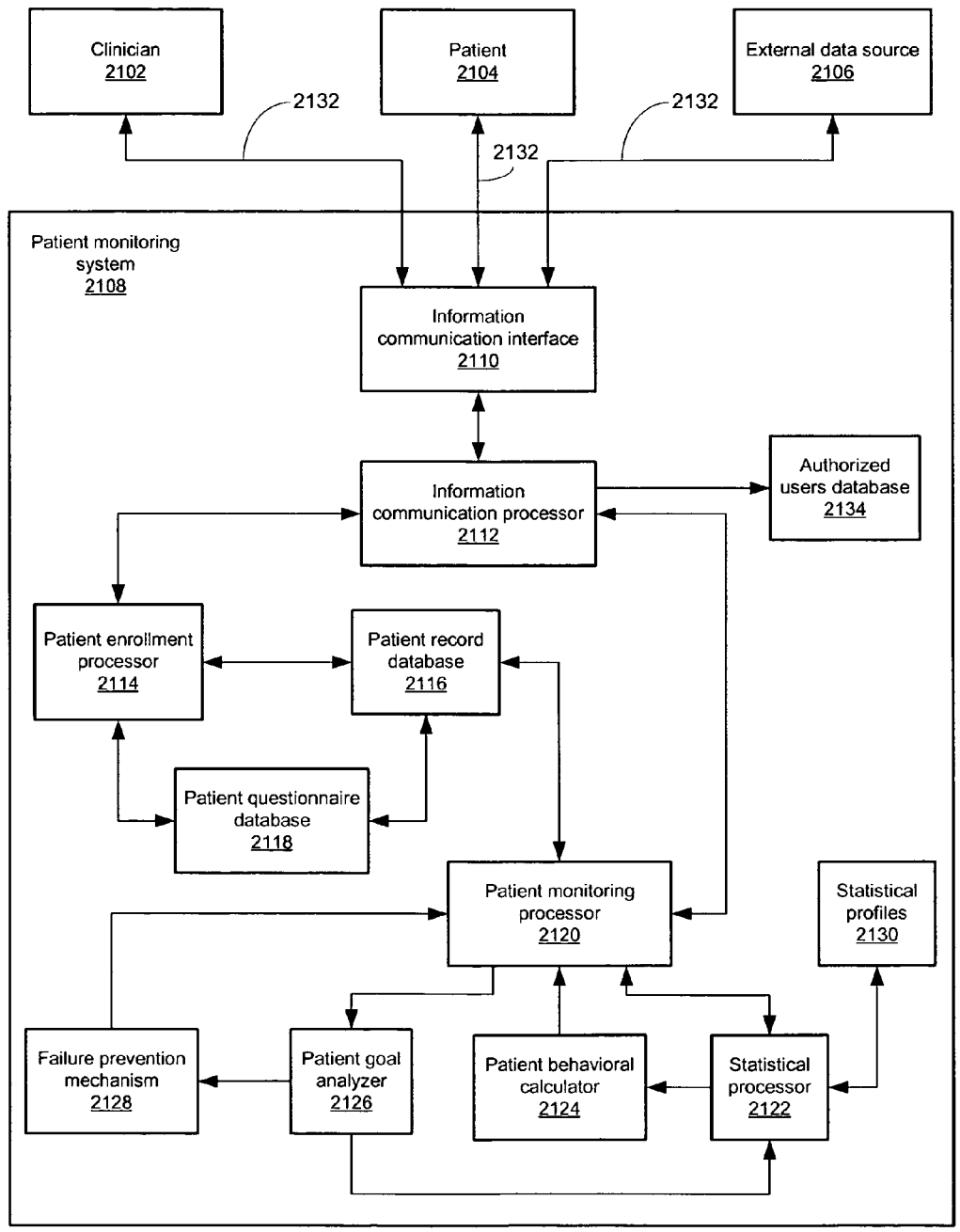
FIG. 21 is a block diagram of one embodiment of a patient monitoring system.

FIG. 21 is a block diagram of a patient monitoring system 2108 according to one embodiment. The patient monitoring system 2108 includes an information communication interface 2110 coupled with an information communication processor 2112. The information communication interface 2110 facilitates communication between a clinician 2102, a patient 2104, an external data source 2106, or combinations thereof, and the information communication processor 2112 through a communication network 2132. The information communication interface 2110 also facilitates communication between the clinician 2102, the patient 2104, the external data source 2106, or combinations thereof, and the patient enrollment processor 2114. The information communication interface 2110 further facilitates communication with the patient monitoring processor 2120. Herein, the phrase "coupled with" is defined to mean directly connected to or indirectly connected through one or more intermediate components. Such intermediate components may include both hardware and software based components.

To clarify the use in the pending claims and to hereby provide notice to the public, the phrases "at least one of <A>, <B>, ... and <N>" or "at least one of <A>, <B>, ... <N>, or combinations thereof" are defined by the Applicant in the broadest sense, superceding any other implied definitions herebefore or hereinafter unless expressly asserted by the Applicant to the contrary, to mean one or more elements selected from the group comprising A, B, ... and N, that is to say, any combination of one or more of the elements A, B, .. . or N including any one element alone or in combination with one or more of the other elements which may also include, in combination, additional elements not listed.

As used herein, the term "processor" means a processor implemented in hardware, software or a combination thereof. For example, a "processor" may be a processor implemented as a reduced instruction set computer (RISC), a processor implemented as a complex instruction set computer (CISC), or combination thereof. In another example, a "processor" may be a software module written in a computer programming language, such as Fortran, C, C#, .NET, Java, Javascript, Splus, R, SAS, or combinations thereof. Other computer programming languages are also possible. As another example, a "processor" may be a separate computer system, with its own internal processor (such as an x86-based processor or RISC processor), memory (including both RAM and internal storage devices), input devices (such as a keyboard, microphone, and mouse) and output devices (such as a visual display device and an audio display device) coupled with the patient monitoring processor 2120 using a network technology that is presently known or later developed, such as Ethernet, 802.11 a/b/g, Bluetooth, or combinations thereof.

Where the clinician 2102 uses the communication network 2132 to communicate with the patient monitoring system 2108, the patient 2104 or the external data source 2106 can use the same communication network 2132 to communicate with the patient monitoring system 2108. In an alternative embodiment, the patient 2104 and the external data source 2106 use alternative communication networks 2132 to communicate with the patient monitoring system 2108. For example, where the clinician 2102 uses a packet-switched communication network 2132, such as the Internet, to communicate with the patient monitoring system 2108, the patient 2104 may use a circuit-switched network, such as the telephone network, and the external data source 2106 may use a combination of a circuit-switched network and a packet-switched network.

In one embodiment, the information communication processor 2112 processes communication transmissions sent from and received by the patient monitoring system 2108 via the information communication interface 2110, as will be explained with reference to FIG. 1 below. The information communication processor 2112 is also coupled with an authorized users database 2134 that stores and maintain records of users authorized to access the patient monitoring system 2108. The authorized users database 2134 is accessible by the patient enrollment processor 2114 or the patient monitoring processor 2120 via the information communication processor 2112.

The patient monitoring system 2108 further includes a patient enrollment processor 2114 coupled with the information communication processor 2112, which allows a clinician 2102 to communicate with the patient enrollment processor 2114 for enrolling new patients in the patient monitoring system 2108. Alternatively, a patient 2104 may communicate with the patient enrollment processor 2114 such as to self-enroll. The patient enrollment processor 2114 is coupled with a patient record database 2116 which, in one embodiment as will be explained in detail below with reference to FIG. 2, stores records of patients enrolled in the patient monitoring system 2108. The patient enrollment processor 2114 is also coupled with a patient questionnaire database 2118. As explained with reference to FIG. 5, the patient questionnaire database 2118 stores predetermined questionnaires selectable by the clinician 2102 for associating with a patient record stored in the patient record database 2116. The patient enrollment processor 2114 may be configured to access the patient record storage 2116 and the patient questionnaire database 2118 as will be described.

The patient monitoring system 2108 additionally includes a patient monitoring processor 2120 coupled with the information communication interface 2110 via the information communication processor 2112. The patient monitoring processor 2120 may communicate with either the clinician 2102, the patient 2104, or the external data source 2106. As will be explained with reference to FIG. 6, the clinician 2102 communicates with the patient monitoring processor 2120 after enrolling a new patient in the patient monitoring system 2108 to initially establish a patient statistical profile. The clinician 2102 may later access the patient monitoring system 2108 to update the stored patient statistical profile. As will be discussed, the initial state of the patient statistical profile may be initially undefined, to be updated and refined based on interaction with the patient, clinician or other source, it may be based on a previously developed population statistical profile, it may be based on patient specific data obtained by the system 2108 via the patient, clinician or other source, or the patient statistical profile may be initially defined base on a combination thereof.

In general, a population statistical profile is model of a patient-population, such that for a given input of an individual patient, the population statistical profile is able to produce a predicted output, e.g. the most likely output from among the modeled patient-population, based on the given input. In one embodiment, the population statistical profile is continually updated with feedback from individual patient experiences using principles of statistical process control. The system 2108 may include multiple population statistical profiles associated with various overlapping and/or non-overlapping patient populations defined, as was described above, based on patient demographics, medical condition(s), symptom(s), prescribed medications, etc., or combinations thereof. The population statistical profile includes statistical information which may further help patients enrolled in the patient monitoring system 2108 to achieve a particular behavioral goal and/or a behavioral objective. Each patient may have their own patient statistical profile generated based on a particular population statistical profile, covering the patient population which includes the given patient, and refined based on the individual experiences of the patient, the population or a combination thereof. Alternatively, each patient may utilize a particular population statistical profile, rather than having an individual patient statistical profile, which is refined based on the experiences of the associated population, including or excluding the given patient. The patient and/or population statistical profile may also include information that allows the patient monitoring system 2108 to determine the types of behavior modification treatments that are successful in achieving a particular behavioral goal. The statistical profile may also include information as to what types of treatments to start first before starting another treatment. For example, the statistical profile may include success rates based on a percentage of population for a particular treatment. The statistical profile may also include failure rates based on a percentage of population for a particular treatment. The statistical profile may also provide information as to how a particular goal should be achieved based on responses to particular treatments from patients undergoing that treatment, similar to pediatric growth curves, which indicate percentiles of typical growth rates. The statistical profile may also include reference information, indicating which statistical methods, databases, articles or expert information were used to derive the profile and the time stamp of the profile and each source. Other types of statistical information for achieving behavior modification are also possible.

As will be explained with reference to FIG. 10, the patient 2104 communicates with the patient monitoring processor 2120 to answer targeted messages sent by the patient monitoring processor 2120 based on the questionnaire(s) previously associated with the patient's 2104 stored record and the patient's 2104 stored statistical profile. The response(s) provided by the patient 2104 may be used by the patient monitoring processor 2120 to modify the stored statistical profile associated with the patient 2104, may be used by the patient monitoring processor 2120 to modify the stored statistical profile associated with a second patient similarly situated as the first patient 2104, may be used to modify the statistical profile(s) associated with a set or population of patients which contains the patient, or combinations thereof.

According to the embodiment of FIG. 21, the patient monitoring processor 2120 is further coupled with a statistical processor 2122, a patient behavioral calculator 2124, a patient goal analyzer 2126, and a failure prevention mechanism 2128. In one embodiment, the statistical processor 2122 generates a statistical profile for the patient 2104 based on statistical information provided by the clinician 2102, provided by the external data source 2106, or combinations thereof. The statistical processor 2122 may also be used to generate a new statistical profile or modify an existing statistical profile based on responses by the patient 2104 to one or more targeted messages sent by the patient monitoring processor 2120. The statistical processor 2122 is coupled with the patient behavioral calculator 2124 and a statistical profile storage 2130. The patient goal analyzer 2126 may also be coupled with the statistical processor 2122.

As will be explained in further detail below, the patient behavioral calculator 2124 may calculate a behavioral path to a behavioral objective for the patient 2104 based on a statistical profile calculated by the statistical processor 2122. The patient behavioral calculator 2124 may also calculate a plurality of intermediate goals along the behavioral path for achieving the behavioral objective. As will be explained with reference to FIG. 12, in one embodiment, the patient behavioral calculator 2124 may also be configured to re-calculate the behavioral path and the plurality of intermediate goals based on whether the statistical processor 2122 modified the statistical profile associated with the patient 2104.

The patient goal analyzer 2126 is coupled with the patient monitoring processor 2120 and the statistical processor 2122. The patient goal analyzer 2126 is operative to calculate or determine whether the patient 2104 has achieved, in whole or in part, an intermediate goal along the calculated behavioral path towards the behavioral objective. Based on the result determined or calculated by the patient goal analyzer 2126, the patient goal analyzer 2126 may initiate the failure prevention mechanism 2128 to prevent the patient 2104 from failing to achieve the behavioral objective. As explained with reference to FIG. 13, activating the failure prevention mechanism 2128 may include alerting a person, such as the clinician 2102 or the patient 2104, as to the patient's 2104 failing progress or may include sending a failure prevention message to the patient 2104 when the patient 2104 next initiates a session with the patient monitoring system 2108.

Figure 22:
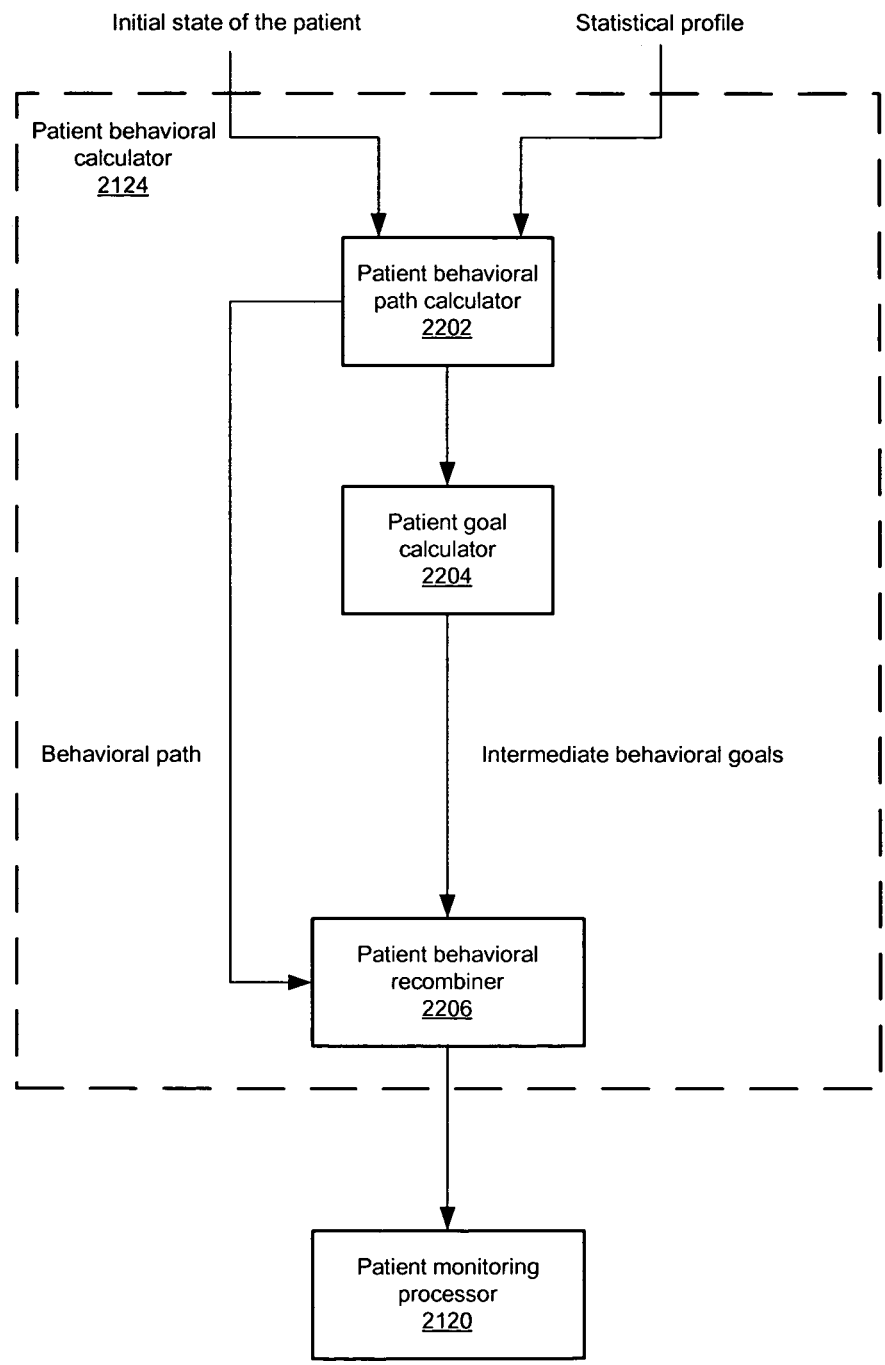
FIG. 22 is a block diagram of one embodiment of a patient behavioral calculator.

FIG. 22 depicts a block diagram of one embodiment of the patient behavioral calculator 2124, described above. In one embodiment, the patient behavioral calculator 2124 is implemented in a processor, as described above. The patient behavioral calculator 2124 includes a patient behavioral path calculator 2202 coupled with a patient goal calculator 2204 and a patient behavioral recombiner 2206. The patient goal calculator 2204 is also coupled with the patient behavioral recombiner 2206. In one embodiment, the patient goal calculator 2204 is a processor. The patient behavioral path calculator 2202 calculates the behavioral path of the patient based on an initial state of the patient submitted by the clinician and a statistical profile associated with the patient, which, as described above, may have been based on a population statistical profile associated with a give patient population that includes the patient. The initial state of the patient includes information such as the patient's current health, demographic information, or other personal information. The initial state of the patient 2104 may also be the state of the patient 2104 prior to a subsequent communication session between the patient 2104 and the patient monitoring system 2108.

The patient behavioral path calculator 2202 also communicates with the patient goal calculator 2204, which allows the patient goal calculator 2204 to calculate one or more intermediate patient behavioral goals along the patient's behavioral path. For example, the patient goal calculator 2204 may use the behavioral path to determine where along the behavioral path the patient should have intermediate behavioral goals. Alternatively, or in addition to using the behavioral path to determine the patient's intermediate goals, the patient goal calculator 2204 may also use the patient statistical profile, the population statistical profile, previously calculated goals and/or objectives for other patients, or combinations thereof.

The patient goal calculator 2204 communicates the calculated intermediate behavioral goals to the patient behavioral recombiner 2206. The patient behavioral recombiner 2206 is operable to combine the intermediate behavioral goals outputted by the patient goal calculator 2204 and the patient behavioral path outputted by the patient behavioral path calculator 2202. By combining the patient behavioral path with the calculated intermediate behavioral goals, the patient behavioral recombiner 2206 is able to produce a complete behavioral path for the patient monitoring processor 2120. In one embodiment, the patient behavioral recombiner 2206 is a processor.

Figure 23A:
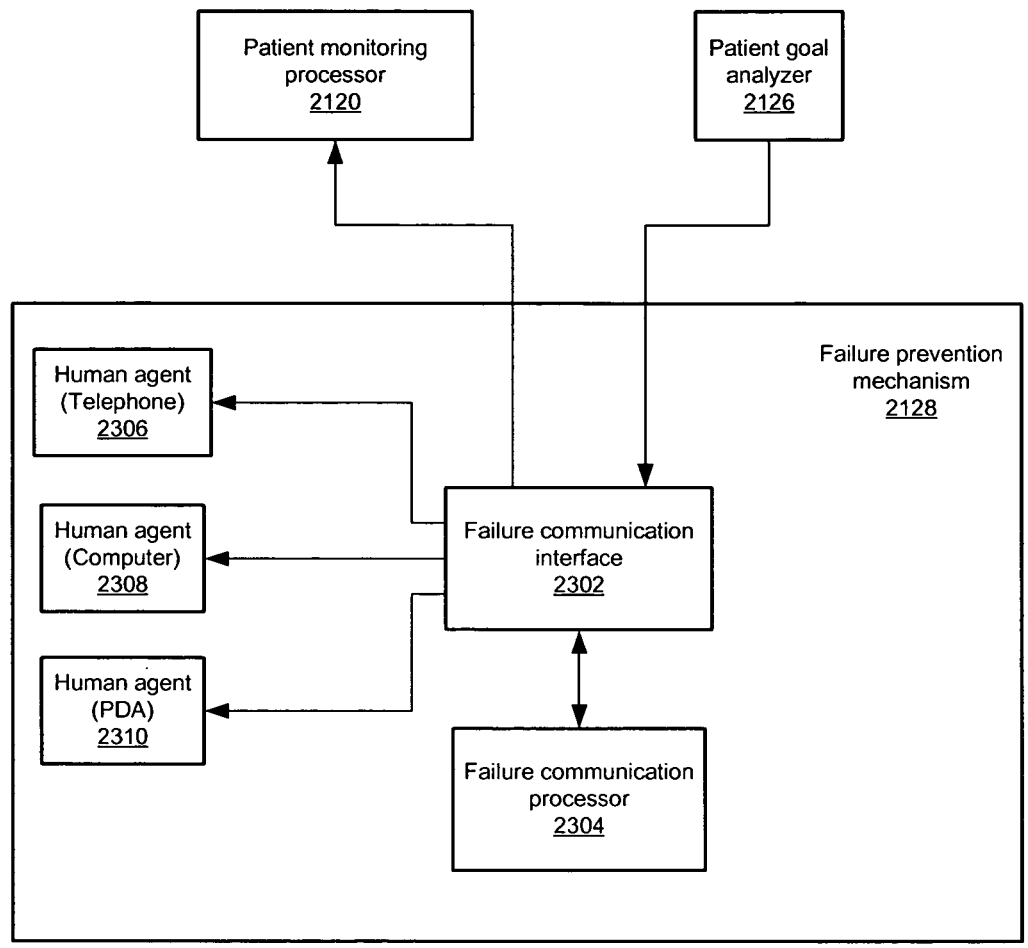
FIG. 23A is a block diagram of one embodiment of a failure prevention mechanism.

FIG. 23A is a block diagram of one embodiment of a failure prevention mechanism 2128. The failure prevention mechanism 2128 is operative to one or more failure prevention messages. A failure prevention message is a message designed to prevent the patient 2104 from failing to achieve a patient behavioral goal and/or a patient behavioral objective. The failure prevention message may be a positive reinforcement message, a negative reinforcement message, or a combination thereof. For example, the failure prevention message may include encouraging words to motivate the patient to continue along the behavioral path. The failure prevention message may also include disparaging words to motivate the patient to continue along the behavioral path.

In the embodiment shown in FIG. 23A, the failure prevention mechanism 2128 is a human alert system. The failure prevention mechanism 2128 includes a failure communication interface 2302 coupled with a failure communication processor 2304. The failure communication interface 2302 is coupled with a human agent via a telephone 2306, a human agent via a computer 2308, and a human agent via a personal display assistant (PDA) 2310. In one embodiment, the failure communication interface 2302 is a wired interface, such as an Ethernet port, a parallel communication port, a serial communication port, a USB port, a wireless interface, such as an infrared receiver, a radio signal receiver, a Bluetooth receiver, or other equivalent communication interface, or combination thereof. The failure communication interface 2302 is operable to receive the notification from the patient goal analyzer 2126 or the patient monitoring processor 2120 to activate the human alert system. The failure communication interface 2302 communicates with the failure communication processor 2304 to send the notification from the patient monitoring processor 2120 or the patient goal analyzer 2126 to activate the human alert system.

After the failure communication processor 2304 has received a notification to activate the human alert system, the failure communication processor 2304 alerts the human agents coupled with the failure communication interface 2302. In one embodiment, the failure communication processor 2304 sends a message to the human agents connected with the failure communication interface 2302 alerting the human agents that the patients has failed to meet a behavioral goal and/or a behavioral objective. The human agents coupled with the failure communication interface 2302 may include, but are not limited to, the clinician, a health-care provider, a family relative of the patient, or combination thereof. The message sent from the failure communication processor 2304 may be an audible or visual message depending on how the human agent is coupled with the failure communication interface 2302. For example, if the human agent 2306 is coupled with the failure communication interface 2302 using a telephone, the message sent from the failure communication processor 2304 is an audible message. In another example, the human agent 2308 coupled with the failure communication interface 2302 using a computer and human agent 2310 coupled with the failure communication interface 2302 using a PDA receive an audible message, a visual message, or a combination thereof.

Figure 23B:
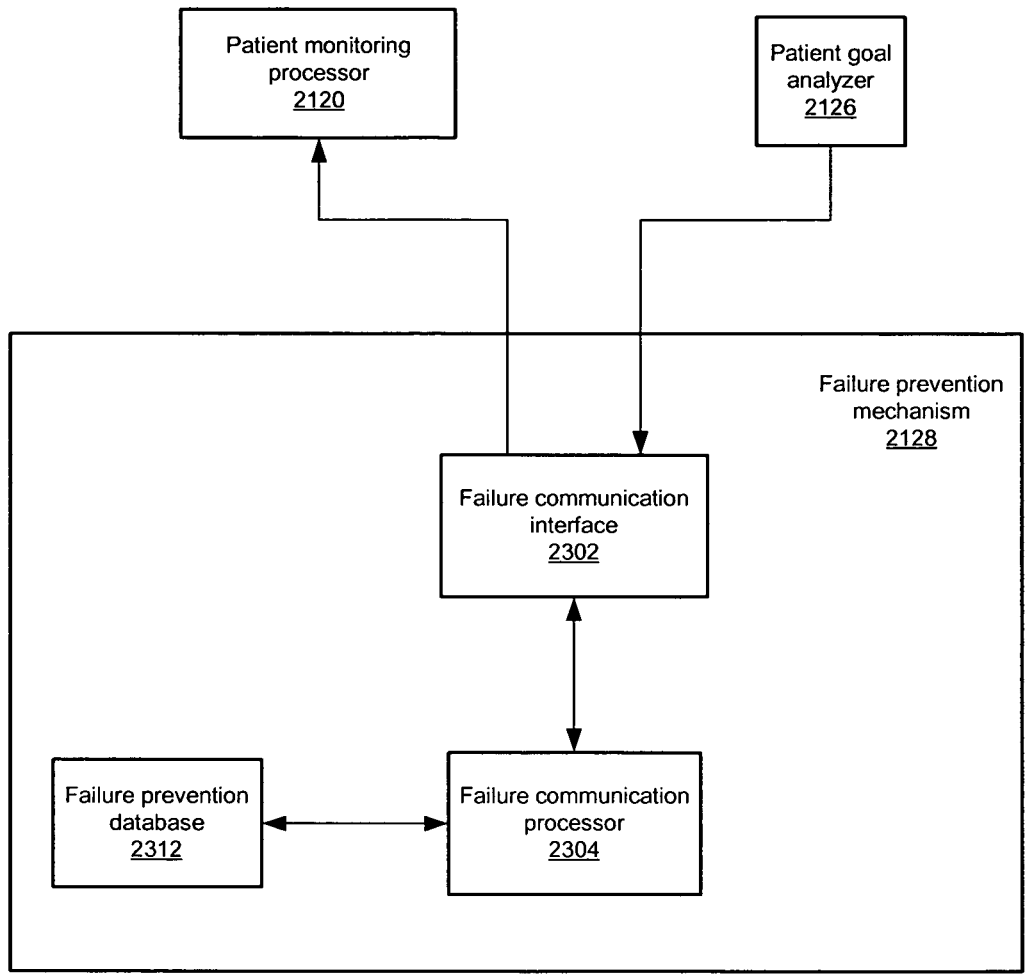
FIG. 23B is a block diagram of another embodiment of the failure prevention mechanism.

FIG. 23B is a block diagram of another embodiment of the failure prevention mechanism 2128. In the embodiment shown in FIG. 23B, the failure prevention mechanism 2128 includes a failure communication interface 2302 coupled with the failure communication processor 2304. The failure communication processor 2304 is coupled with the failure prevention database 2312. The failure prevention database 2312 stores failure prevention messages selectable by the failure communication processor 2304 based on the notification sent by the patient monitoring processor 2120 or the patient goal analyzer 2126. As will be discussed with respect to FIG. 13, the failure communication processor 2304, the patient monitoring processor 2120, or the patient goal analyzer 2126, are capable of selecting a failure prevention message from the failure prevention database 2312. In one embodiment, the failure prevention database 2312 is a software-implemented database residing in the same computer system as the failure communication processor 2304. In another embodiment, the failure prevention database 2312 is a series of files logically arranged in an operating system, such that each file represents an individual patient record. In yet a further embodiment, the failure prevention database 2312 resides on a separate computer system, wherein the computer system has its own internal processor (such as an x86-based processor or RISC processor), memory (including both RAM and internal storage devices), input devices (such as a keyboard, microphone, and mouse) and output devices (such as a visual display device and an audio display device), and is coupled with the failure communication processor 2304 using a network technology such as Ethernet, 802.11 a/b/g, Bluetooth, or combinations thereof.

The system 2108 is accessible by various entities, referred to as "actors" for various purposes, referred to as "roles." For discussion purposes, the description accompanying FIGS. 1-20 refers to actors including the clinician 2101, patient 2104 and external data source(s) 2106 and the particular roles with which they access the system 2108. While the discussion below differentiates between the clinician 2102, the patient 2104, and the external data source 2106 accessing the patient monitoring system 2108, it should be understood that any one of these actors can be substituted for another, i.e. each entity may access the system in under the guise of one or more roles, which may overlap with the roles of other entities. For example, where the description below discusses the clinician 2102 accessing the patient monitoring system 2108, it should also be understood that the patient 2104 or the external data source 2106 may also access the patient monitoring system 2108 as the clinician 2102 would. Similarly, where the description below discusses the patient 2104 or the external data source 2106 accessing the patient monitoring system 2108, it should be understood that the clinician 2102 may also access the patient monitoring system 2108 in a similar manner, such as where the clinician 2102 is acting on behalf of the patient 2104 or the external data source 2106. In one implementation of the monitoring system 2108, the patient 2104 may self-enroll themselves in the monitoring system 2108, define their own goals and monitor their own progress. In this implementation, the patient 2104 acts in the roles of both a patient 2104 and a clinician 2102.

Furthermore, the actors discussed herein, e.g. the clinician 2102, the patient 2104, and the external data source 2106, are not limited thereto. For example, the patient 2104 may authorize a surrogate to act on behalf of the patient 2104. Similarly, the clinician 2102 or the external data source 2106 may authorize a third-party to act on behalf of the clinician 2102 or the external data source 2106, such as where the clinician 2102 authorizes a health management organization or hospital to act on behalf of the clinician 2102. In these instances, the patient monitoring system 2108 may further be modified to accept access attempts and changes to the patient monitoring system 2108 made by these third-parties. For example, the authorized users database 2134 may be modified with rights restrictions so as to distinguish between parties with access-only (e.g., read-only) authorization, modification (e.g., write) authorization, and execution (e.g., execute) authorization, or combinations thereof. As an example, a surrogate of the patient 2104 may have access-only authorization, the patient 2104 may have modification authorization, and the clinician 2102 may have execution authorization. These rights restrictions would further limit or expand the ability of the user (e.g., the clinician 2102, the patient 2104, a surrogate, the external data source 2106, etc.) currently accessing the system, such that certain tasks may only be performed if the user has an authorized set of right restrictions. In one embodiment, these right restrictions are stored and maintained by the authorized users database 2134.

Turning now to FIG. 1 is a flowchart of one embodiment of the operation of accessing a patient enrollment and monitoring system. As shown in FIG. 1, the patient monitoring system 2108 receives a session initiation request from a data source (Block 102). The initiation request may originate from a clinician 2102, a patient 2104, and/or an external data source 2106. While the clinician 2102, the patient 2104, and the external data source 2106, are shown in communication with the patient monitoring system 2108, in an alternative embodiment other entities may also be in communication with the patient monitoring system 2108 as well. For example, a healthcare management organization (not shown) may be in communication with the patient monitoring system 2108 using an automated service. In yet another alternative embodiment, more than one entity is capable of accessing the patient monitoring system 2108 during a given time interval, either simultaneously, substantially simultaneously, sequentially or combinations thereof. For example, clinician 2102, patient 2104, or external data source 2106 could access the patient monitoring system 2108 substantially simultaneously. Alternatively, while the clinician 2102 is accessing the patient monitoring system 2108, the patient monitoring system 2108 may prevent the patient 2104 and the external data source 2106 from accessing the patient monitoring system 2108.

The external data source 2106 is a device, organization, other entity, or combination thereof, capable of providing patient information to the patient monitoring system 2108. In one embodiment, the external data source 2106 is a glucometer used for measuring a patient's glucose level and programmed to access the patient monitoring system 2106 at scheduled time intervals. In another embodiment, the external data source 2106 is an electronic scale used for measuring a patient's weight and programmed to access the patient monitoring system 2106 at scheduled time intervals. The external data source 2106 may also be configured to access the patient monitoring system 2108 based on pre-determined criteria, such as a patient's glucose level or a patient's weight. The external data source 2106 could also be an entity other than an electronic or mechanical device, such as a health management organization, insurance company, employer, physician, clinician, or an electronic system, such as a database or other system operated thereby, capable of accessing the patient monitoring system 2108.

When the clinician 2102, the patient 2104, or the external data source 2106 sends a session initiation request to the patient monitoring system 2108, the patient monitoring system 2108 then prompts the data source, such as the clinician 2102, to provide user identification information (Block 104). The patient monitoring system 2108 prompts the clinician 2102 using the information communication processor 2112 via the information communication interface 2110. The communication network 2132 used to communicate with the patient monitoring system 2108 may affect the type of information communication interface 2110 used to communicate with the clinician 2102. For example, the communication network 2132 may include a packet-switched network, a circuit-switched network, or a combination thereof. In one embodiment, the clinician 2102 contacts the patient monitoring system 2108 using a telephone via the Plain Old Telephone Service (POTS). Where the clinician 1508 uses a telephone to contact the patient monitoring system 2108, the clinician may communicate with the patient monitoring system 2108 through the information communication interface 2110 using dual tone multi-frequency ("DTMF") signaling, TTY device, via voice recognition, or combinations thereof. The information communication interface 2110 interacts with the clinician 2102 by providing voice prompts to the clinician 2102. For example, the information communication interface 2110 may provide a voice menu to the clinician 2102 which presents instructions and/or available options. The IVR interface facilitates communication with the clinician via computer generated, or computer provided pre-recorded, audible prompts. Using the IVR, the information communication interface 2110 allows the clinician to respond using the touch-tone keys of the clinician's keypad and/or by speaking responses. The information communication interface 2110 may then record, encode, translate and/or convert the verbal response or key presses and transmit them to the information communication processor 2112.

Where the clinician 2102 communicates with the patient monitoring system 2108 using a telephone, the information communication interface 2110 may prompt the clinician 2102 to provide, verbally or via the keypad, a personal identification number (PIN) for authorizing access to the patient monitoring system 2108 (Block 104). In an alternative embodiment, the information communication interface 2110 uses voice recognition technology to determine whether the clinician 2102 is authorized to access the patient monitoring system 2108. The information communication interface 2110 then communicates with the information communication processor 2112 to determine whether the clinician 2102 is authorized to access the patient monitoring system 2108.

In an alternative embodiment, the clinician 2102 uses a telephone connected to a packet-switched network to contact the patient monitoring system 2108, which is connected to a circuit-switched network. For example, the clinician 2102 may contact the patient monitoring system 2108 using voice-over-IP (VOIP) technology and a voice-over-IP (VOIP) protocol, such Session Initiation Protocol ("SIP"), an H.323 protocol, other VOIP protocols, or a combination thereof.

In another embodiment the clinician 2102 contacts the patient monitoring system 2108 using a packet-switched network, such as where the clinician 2102 uses a computer, personal digital assistant, cell phone or other suitable general purpose or dedicated device to communicate with the information communication interface 2110. Where the clinician 2102 uses a computer to contact the patient monitoring system 2108 over a packet-switched network, the clinician 2102 may use a computer coupled with a wired and/or wireless network, such as private or public network, e.g. the Internet, intranet or combination thereof, to communicate through the network with the information communication interface 2110. In an alternative embodiment, the computer is coupled with a modem capable of using POTS to communicate with the patient monitoring system 2108. In this alternative embodiment, the communication network 2132 may include both a circuit-switched network and a packet-switched network. Where the clinician 2102 uses a computer to contact the patient monitoring system 2108, the computer may use various protocols to communicate with the patient monitoring system 2108 through the information communication interface 2110. For example, the computer may use application layer protocols, such as HTTP, FTP, SMTP, SSH, transport layer protocols, such as TCP, UDP, RUDP, network protocols, such as ICMP, IGMP, ARP, or combinations thereof.

Where the clinician 2102 uses HTTP or other similar protocol to communicate with the patient monitoring system 1058, the information communication interface 2110 presents a textual and/or graphical interface, such as an Internet web site, for communicating with the clinician 2102. In this alternative embodiment, the clinician 2102 may be prompted to provide a username and password to the Internet web site for accessing the patient monitoring system 2108 (Block 104). The information communication interface 2110 then communicates this username and password combination to the information communication processor 2112 (Block 106). The information communication processor 2112 then determines whether the clinician 2102 is authorized to access the patient monitoring system 2108 by referring to an authorized user database 2134 (Block 108). In an alternative embodiment, the Internet web site may request that the clinician 2102 provide a pre-generated security certificate for accessing the patient monitoring system 2108. The information communication interface 2110 then relays this security certificate to the information communication processor 2112, which then compares the security certificate with the security certificates of authorized users stored in the authorized user database 2134. In yet another embodiment, the Internet web site may request that the clinician 2102 provide biometric information to the information communication interface 2110, such as a real-time scan of the clinician's fingerprint. The information communication interface 2110 then relays the biometric information to the information communication processor 2112, which then compares the clinician provided biometric information with a database of biometric information of authorized users 2134.

In one embodiment, the authorized users database 2134 is a software-implemented database residing in the same computer system as the information communication processor 2112. In another embodiment, the authorized users database 2134 is a series of files logically arranged in an operating system, such that each file represents an individual patient record. The authorized users database 2134 could further reside on a separate computer system, wherein the computer system has its own internal processor (such as an x86-based processor or RISC processor), memory (including both RAM and internal storage devices), input devices (such as a keyboard, microphone, and mouse) and output devices (such as a visual display device and an audio display device), and is coupled with the information communication processor 2112 using a network technology such as Ethernet, 802.11 a/b/g, Bluetooth, or combinations thereof.

Once the information communication processor 2112 has received the user identification information from the information communication interface 2110, the information communication processor 2112 then determines whether to allow the clinician 2102 access to the patient monitoring system 2108 (Block 108). If the information communication processor 2112 determines that the clinician 2102 is not authorized to access the patient monitoring system 2108, such as where the clinician provided user identification information does not exist in the authorized users database 2134, the information communication processor 2112 relays this fact to the information communication interface 2110, which may then prompt the clinician 2102 to re-provide the clinician's user identification information. In an alternative embodiment the information communication interface 2110 may deny access to the clinician 2102 and then require the clinician 2102 to wait for a predetermined amount of time before again accessing the patient monitoring system 2108. For example, if the information communication processor 2112 determines that the clinician 2102 has not provided authorized user identification information to access the patient monitoring system 2108, the information communication interface 2110 may state that the clinician 2102 must wait two hours before again attempting to access the patient monitoring system 2108. In yet another alternative embodiment, the information communication processor 2112 allows a predetermined number of access failures before denying access to the clinician. For example, the information communication processor 2112 may allow the clinician 2102 to attempt to provide valid user identification information up to five times before determining that the clinician 2102 is not authorized to access the patient monitoring system 2108.

Once the information communication processor 2112 has determined that the clinician 2102 is authorized to access the patient monitoring system 2108, the information communication interface 2110 provides one or more options to the clinician 2102 as to how to proceed (Block 110). For example, the information communication interface 2110 may communicate a question or menu to the clinician 2102 as to whether the clinician 2102 wants to enroll a new patient in the patient monitoring system 2108 (Block 114) or whether the clinician 2102 wants to access a previously stored patient's record (Block 118). If the clinician 2102 has initiated communication with the patient monitoring system 2108 using a telephone, this question or menu is presented to the clinician 2102 using the aforementioned IVR interface. Alternatively, where the clinician 2102 has initiated communication with the patient monitoring system 2108 using a computer, this question or menu may be presented textually or graphically via a web page of the Internet web site.

Where the clinician 2102 provides a response that the clinician wants to enroll a new patient in the patient monitoring system 2108 (Block 112), the patient enrollment processor 2114 facilitates the process of enrolling a new patient (Block 114). As shown in FIG. 21, the clinician 2102 communicates with the patient enrollment processor 2114 via the information communication interface 2110 coupled with the information communication processor 2112. In one embodiment, the patient enrollment processor 2114 could be the same processor as that of the information communication processor 2112. In another embodiment, the patient enrollment processor 2114 is a distinct processor.

Figure 2:
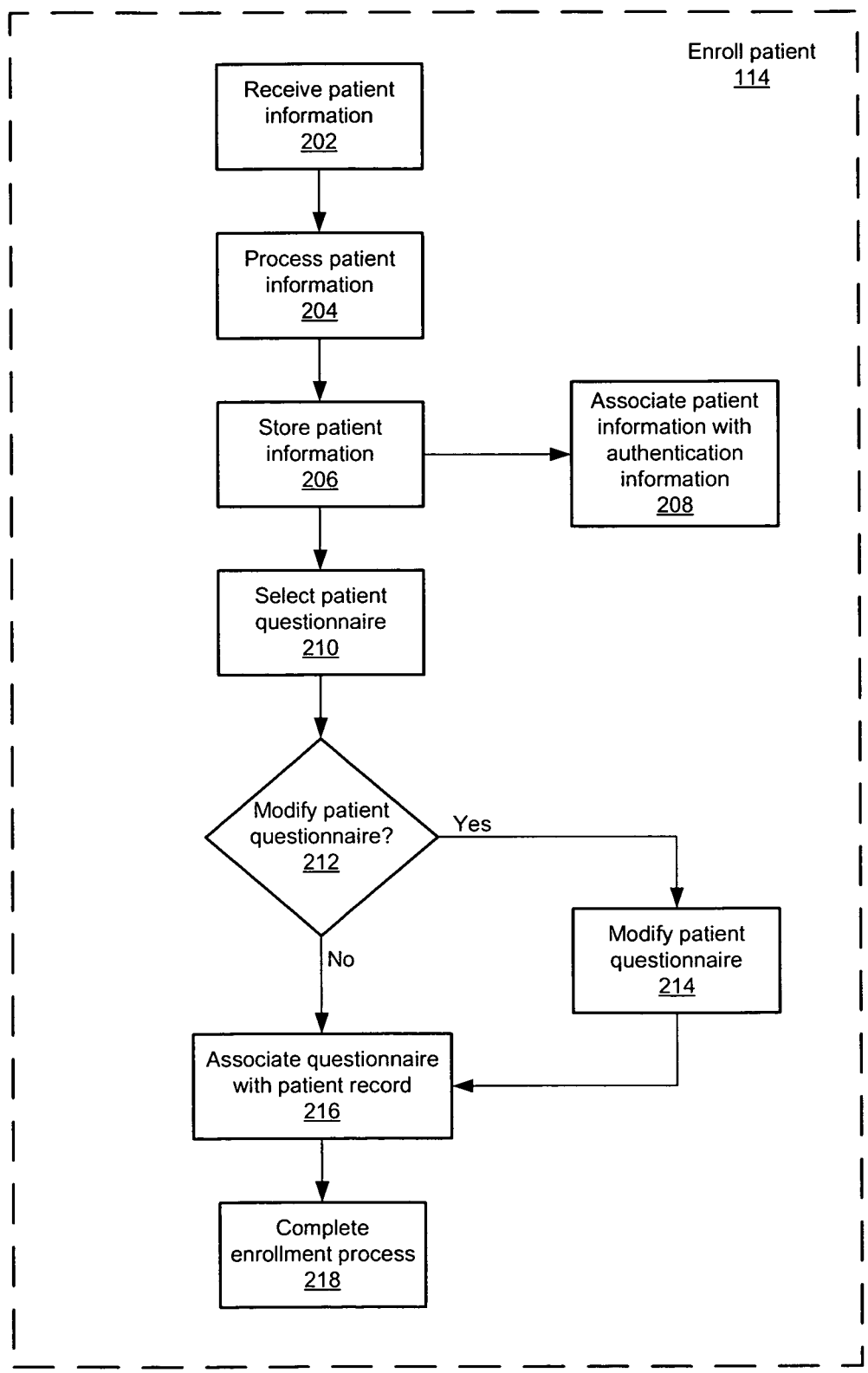
FIG. 2 is a flowchart of one embodiment of enrolling a patient in the patient monitoring system.
Figure 3:
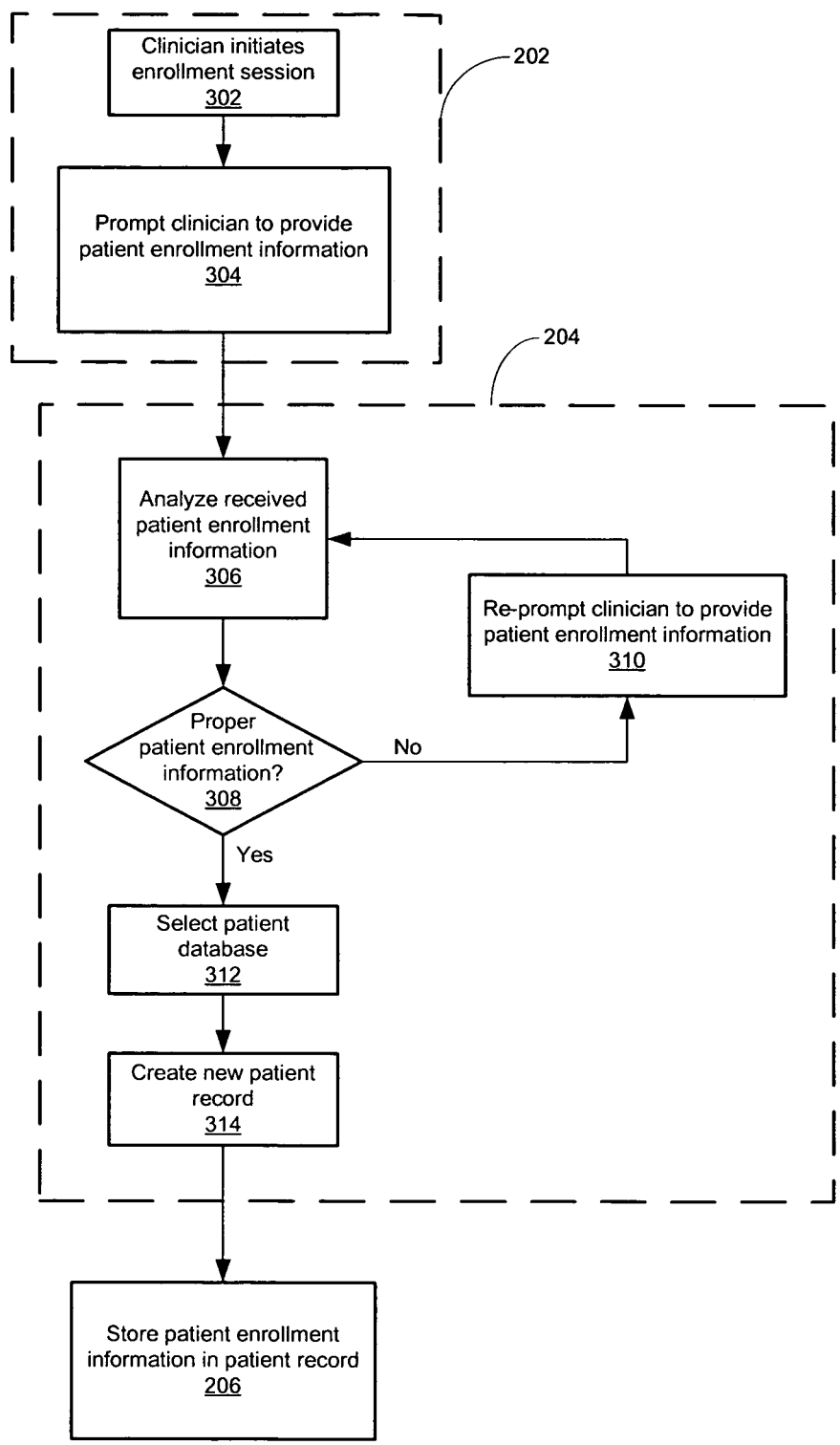
FIG. 3 is a flowchart of one embodiment of receiving and processing patient enrollment information.

FIG. 2 is a flowchart showing one embodiment of the operation of enrolling a patient in the patient monitoring system 2108. Once the clinician 2102 has chosen to enroll a new patient in the patient monitoring system 2108, the patient enrollment processor 2114 receives the patient enrollment information via the information communication interface 2110 (Block 202). As shown in FIG. 3, receiving the patient enrollment information may first include the clinician 2102 initiating the enrollment session (Block 302). Initiating the enrollment session may be based on the clinician's response to the option of whether to enroll a new patient in the patient monitoring system 2108 or to access the patient monitoring system 2108. When the clinician 2102 has initiated the patient enrollment session, the patient enrollment processor 2114 instructs the information communication interface 2110 to prompt the clinician 2102 to provide patient enrollment information (Block 304). In one example, where the clinician 2102 communicates using a telephone, the information communication interface 2110 present prompts to the clinician 2102 using an IVR interface. In another example, the information communication interface 2110 presents an Internet site to the clinician 2102 for providing patient enrollment information. Examples of patient enrollment information include contact information for the new patient, such as the patient's telephone number, patient demographic data, and clinical parameters.

Referring briefly back to FIG. 2, after the patient enrollment processor 2114 receives the patient enrollment information, the patient enrollment processor 2114 proceeds to process the patient enrollment information (Block 204). As shown in FIG. 3, the patient enrollment processor 2114 analyzes the enrollment information on a real-time basis as it is provided to the patient enrollment processor 2114 (Block 306). For example, the patient enrollment processor 2114 might check to determine that a valid phone number has been provided before prompting the clinician 2102 to provide demographic information (Block 308). In an alternative embodiment, the patient enrollment processor 2114 accepts all of the patient enrollment information before analyzing the received patient enrollment information for its accuracy and/or validity (Block 308). If the patient enrollment processor 2114 determines that the patient enrollment information is not valid, such as receiving a string of letters instead of a string of numbers for the patient's phone number, the patient enrollment processor 2114 instructs the information communication interface 2110 to re-prompt the clinician 2102 to provide patient enrollment information (Block 310). In an alternative embodiment, the patient enrollment processor 2114 presents to the clinician 2102 an option to review the patient enrollment information before storing the patient enrollment information in the patient record database 2116.

In one embodiment of the patient monitoring system 2108, the patient enrollment processor 2114 creates a data record for the new patient based on the patient enrollment information in a patient record database 2116 coupled with the patient enrollment processor 2114. It is also possible that the patient record database 2116 is communicatively coupled with the patient enrollment processor 2114 from another system. In an alternative embodiment, the patient enrollment processor 2114 is coupled with multiple databases and may prompt the clinician to select one or more databases in which to create the new patient record. For example, the clinician 2102 may be authorized to access multiple databases, such as where the clinician 2102 maintains a database for smoking patients and another database for overweight patients (Block 312). Alternatively, separate databases may be maintained based on other attributes such as gender, insurance carrier, etc., wherein a patient record may be created and maintained one or more of each of the relevant databases. In this embodiment, the patient enrollment processor 2114 communicates with the information communication interface 2110 to provide an option to the clinician 2102 to select a particular database(s). Once the clinician 2102 has provided the patient enrollment information requested by the patient enrollment processor 2114 and the patient enrollment processor 2114 has checked the clinician provided patient enrollment information, the patient enrollment processor 2114 then creates a new patient record in the patient record database 2116 (Block 314).

In one embodiment, the patient record database 2116 is a software-implemented database residing in the same computer system as the patient enrollment processor 2114. In another embodiment, the patient record database 2116 is a series of files logically arranged in an operating system, such that each file represents an individual patient record. In yet a further embodiment, the patient record database 2116 resides on a separate computer system, wherein the computer system has its own internal processor (such as an x86-based processor or RISC processor), memory (including both RAM and internal storage devices), input devices (such as a keyboard, microphone, and mouse) and output devices (such as a visual display device and an audio display device), and is coupled with the patient enrollment processor 2114 using a network technology such as Ethernet, 802.11 a/b/g, Bluetooth, or combinations thereof.

Referring back to FIG. 2, once the patient enrollment processor 2114 has created the new patient record, the patient enrollment processor 2114 then stores the provided patient enrollment information in the created patient record (Block 206). In another embodiment, the patient enrollment processor 2114 stores a patient identifier that references patient enrollment information stored in an external system communicatively coupled with the patient monitoring system 2108, such as an external electronic medical record system. After the patient enrollment processor 2114 has stored the patient enrollment information in the new patient record, the patient enrollment processor then prompts the clinician 2102, via the information communication interface 2110, to select an authentication mechanism to associate with the created patient record for allowing secured access to the newly created patient record (Block 208).

Figure 4:
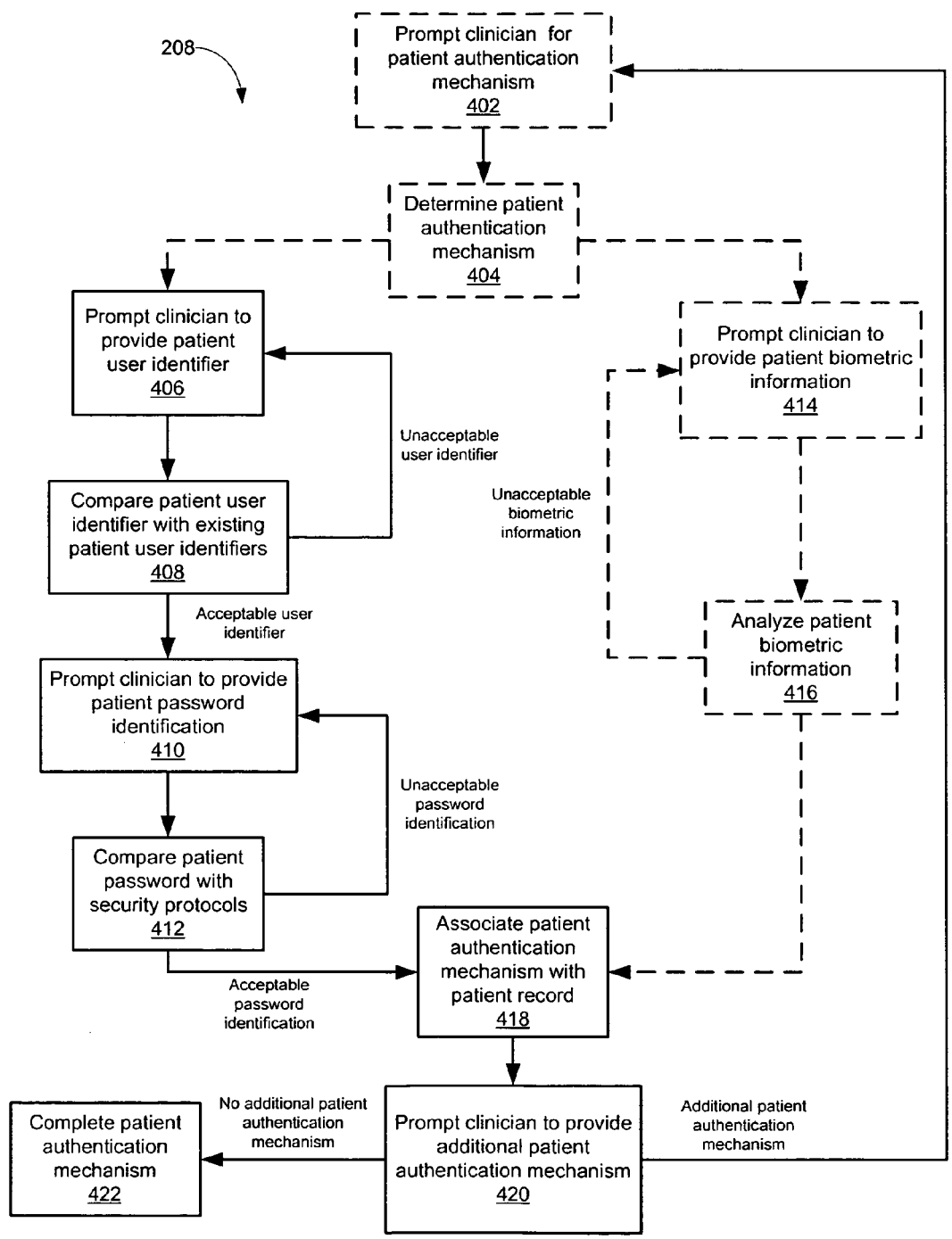
FIG. 4 is a flowchart of one embodiment of associating patient authentication information with a patient record.

FIG. 4 is an example of associating an authentication mechanism with a patient record. In one embodiment of associating an authentication mechanism with a patient record, the information communication interface 2110 prompts the clinician 2102 to select a patient authentication mechanism (Block 402). For example, the information communication interface 2110 may prompt the clinician 2102 to select between multiple authentication mechanisms, such as either a patient user identifier/patient password identification pair or choosing a biometric scheme. If the clinician 2102 is communicating using a telephone, the information communication interface 2110 provides this option over the previously described IVR. However, if the clinician 2102 is communicating with the patient monitoring system 2108 using a computer, the option to choose an authentication mechanism is provided through an Internet web site. Once the clinician 2102 has selected an authentication mechanism to associate with the patient record, the patient enrollment processor 2114 then determines which patient authentication mechanism was chosen (Block 404).

In one example, the clinician 2102 chooses to associate a patient user identifier/patient password identification pair with the patient record. In this example, the information communication interface 2110 prompts the clinician 2102 to first provide a patient user identifier (Block 406), and then communicates the clinician provided patient user identifier to the patient enrollment processor 2114. The patient enrollment processor 2114 may then verify the clinician provided patient user identifier with a list of patient user identifiers retrieved from the patient record database 2116 (Block 408). The patient enrollment processor 2114 may also verify the clinician provided patient user identifier with a list of authorized usernames retrieved from the authorized users database 2134 via the information communication processor 2112. By comparing the clinician provided patient user identifier against the patient user identifiers stored in the patient record database 2116 or the authorized usernames stored in the authorized users database 2134, the patent enrollment processor 2114 can determine whether the clinician 2102 has provided a unique patient identifier for accessing the patient monitoring system 2108. If the patient enrollment processor 2114 determines that the clinician provided patient identifier is not unique, the patient enrollment processor 2114 instructs the information communication interface 2110 to prompt the clinician 2102 to re-provide a patient user identifier (Block 406). If the patient enrollment processor 2114 determines that the clinician provided patient identifier is unique, the patient enrollment processor 2114 instructs the information communication interface 2110 to prompt the clinician 2102 to provide a patient password identification associated with the patient user identifier for accessing the patient monitoring system 2108 (Block 410).

After the clinician 2102 provides a patient password identification of the patient user identifier/patient password identification pair, the patient enrollment processor 2114 compares the patient password identification with a predetermined rule set for complex patient password identification (Block 412). For example, the patient enrollment processor 2114 may have a set of rules that specify that: 1) Every patient password identification must consist of both alphabetic and numeric characters; and 2) Must be longer than five characters. In this example, if the clinician 2102 provides a patient password identification such as "abcde" to the patient enrollment processor 2114 via the information communication interface 2110, the patient enrollment processor 2114 will determine that the clinician provided patient password identification is unacceptable for the established security protocols. To illustrate, and assuming the same set of rules for the security protocol, if the clinician 2102 provides a patient password identification of "12abcd" to the patient enrollment processor 2114 via the information communication interface 2110, the patient enrollment processor 2114 will determine that the clinician provided user identifier is acceptable. Once the patient enrollment processor 2114 has determined that the patient user identifier and the patient password identification are acceptable, the patient enrollment processor 2114 associates the patient user identifier and patient password identification pair with the patient record (Block 418).

When the patient enrollment processor 2114 finishes associating the patient authentication mechanism with the patient record, the patient enrollment processor 2114 then instructs the information communication interface 2110 to prompt the clinician 2102 to select or provide an additional patient authentication mechanism (Block 420). If the clinician 2102 chooses to select or provide an additional patient authentication mechanism, the patient enrollment processor 2114 then proceeds to communicate to the information communication interface 2110 to prompt the clinician to provide or select the desired patient authentication mechanism (Block 402). However, if the clinician 2102 provides a response indicating that the clinician 2102 has decided not to select an additional patient authentication mechanism, the patient enrollment processor 2114 completes the association process (Block 422). For example, the patient enrollment processor 2114 may complete the association process by storing the association between the patient authentication mechanism and the patient record in the patient record database 2116. The patient enrollment processor 2114 may also store the accepted patient user identifier and patient password identification in the authorized users database 2134 via the information communication processor 2112 for future reference. The clinician 2102 may then later provide the accepted patient user identifier and patient password identification to a patient 2104 for accessing the patient monitoring system 2108.

In an alternative embodiment, the clinician provides an additional authentication mechanism for associating with the patient record other than, or in addition to, the patient user identifier and patient password identification authentication mechanism. In this embodiment, the patient enrollment processor 2114 determines that the clinician 2102 wants to associate biometric information with the patient record (Block 404). The patient enrollment processor 2114 then instructs the information communication interface 2110 to prompt the clinician 2102 to provide a patient's biometric information for associating with the patient record (Block 414). The clinician 2102 then provides the biometric information to the patient enrollment processor 2114 via the information communication interface 2110. In one example, the clinician provided biometric information may include data representing the fingerprints of the patient associated with the patient record. In another example, the clinician provided biometric information may include data representing a voice waveform of the patient associated with the patient record. Once the clinician has provided the biometric information to the patient enrollment processor 2114 via the information communication interface 2110, the patient enrollment processor 2114 then analyzes the clinician provided patient biometric information (Block 416).

In analyzing the clinician provided patient biometric information, the patient enrollment processor 2114 may compare the clinician provided patient biometric information with pre-existing patient biometric information stored in the corresponding patient record. Based on the pre-existing patient biometric information, the patient enrollment processor 2114 can then determine that the clinician 2102 did not provide patient biometric information corresponding to the patient associated with the patient record. As an alternative to, or in addition to, the comparison analysis, the patient enrollment processor 2114 may analyze the clinician provided patient biometric information to determine whether the clinician 2102 has provided error-free patient biometric information. For example, the patient enrollment processor 2114 may determine that the clinician provided biometric information is incomplete, such as receiving data indicating four fingerprints rather than five fingerprints, or that an error occurred during transmission using the communication network 2132, such as in the loss of data representing the patient biometric information.

Once the patient enrollment processor 2114 has determined that the clinician provided patient biometric information is acceptable, the patient enrollment processor 2114 associates the clinician provided patient biometric information with the patient record (Block 418).

After the patient enrollment processor 2114 has finished associating the clinician provided patient biometric information with the patient record, the patient enrollment processor 2114 communicates to the information communication interface 2110 to prompt the clinician 2102 to select or provide an additional patient authentication mechanism (Block 420). If the clinician 2102 chooses to select or provide an additional patient authentication mechanism, the patient enrollment processor 2114 then instructs the information communication interface 2110 to prompt the clinician 2102 to provide or select the desired patient authentication mechanism (Block 402). However, if the clinician 2102 provides a response indicating that the clinician 2102 has decided not to select an additional patient authentication mechanism, the patient enrollment processor 2114 completes the association process (Block 422). For example, this may involve storing the association between the patient authentication mechanism and the patient record in the patient record database 2116. The patient enrollment processor 2114 may also store the accepted clinician provided patient biometric information in the authorized users database 2134 via the information communication processor 2112 for future reference. The clinician 2102 may then later provide or describe the patient biometric information to a patient 2104 for accessing the patient monitoring system 2108.

In another embodiment, the patient enrollment processor 2114 allows the clinician 2102 to supplement or replace the current authentication mechanism associated with a patient record with a later authentication mechanism. For example, the clinician 2102 may decide to later replace the patient user identifier/patient password identification authentication mechanism with the clinician provided biometric authentication mechanism, such as with data representing the associated patient's fingerprints.

Referring back to FIG. 2, after the clinician 2102 has associated an authentication mechanism with a patient record, the patient enrollment processor 2114 then proceeds to allow the clinician 2102 to select one or more questionnaires from the patient questionnaire database 2118 for the patient associated with the created patient record (Block 210). In one embodiment, the patient questionnaires include several pre-defined questionnaires for specific chronic diseases, such as congestive heart failure, diabetes, asthma or anticoagulation monitoring. Each of the questionnaires may be generated in advance of a given patient session and may be designed to collect specific clinical information from the patient. Each of the questionnaires may further include one or more questions. The questionnaires may include a pre-defined static script of one or more questions designed to elicit particular response from the patient with respect to a particular chronic disease that the clinician is trying to manage, or directed to other subject matter such as the collection of biographical data. For example, all of the questions from the script may be presented to the patient in a linear fashion. In another example, these scripts include simple branching logic allowing the patient monitoring system 2108 to select and present one or more subsequent questions from the pre-defined script based upon the answer to a prior question from the pre-defined script received during the patient session.

As explained below in reference to FIG. 5, once the clinician 2102 has selected one or more questionnaires for the patient record, the patient enrollment processor 2114 then communicates to the information communication 2110 to prompt the clinician 2102 whether the clinician 2102 wants to modify the selected one or more questionnaires (Block 212), such as by adding questions, deleting questions and/or modifying questions. If the clinician elects to modify the selected one or more questionnaires, the patient enrollment processor proceeds to modify the patient questionnaire (Block 214) as directed by the clinician 2102. Alternatively, the patient enrollment processor 2114 may directly proceed to associating the selected one or more questionnaires if the clinician 2102 chooses not to modify the selected one or more questionnaires (Block 216). After the clinician 2102 has finished modifying the selected questionnaire, the patient enrollment processor 2114 then associates the selected questionnaires with the patient record (Block 216). For example, the patient enrollment processor 2114 may store the patient questionnaires as part of the patient record stored in the patient record database 2116. However, the patient enrollment processor 2114 could also create a new record in the patient questionnaire database 2118 representing the selected one or more questionnaires and their (or its) association with the patient record stored in the patient record database 2116.

In one embodiment, the patient questionnaire database 2118 is a software-implemented database residing in the same computer system as the information communication processor 2112. In another embodiment, the patient questionnaire database 2118 is a series of files logically arranged in an operating system, such that each file represents an individual patient record. In yet a further embodiment, the patient questionnaire database 2118 resides on a separate computer system, wherein the computer system has its own internal processor (such as an x86-based processor or RISC processor), memory (including both RAM and internal storage devices), input devices (such as a keyboard, microphone, and mouse) and output devices (such as a visual display device and an audio display device), and is coupled with the patient enrollment processor 2114 using a network technology such as Ethernet, 802.11 a/b/g, Bluetooth, or combinations thereof.

Figure 5:
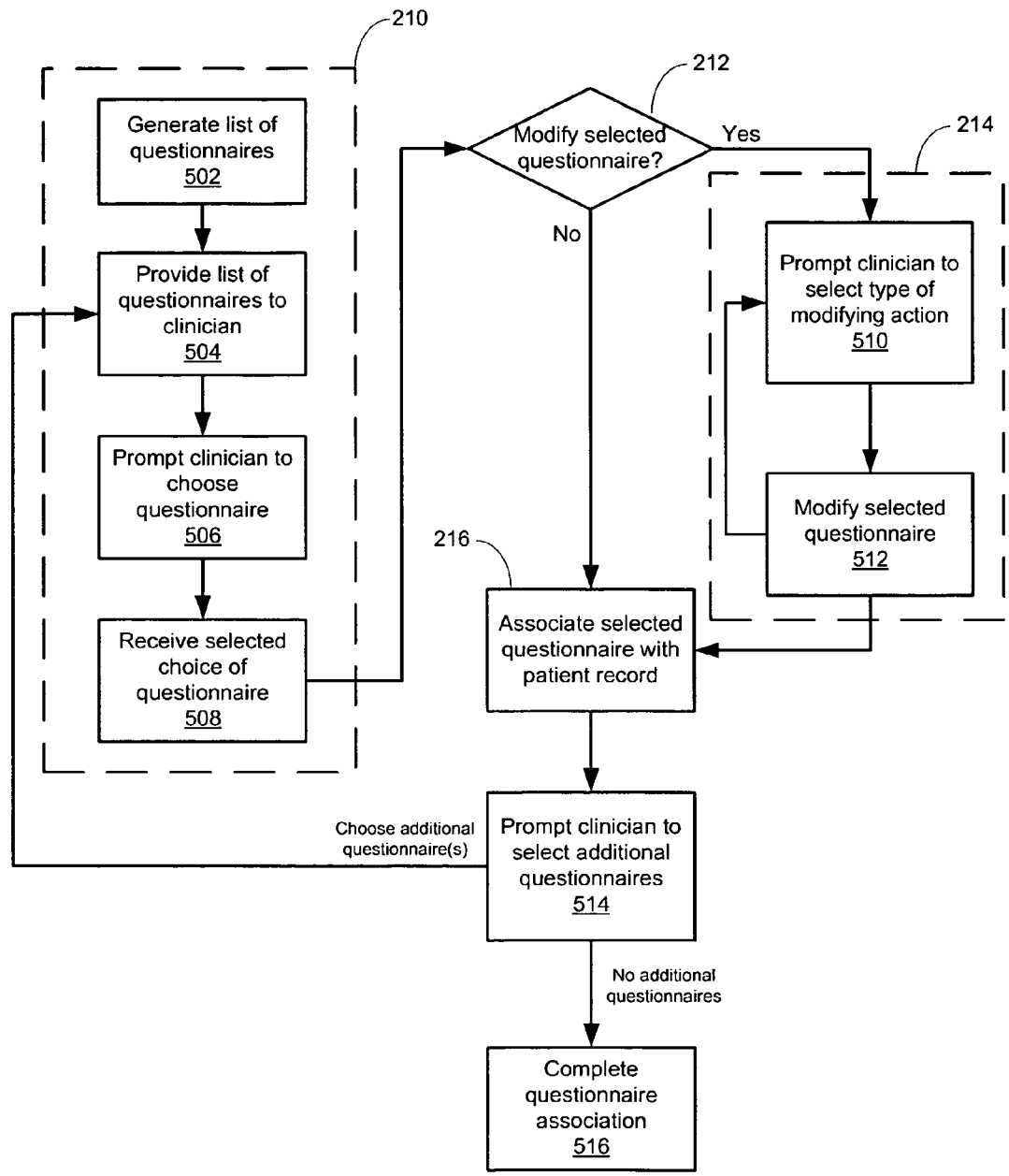
FIG. 5 is a flowchart of one embodiment of selecting and modifying a patient questionnaire.

FIG. 5 illustrates one example of selecting and modifying a patient questionnaire. After the patient enrollment processor 2114 finishes creating a patient record and associating an authentication mechanism with the patient record, the patient enrollment processor 2114 generates a list of all available questionnaires (Block 502). The patient enrollment processor 2114 may generate the list of all available questionnaires by accessing the patient questionnaire database 2118. For example, each record in the patient questionnaire database 2118 may represent an individual questionnaire and the patient enrollment processor 2114 may access each record to generate a list of all available questionnaires. Alternatively, one record in the patient questionnaire database 2118 may represent all the available questionnaires and the patient enrollment processor 2116 could generate the list of all available questionnaires by accessing the patient questionnaire database 2118 and retrieving that one record.

After the patient enrollment processor 2114 generates the list of all available questionnaires, the patient enrollment processor 2114 then provides the questionnaire list to the clinician 2102 via the information communication interface 2110 (Block 504). Providing the questionnaire list to the clinician 2102 may include audibly reciting each available questionnaire to the clinician 2102, visually displaying each available questionnaire to the clinician 2102, or combinations thereof. For example, if the clinician 2102 accessed the patient monitoring system 2108 using a telephone, the clinician 2102 would be provided with an audible recording that recites each available questionnaire based on the list of questionnaires generated by the patient enrollment processor 2114. In another example, if the clinician 2102 accessed the patient monitoring system 2108 using a computer, the clinician 2102 would be provided with an Internet web site that lists each available questionnaire based on the list of questionnaires generated by the patient enrollment processor 2114. An option representing each available questionnaire may be presented to the clinician 2102 simultaneously or the clinician 2102 might have to review each option individually before proceeding to the next option.

Once the patent enrollment processor 2114 provides the list of questionnaires to the clinician 2102, the patient enrollment processor 2114 then instructs the information communication interface 2110 to prompt the clinician 2102 to choose a questionnaire (Block 506). The information communication interface 2110 then receives the clinician's 2102 choice of the selected questionnaire (Block 508). After receiving the clinician's choice of selected questionnaire, the patient enrollment processor 2114 then instructs the information communication interface 2110 to prompt the clinician 2102 whether the clinician 2102 wants to modify the selected questionnaire (Block 212).

Where the clinician 2102 elects to modify the selected questionnaire, the patient enrollment processor 2114 then instructs the information communication interface 2110 to prompt the clinician 2102 to select a type of modifying action to perform on the selected questionnaire (Block 510). Modifying actions include deleting or replacing a particular question on the selected questionnaire or altering a particular question on the selected questionnaire. Modifying actions may also include a tailoring process to tailor a selected questionnaire for the patient associated with the patient record.

Once the clinician 2102 has chosen the modifying action to perform on the selected questionnaire, the clinician 2102 provides that response to the patient enrollment processor 2114 via the information communication interface 2110. When the patient enrollment processor 2114 receives the clinician's choice of modifying action, the patient enrollment processor 2114 then modifies the selected questionnaire according to that modifying action. (Block 512). After the patient enrollment processor 2114 has modified the selected questionnaire according to the clinician selected modifying action, the patient enrollment processor 2114 may instruct the information communication interface 2110 to prompt the clinician 2102 whether the clinician 2102 wants to select an additional modifying action or wants to associate the selected questionnaire as modified, with the patient record. If the clinician 2102 provides a response indicating that the clinician 2102 wants to further modify the selected questionnaire, the patient enrollment processor 2114 may re-present a list of possible modifying actions and prompt the clinician 2102 to select a modifying action via the information communication interface 2110 (Block 510). However, the clinician 2102 could also provide a response indicating that the clinician 2102 is satisfied with the questionnaire and wants to associate the selected questionnaire with the patient record.

If the clinician 2102 provides a response indicating that the clinician 2102 wants to associate the selected questionnaire with the patient record, the patient enrollment processor 2114 associates the selected questionnaire with the patient record (Block 216). For example, the patient enrollment processor 2114 may store the patient questionnaire, or a pointer thereto, as part of the patient record stored in the patient record database 2116. Alternatively, the patient enrollment processor 2114 may create a new record in the patient questionnaire database 2118 representing the selected questionnaire and its association with the patient record stored in the patient record database 2116.

After the patient enrollment processor 2114 associates the selected questionnaire with the patient record, the patient enrollment processor 2114 then instructs the information communication interface 2110 to prompt the clinician 2102 as to whether the clinician 2102 wants to associate additional questionnaires with the patient record (Block 514). Where the clinician 2102 provides a response indicating that the clinician 2102 wants to select additional questionnaires, the patient enrollment processor 2114 then provides a list of available questionnaires to the clinician 2102 (Block 504). Where the clinician 2102 provides a response indicating that the clinician 2102 does not want to select additional questionnaires, the patient enrollment processor 2114 completes the questionnaire association (Block 516). As an example of completing the questionnaire association, the patient enrollment processor 2114 may proceed through a verification process to ensure that the clinician 2102 does not want to further associate questionnaires with the patient record. In another embodiment, the patient enrollment processor 2114 reviews the selected questionnaires and their modifications (if any) with the clinician 2102 before proceeding further. Completing the questionnaire association could also include another verification process to ensure that the modifying actions performed on the selected questionnaires were correct and accurate or confirming that the clinician 2102 does not want to further modify the selected questionnaires.

Referring back to FIG. 2, after associating the selected one or more questionnaires with the patient record, the patient enrollment processor 2114 completes the enrollment process (Block 218). In completing the enrollment process, the patient enrollment processor 2114 may communicate with the clinician 2102 via the information communication interface 2110 to review any one of the proceeding actions. For example, the patient enrollment processor 2114 could give the clinician 2102 the opportunity to review the accuracy of the provided patient enrollment information. The patient enrollment processor 2114 could also give the clinician 2102 the opportunity to review, or change, the associated authentication mechanism with the patient record, or allow the clinician 2102 to replace, or supplement, the associated authentication mechanism with another or similar authentication mechanism. The patient enrollment processor 2114 could further allow the clinician 2102 to review the selected questionnaires and select additional questionnaires for associating with the patient record. The patient enrollment processor 2114 could additionally allow the clinician 2102 to return to any point in the enrollment process by providing such option to the clinician 2102 via the information communication interface 2110. For example, the information communication interface 2110 could provide a list of points in the enrollment process to the clinician 2102 as an audible menu, visual list, or a combination thereof.

Referring to FIG. 1, where the clinician 2102 provides a response that the clinician 2102 is finished with the enrollment process, the patient enrollment processor 2114 then instructs the information communication interface 2110 to prompt the clinician 2102 whether the clinician 2102 wants to enroll another patient in the patient monitoring system 2108 (Block 116). Where the clinician 2102 provides a response indicating that the clinician 2102 wants to enroll another patient, the patient enrollment processor 2114 proceeds to re-start the enrollment process (Block 114). Where the clinician 2102 provides a response indicating that the clinician is finished enrolling patients in the patient monitoring system 2108, the patient enrollment processor 2114 finishes the clinician session with the clinician 2102 (Block 122). In finishing the clinician session with the clinician 2102, the patient enrollment processor 2114 may review all of the enrollment actions the clinician 2102 has taken during the immediate session. The patient enrollment processor 2114 could also provide an option for the clinician 2102 to review all of the previous enrollment sessions (if any), and the actions taken during those previous enrollment sessions (if any). The patient enrollment processor 2114 could also verify the actions taken by the clinician 2102 during the immediate clinician session and whether the clinician 2102 wants to modify any (or all) of the actions taken during the immediate clinician session. Once the clinician 2102 indicates that the clinician 2102 is satisfied with the enrollment process for the one or more patients, the patient enrollment processor 2114 terminates the session between the clinician 2102 and the patient monitoring system 2108.

Figure 24:
FIG. 24 is one example of a patient enrollment report.

After enrolling one or more patients in the patient monitoring system 2108, the clinician 2102 may request to view reports of the enrolled patients. The clinician 2102 may also view reports of the enrolled patients in a later session between the clinician 2102 and the patient monitoring system 2108. FIG. 24 shows one example of a patient enrollment report.

Figure 6:
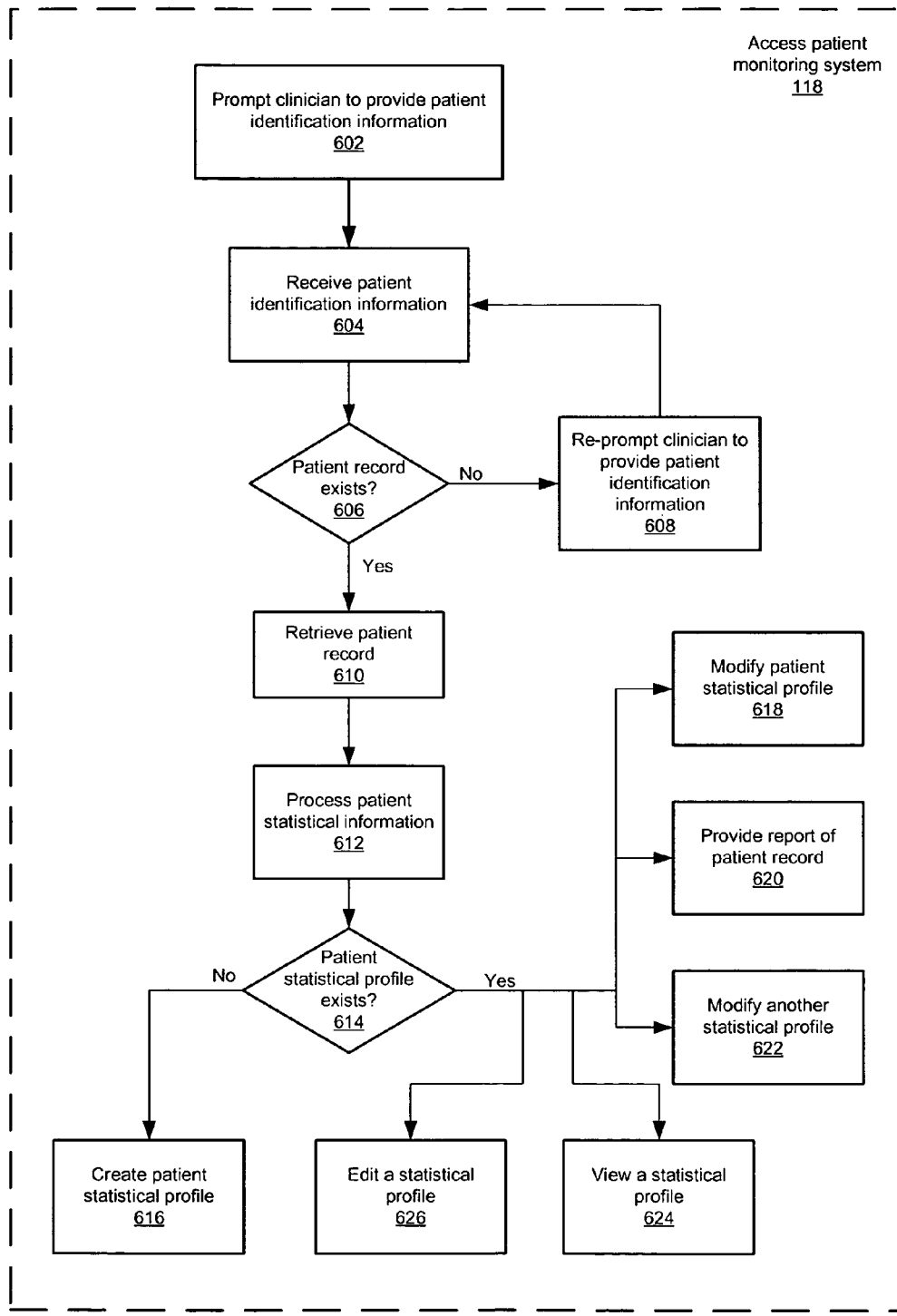
FIG. 6 is a flowchart of one embodiment of accessing the patient monitoring system.

Instead of providing a response indicating that the clinician wants to enroll a new patient, the clinician could provide a response that the clinician wants to access the patient monitoring system (Block 118). Referring to FIG. 6, where the clinician 2102 provides a response that the clinician 2102 wants to access the patient monitoring system, the patient monitoring processor 2120 then communicates with the information communication interface 2110 via the information communication processor 2112 to prompt the clinician 2102 to provide patient identification information (Block 602), as was specified in the enrollment process (described above). The patient identification information may be a personal identification number, biometric information, demographic information, a patient user identifier and patient password identification, or combinations thereof.

Once the patient monitoring processor 2120 has received the patient identification information (Block 604), the patient monitoring processor 2120 then determines whether the patient associated with the patient identification information has a patient record with the patient monitoring system 2108 (Block 606). For example, the patient monitoring processor 2120 may communicate with the patient record database 2116 to determine whether the patient associated with the patient identification information has a patient record stored in the patient record database 2116. e.g. retrieve any records associated with the patient identification information.

If the patient monitoring processor 2120 determines that a patient record for the patient associated with the patient identification information does not exist in the patient record database 2116, the patient monitoring processor 2120 may communicate an error to the clinician 2102 that the patient record does not exist for that particular patient, or the patient monitoring processor 2120 may re-prompt the clinician to provide the patient identification information (Block 608). Where the patient monitoring processor 2120 determines that the patient associated with the patient identification information has a patient record in the patient record database 2116, the patient monitoring processor 2120 then requests access to or retrieves that patient record (Block 610). Retrieving the patient record may include the patient record database 2116 providing a copy of the patient record, authorizing the patient monitoring processor 2120 to access the patient record, or it may include the patient record database 2116 creating a temporary patient record locally accessible by the patient monitoring processor 2120. Other types of retrieval may also be possible, such as creating a duplicate copy of the patient record for the patient monitoring processor 2120. The patient monitoring processor 2120 may further inform the clinician 2102 that the patient associated with the patient identification information has a patient record with the patient monitoring system 2108.

After the patient monitoring processor 2120 has determined that a patient record exists for the patient associated with the patient identification information and the patient monitoring processor 2120 has retrieved the patient record, the patient monitoring processor 2120 then processes patient statistical information (Block 612), explained below.

The patient statistical information, which may be provided by the clinician 2102, or alternatively, by the external data source 2106, may include empirical data, metrics, probabilities and/or statistics regarding the patient 2104 and/or a population which may include the patient 2104. For example, the patient statistical information may include personal identifiers, information for linking to other information systems, demographics, occupational history and exposures, educational history, sports and exercise history, diagnostic images and their associated interpretations, personal and family health history, current and past medications, current and past behavioral interventions and the patient's experiences with those treatments, current and past test results, allergies, psychological profile and compliance information, electronic medical records of varying format, or combinations thereof. The patient statistical information may also include information on past and current diagnoses and probable diagnoses, possible treatments and behaviors to modify, how others have responded to those treatments and modifications, and the personal characteristics of those patients.

Figure 7:
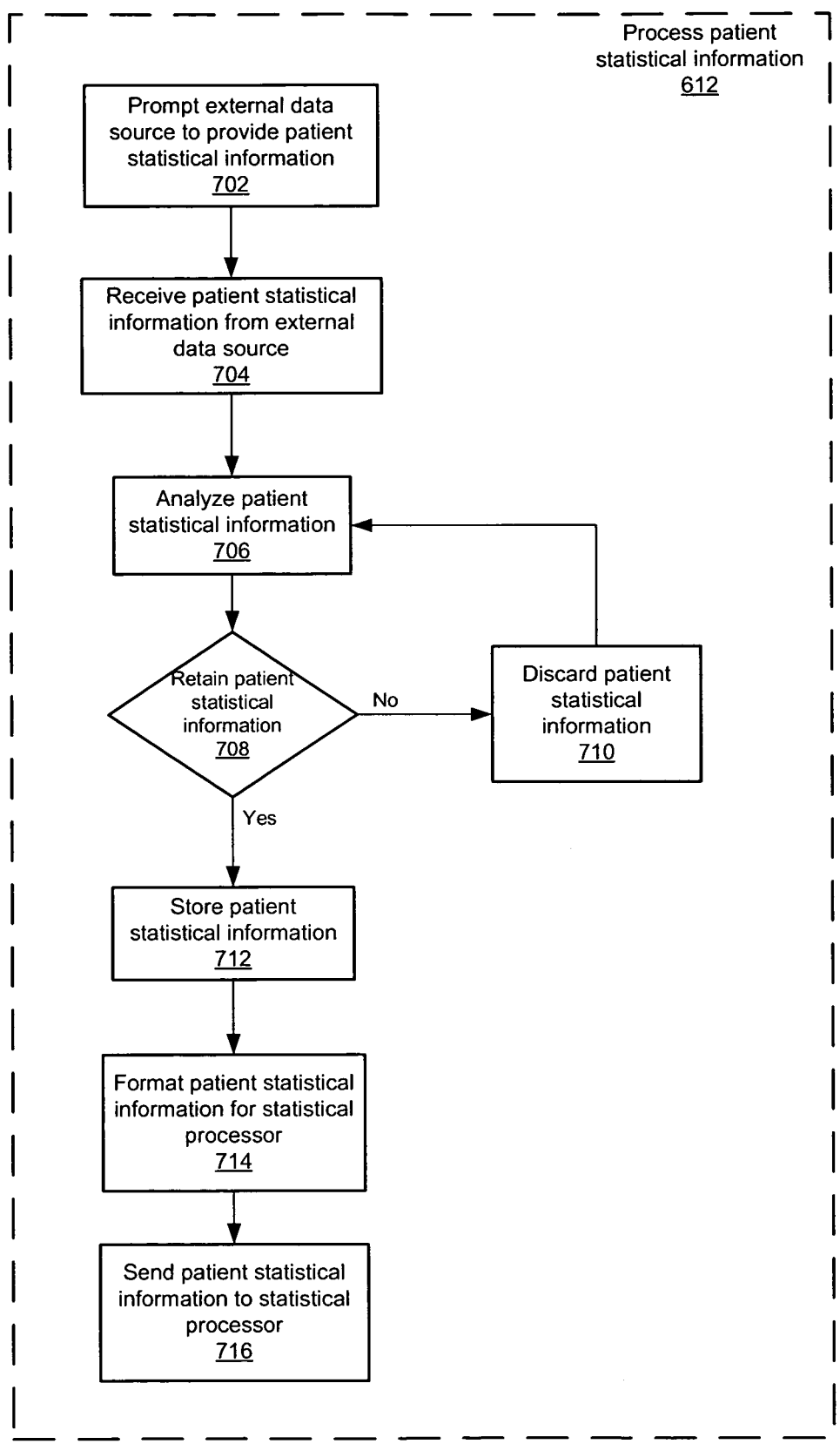
FIG. 7 is a flowchart of one embodiment of processing patient statistical information.

FIG. 7 is a flowchart showing the operations of processing patient statistical information according to one embodiment. Where the patient monitoring processor 2120 determines that a patient statistical profile does not exist for the patient associated with the retrieved patient record, the patient monitoring processor 2120 then prompts the clinician 2102 to provide patient statistical information for the patient (Block 702). Alternatively, at least a portion of the patient statistical information may be derived from the appropriate population statistical profile. In an alternative example, the patient monitoring processor 2120 prompts an external data source 2106, such as hospital or other organization, to provide the patient statistical information. In a further example, the external data source could be an automated computer program or other medical device, such as a glucometer, thermometer, etc., in communication with the patient monitoring processor 2120. In yet a further embodiment, the external data source could provide patient statistical information to the patient monitoring processor 2120 at scheduled intervals, random intervals, after completing one or more specified tasks, such as taking a blood sample, or combinations thereof.

After the patient monitoring processor 2120 prompts the clinician 2102, or alternatively, the external data source 2106, to provide the patient statistical information, the patient monitoring processor 2120 then receives the patient statistical information, defined below (Block 704).

In another embodiment, where the patient statistical profile does not exist for a patient record, an external data source 2106 initiates communications with the patient monitoring system 2108 to provide patient statistical information or the patient statistical profile. For example, the external data source 2106 could be a separate hospital or other institution that maintains a database of patient statistical information and may provide the patient statistical information to the patient monitoring system 2108. The hospital or other institution could provide the patient statistical information on a predetermined basis, on a dynamic basis, such as where updated or new patient statistical information is provided to the hospital or other institution, or combinations thereof. In another example, the external data source 2106 could be an automated computer program or medical device in communication with the patient monitoring system 2108 and may provide the patient statistical information to the patient monitoring system 2108 on a predetermined basis, a dynamic basis, or combination thereof.

Where the clinician 2102 communicates with the patient monitoring processor 2120 using the IVR interface, the IVR interface may present audible options to the clinician 2120 for the clinician 2120 to select in providing the patient statistical information to the patient monitoring processor 2120. For example, the clinician 2120 could use the keypad of the telephone in communicating with the IVR interface to provide choices as patient statistical information to the patient monitoring processor 2120. In the alternative, the clinician 2120 could provide audible responses to the audible options of the IVR interface as patient statistical information. The patient monitoring processor 2120 could then analyze the received audible responses to generate the patient statistical information for the patient record.

In providing the patient statistical information to the patient monitoring processor 2120, the clinician 2102 could also use a computer to provide that information. In one embodiment, the clinician 2102 communicates with the patient monitoring processor 2120 using an Internet web site as an interface, and the clinician 2102 provides the patient statistical information to the patient monitoring processor 2120 using that Internet web site. For example, the Internet web site may allow the clinician 2102 to select and submit various pre-defined parameters/options, such as from a bulleted list, drop-down menu, or other input-related field, to the patient monitoring processor 2120, which can use those submitted options directly as the patient statistical information or can use those submitted options to generate the patient statistical information. In another alternative, the Internet web site may allow the clinician 2102 to send the patient statistical information in a file format, such as a Microsoft® Excel® spreadsheet, that is recognizable by the patient monitoring processor 2120.

As previously discussed above, one or more actor may provide some or all of the patient statistical information, and the one or more actor may take on one or more role in providing this patient statistical information. For example, while the patient 2104 is an "actor" that can access the patient monitoring system 2108, the patient 2104 can also act within the "role" as a clinician 2102 or external data source 2106. Similarly, the external data source 2106 or the clinician 2102 may act within the role of the patient 2104. Other combinations of the "actors" clinician 2102, the patient 2104, and the external data source 2106 acting within the "roles" of clinician 2102, the patient 2104, and the external data source 2106 are also possible. Hence, the provided patient statistical information may be provided by the clinician 2102, the patient 2104, or the external data source 2106, or a combination thereof, acting within the "role" of the clinician 2102, the patient 2104, or the external data source 2106. Similarly, other actors not explicitly shown, such as a surrogate authorized by the patient or the clinician, or a health management organization authorized by the patient or clinician, may take on the "role" of the clinician 2102, the patient 2104, the external data source 2106, or combination thereof. Hence, third-parties may also provide the patient statistical information acting within the "role" of the clinician 2102, the patient 2104, the external data source 2106, or combinations thereof.

After the patient monitoring processor 2120 has received the patient statistical information, the patient monitoring processor 2120 then analyzes the patient statistical information (Block 706). The patient monitoring processor 2120 may be pre-configured to analyze the patient statistical information for specific anomalies, or the patient monitoring processor 2120 may be configured to determine the accuracy and/or validity of the received patient statistical information. For example, the patient monitoring processor 2120 may be configured with a rule set that determines how to analyze the patient statistical information, and the patient statistical information may conform to the rules of the rule set. In one embodiment, the rule set may specify that the patient statistical information must contain at least the patient gender and age.

In another embodiment, the rule set may specify that the patient statistical information cannot contain information that would identify the patient associated with the patient statistical information, such as the patient's name or patient's Social Security number. The patient monitoring processor 2120 may analyze the patient statistical information as it is provided in real-time or, alternatively, the patient monitoring processor 2120 could analyze the patient statistical information after it has been received in its entirety by the patient monitoring processor 2120. In another embodiment the patient monitoring processor 2120 may solicit information on the patient or related possible treatments by a human- or machine-based search methodology, which provides updated information as it is discovered. In this embodiment, updates to the analyses would be triggered by the modification or addition of information to the patient statistical information. In yet an alternative embodiment, the information provided to the patient monitoring processor 2120 is provided a real-time basis, such that the patient monitoring processor 2120 receives the information during a procedure, treatment, or other similar tasks. In another embodiment, the information provided to the patient monitoring system 2120 is provided on a batch basis, such that the patient monitoring processor 2120 receives information based on a group of procedures, treatment, other similar tasks, performed. In this embodiment, the batch information provided to the patient monitoring processor 2120 may be sent based on a predetermined number of procedures, treatments, or other similar tasks performed, or may be sent after a predetermined amount of time, such as months, weeks, days, other measurements of time, or combinations thereof, has elapsed.

As the patient monitoring processor 2120 is analyzing the provided patient statistical information, the patient monitoring processor 2120 determines whether to retain the patient statistical information being analyzed (Block 708). For example, the patient monitoring processor 2120 may analyze the patient's name as part of the provided patient statistical information, such as to ensure the name is spelled correctly or corresponds to a patient record. The patient monitoring processor 2120 may be configured to reject any patient's name provided with the patient statistical information. If the patient monitoring processor 2120 is configured to reject this type of information, the patient monitoring processor 2120 will then discard or disregard that information (Block 710). The patient monitoring processor 2120 then proceeds to analyze the next part or portion of the patient statistical information.

Alternatively, the patient monitoring processor 2120 may be configured to retain certain types of patient statistical information. For example, the patient monitoring processor 2120 may be configured to retain the type of behavior submitted with the patient statistical information. If the patient monitoring processor 2120 is configured to retain this information, the patient monitoring processor 2120 then proceeds to the next part or portion of the statistical patient information. In another embodiment, the patient monitoring processor 2120 analyzes all of the provided patient statistical information in one iteration and retains only that information that the patient monitoring processor 2120 is configured to retain. Once the patient monitoring processor 2120 has finished analyzing all of the information of the patient statistical information, the patient monitoring processor then proceeds to store the patient statistical information (Block 712).

In storing the patient statistical information, the patient monitoring processor 2120 may store the patient statistical information in the patient record database 2116. For example, the patient monitoring processor 2120 may modify the patient record associated with the patient identification information provided by the clinician 2102 to store the patient statistical information. Alternatively, the patient monitoring processor 2120 creates a new record in the patient record database 2116 for storing the patient statistical information. In yet another example, the patient monitoring processor 2120 stores the patient statistical information in the statistical profile database 2130 and associates that patient statistical information with the patient record in the patient record database 2116. In a further example, the patient monitoring processor 2120 creates a temporary storage location, such as in local memory coupled with the patient monitoring processor 2120, to store the patient statistical information.

Once the patient monitoring processor 2120 has stored the patient statistical information, the patient monitoring processor 2120 then formats the patient statistical information for the patient statistical processor 2122 (Block 714). Formatting the patient statistical information for the patient statistical processor 2122 may also occur before the patient monitoring processor 2120 has stored the patient statistical information. Formatting the patient statistical information for the statistical processor 2122 may require that the patient statistical information is arranged according to a specification associated with the statistical processor 2122, such as arranging the stored patient statistical information as comma-delimited text file. Formatting the patient statistical information for the statistical processor 2122 may also involve converting the stored patient statistical information from one computer-file format to another computer-file format, such as converting a standard text (TXT) file to an Extensible Markup Language (XML) file, Hypertext Markup Language (HTML) file, Microsoft® Excel® (XLS) file, MacBinary (BIN) file or other computer-readable file. After the patient statistical information is formatted for the statistical processor 2122, the patient monitoring processor 2120 sends the patient statistical information to the statistical processor 2122 (Block 716).

Figure 8:
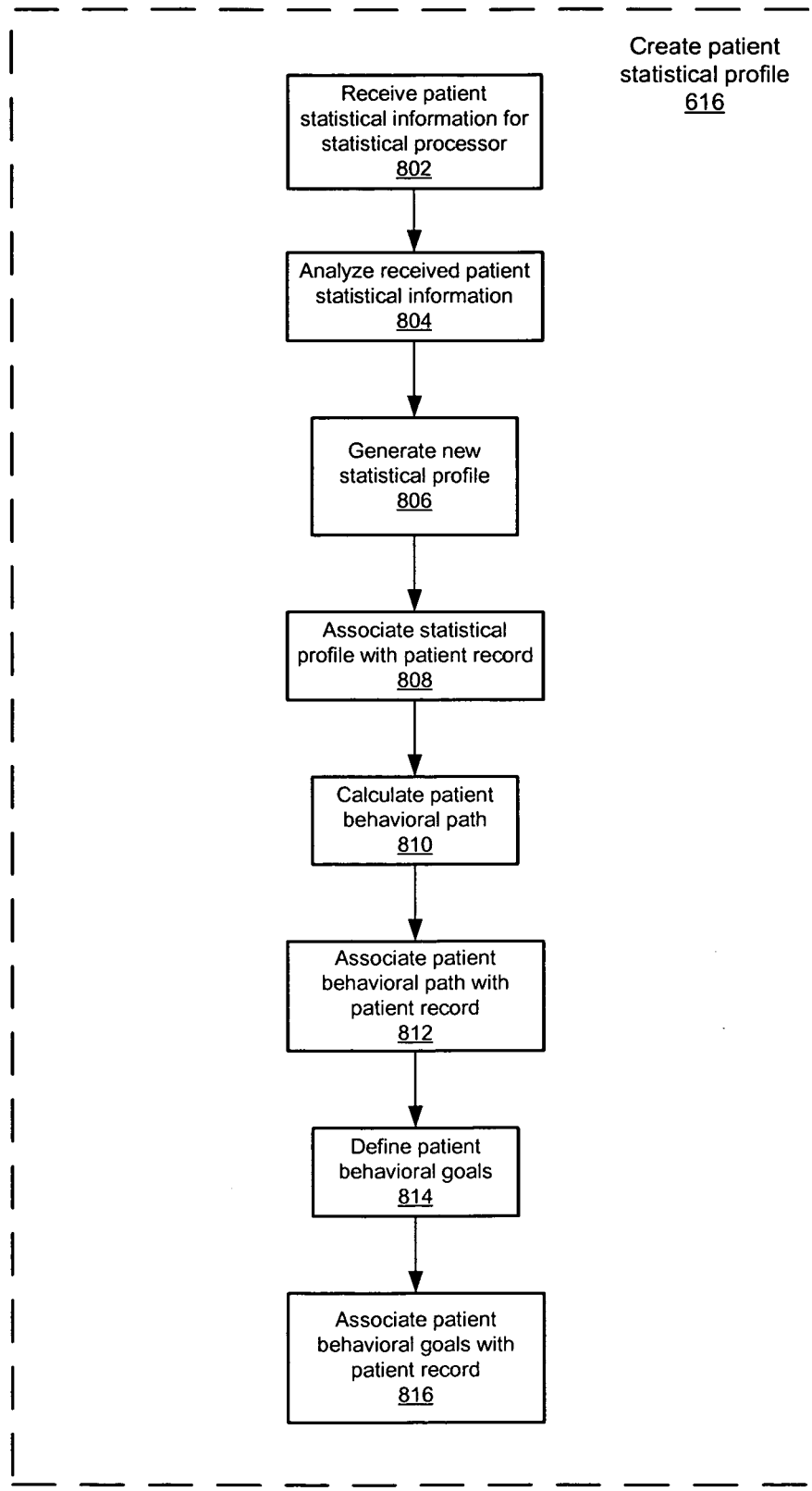
FIG. 8 is a flowchart of one embodiment of creating a patient statistical profile.

Referring back to FIG. 6, after processing the patient statistical information (Block 612), the patient monitoring processor 2120 then determines whether a patient statistical profile exists for or is associated with the patient record (Block 614). If the patient monitoring processor 2120 determines that a patient statistical profile is not associated with the patient record, the patient monitoring processor 2120 then proceeds to process patient statistical information from the clinician (Block 612) to create a new patient statistical profile (Block 616). FIG. 8 is a flowchart depicting the operation of creating a patient statistical profile according to one embodiment.

As shown in FIG. 8, the statistical processor 2122 receives the patient statistical information from the patient monitoring processor 2120 (Block 802). The statistical processor 2122 then analyzes the patient statistical information (Block 804). Analyzing the patient statistical information may include checking the patient statistical information for errors, assigning values to variables of the statistical profile, transforming or translating one or more parts of the patient statistical information or ensuring that the patient statistical information is in a format understood by the statistical processor 2122. In one embodiment, the statistical processor 2122 sends an error to the patient monitoring processor 2120 to indicate an error in the statistical information, such as not being in the correct format or not having enough statistical information to generate a statistical profile. In another embodiment the statistical processor 2122 sends an acknowledgment to the patient monitoring processor 2120 indicating that the statistical processor 2122 can generate a statistical profile based on the provided statistical information.

After analyzing the statistical information, the statistical processor 2122 then generates a new statistical profile for the patient (Block 806). Generating a new statistical profile may include processing the statistical information to obtain a statistical profile that matches the patient. For example, the statistical processor 2122 could analyze the patient record from the patient record database 2116 and compare the information in the patient record with the received statistical information. In one embodiment, the statistical processor 2122 generates a statistical profile based on a comparison of the patient information with the statistical information. In another embodiment, the statistical processor 2122 analyzes previously stored statistical profiles 2130 to determine whether a new statistical profile is needed. For example, the statistical processor 2122 may determine that a new statistical profile based on the provided statistical information is not needed when compared with the pre-existing statistical profiles. In yet a further embodiment, the statistical processor 2122 refers to a population statistical profile stored in the statistical profiles 2130 to generate the patient statistical profile. For example, the statistical processor 2122 may use the population statistical profile as the patient statistical profile. In another example, the statistical processor 2122 may use the provided patient statistical information in conjunction with the population statistical profile to generate the patient statistical profile. In yet another embodiment, the statistical processor 2122 generates an empty patient statistical profile without referring to either the provided patient statistical information or the stored statistical profiles 2130.

After the statistical processor 2122 has generated a patient statistical profile (Block 806), the statistical processor 2122 then associates the patient statistical profile with the patient's record based on the previously provided a patient identification information (Block 808). In one embodiment, the statistical processor 2122 creates a logical relationship between the patient record in the patient record database 2116 and a stored statistical profile 2130, such as either a patient statistical profile or a population statistical profile. In another embodiment, the statistical processor 2122 modifies the patient record stored in the patient record database 2116 to incorporate the statistical profile. In yet a further embodiment, the statistical processor 2122 modifies a statistical profile to reflect the association between the modified statistical profile and the patient record stored in the patient record database 2116.

Once the statistical processor 2122 finishes associating the patient statistical profile with the patient record (Block 808), the statistical processor 2122 proceeds to communicate with the patient behavioral calculator 2124 to calculate a patient behavioral path, described in more detail below, for the associated patient statistical profile (Block 810). In one embodiment, the patient behavioral calculator 2124 is software residing on a storage device coupled with the patient monitoring processor 2120 in the statistical processor 2122.

The patient behavioral path calculated by the patient's behavioral calculator 2124 is a measure or scale used by the patient monitoring system 2108 to determine/gauge the progress of the patient in reaching a patient behavioral goal and/or objective. There may zero, one, or more than one patient behavioral goals in achieving a behavioral objective. A behavioral goal may also be a behavioral objective. For example, the patient behavioral path may include a schedule for the patient to receive a particular treatment or to perform a particular task. The patient's behavioral path may initially include information based on either the patient statistical profile, a population statistical profile, or combinations thereof, such as the frequency to administer treatments or the types of treatments to administer. The patient behavioral calculator 2124 may calculate the patient behavioral path based on the associated patient statistical profile, a population statistical profile, the provided patient statistical information, the patient information from the patient record database 2116, or a combination thereof. For example, the patient behavioral calculator 2124 may communicate with the statistical processor 2122 and the patient monitoring processor 2120 to calculate a new patient behavioral path. In another example, the patient behavior calculator 2124 retrieves the statistical profile associated with the patient record to calculate a new patient behavioral path.

After calculating the patient behavioral path (Block 810), the patient behavioral calculator 2124 then associates the calculated behavioral path with the patient record based on the clinician provided patient identification information (Block 812). In one embodiment, the patient behavioral calculator 2124 modifies the associated statistical profile to incorporate the calculated patient behavioral path. In another embodiment, the behavioral calculator 2124 modifies a patient statistical profile, a population statistical profile, or combination thereof, to reflect the association between the modified statistical profile and the patient record stored in the patient record database 2116. In yet another embodiment, the behavioral calculator 2124 stores the patient behavioral path in the patient record database 2116. Alternatively, the behavioral calculator 2124 could store the patient behavioral path in the statistical profiles 2130, another storage medium, or combinations thereof. Examples of storage mediums include hard drives, flash drives, tape drives, random access memory, EEPROMs, optical media (CD+/−R, DVD+/−R, Blu-ray, HD-DVD, etc.), or combinations thereof.

After the patient behavioral calculator 2124 associates a patient behavioral path with the patient record (Block 812), the patient behavioral calculator 2124, where applicable, may optionally define one or more intermediate patient behavioral goals along the patient behavioral path to achieve the patient behavioral objective (Block 814). In one embodiment, the intermediate patient behavioral goals are a sequential series of goals, each of which may be achieved before proceeding to the next subsequent goal. The patient intermediate behavioral goals may further be based on, or alternatively, independent of, the one or more statistical profiles associated with the patient record. Each of the intermediate patient behavioral goals may be defined along the patient behavioral path, may lay outside the patient behavioral path, or a combination thereof. For example, a patient may be required to achieve one goal, such as to stop smoking five cigarettes for a day, before proceeding to the next goal, such as stop smoking cigarettes completely for the entire day. In one embodiment, the intermediate patient behavioral goals are calculated to assist the patient in achieving the patient behavioral objective. In another embodiment, the patient's intermediate behavioral goals are calculated independently, such that each intermediate behavioral goal is based on achieving the previous intermediate behavioral goal. The patient behavior calculator 2124 may define a patient behavioral goal as the patient behavioral objective, as an intermediate patient behavioral goal, or as a combination thereof.

After the patient behavioral calculator 2124 has defined the one or more patient behavioral goals (Block 814), the patient behavioral calculator 2124 then associates the one or more patient behavioral goals with the patient record (Block 816). In one embodiment, the patient behavioral calculator 2124 modifies the associated statistical profile to incorporate the defined one or more patient behavioral goals. In another embodiment, the behavioral calculator 2124 modifies a statistical profile to reflect the association between the defined behavioral goals and the patient record stored in the patient record database 2116. In yet another embodiment, the behavioral calculator 2124 stores the defined behavioral goals in a separate database (not shown) and creates a logical association between the defined behavioral goals and the patient record stored in the patient record database 2116.

Referring back to FIG. 6, the patient monitoring processor 2120 may further determine that a patient statistical profile exists for a patient based on the received patient identification information (Block 614). When the patient monitoring processor 2120 has finished processing the patient statistical information for a pre-existing statistical profile, the patient monitoring processor 2120 may take a variety of actions, depending on the clinician 2102 input. For example, the patient monitoring system 2108 may prompt the clinician 2102 to select between modifying the patient statistical profile (Block 618) or generating a report of the patient record (Block 620). Alternatively, the patient monitoring processor 2120 could prompt the clinician 2102 to select other actions, such as modifying the pre-existing statistical profiles for one or more patients (Block 622), viewing one or more pre-existing statistical profiles for one or more patients, (Block 624) editing pre-existing statistical profiles for one or more patients (Block 626), or combinations thereof. In yet another alternative embodiment, the clinician may be able to create another statistical profile (Block 616) for a patient that has a pre-existing statistical profile. In another embodiment, the variety of actions previously discussed (Blocks 618-626) may be performed if a patient profile does not exist for the patient associated with the received patient identification information.

Figure 25:
FIG. 25 is one example of a patient record.
Figure 26:
FIG. 26 is one example showing comments entered into a patient record
Figure 27:
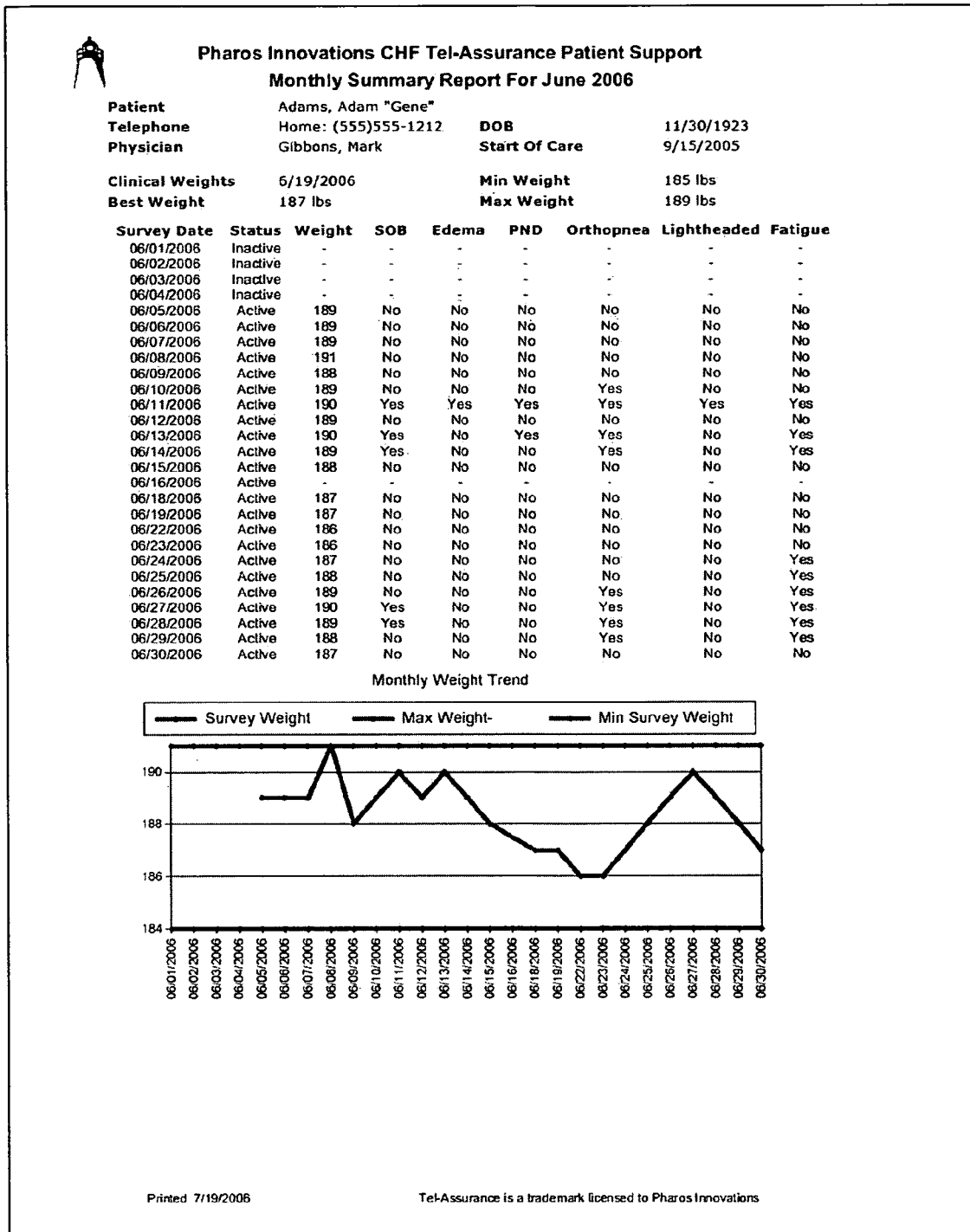
Figure 28:
Figure 29:
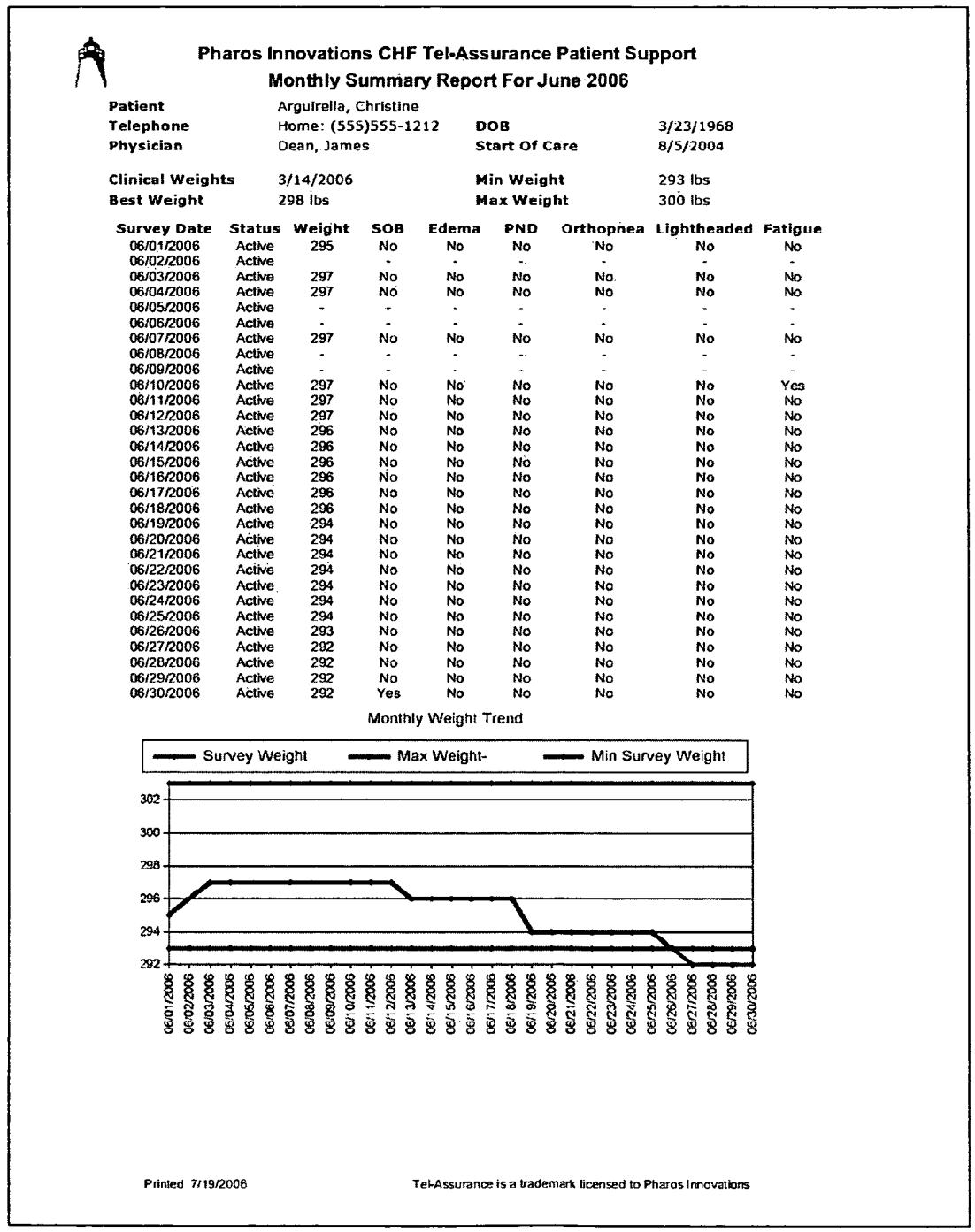
Figure 30:
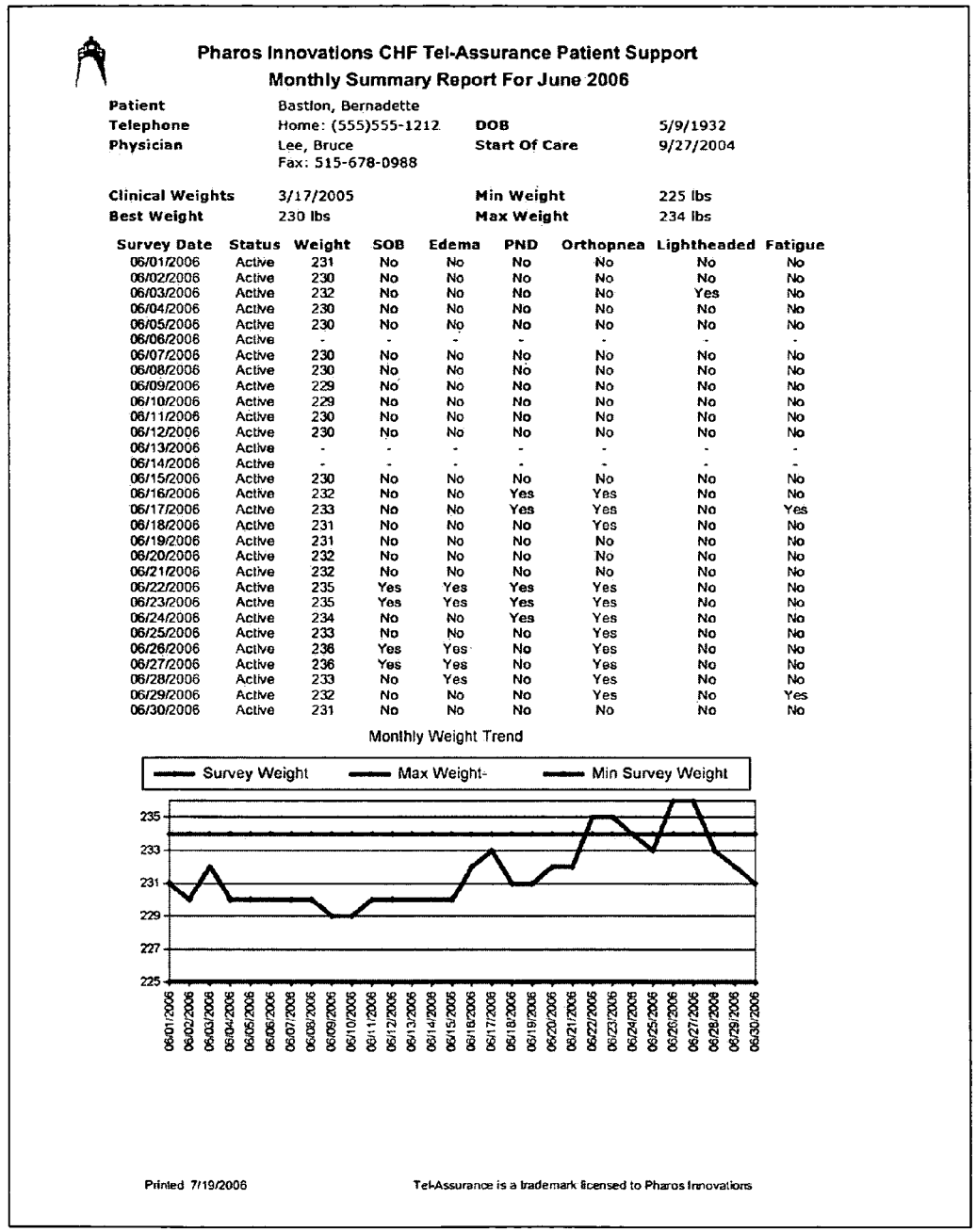
Figure 31:
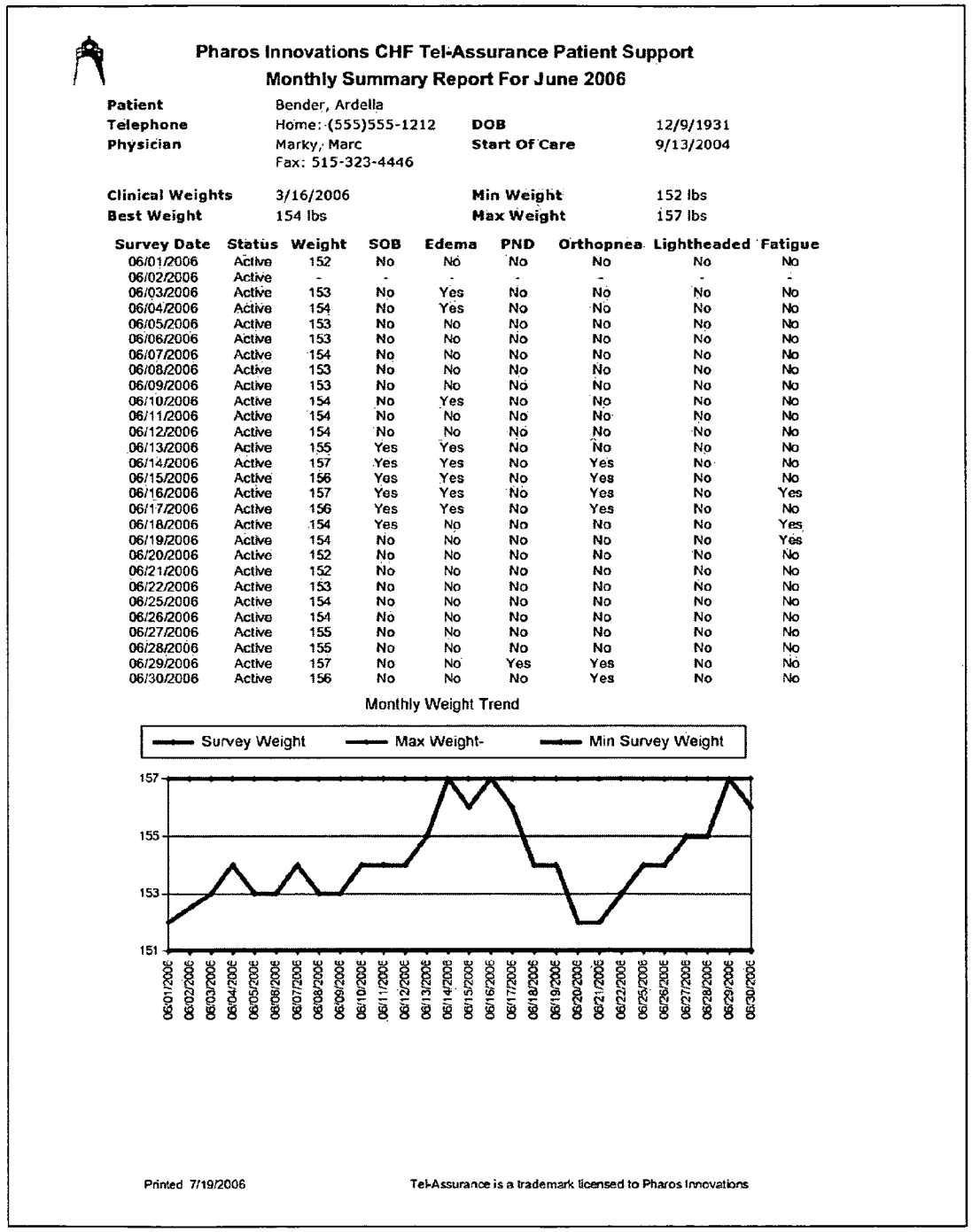
Figure 32:
Figure 33:
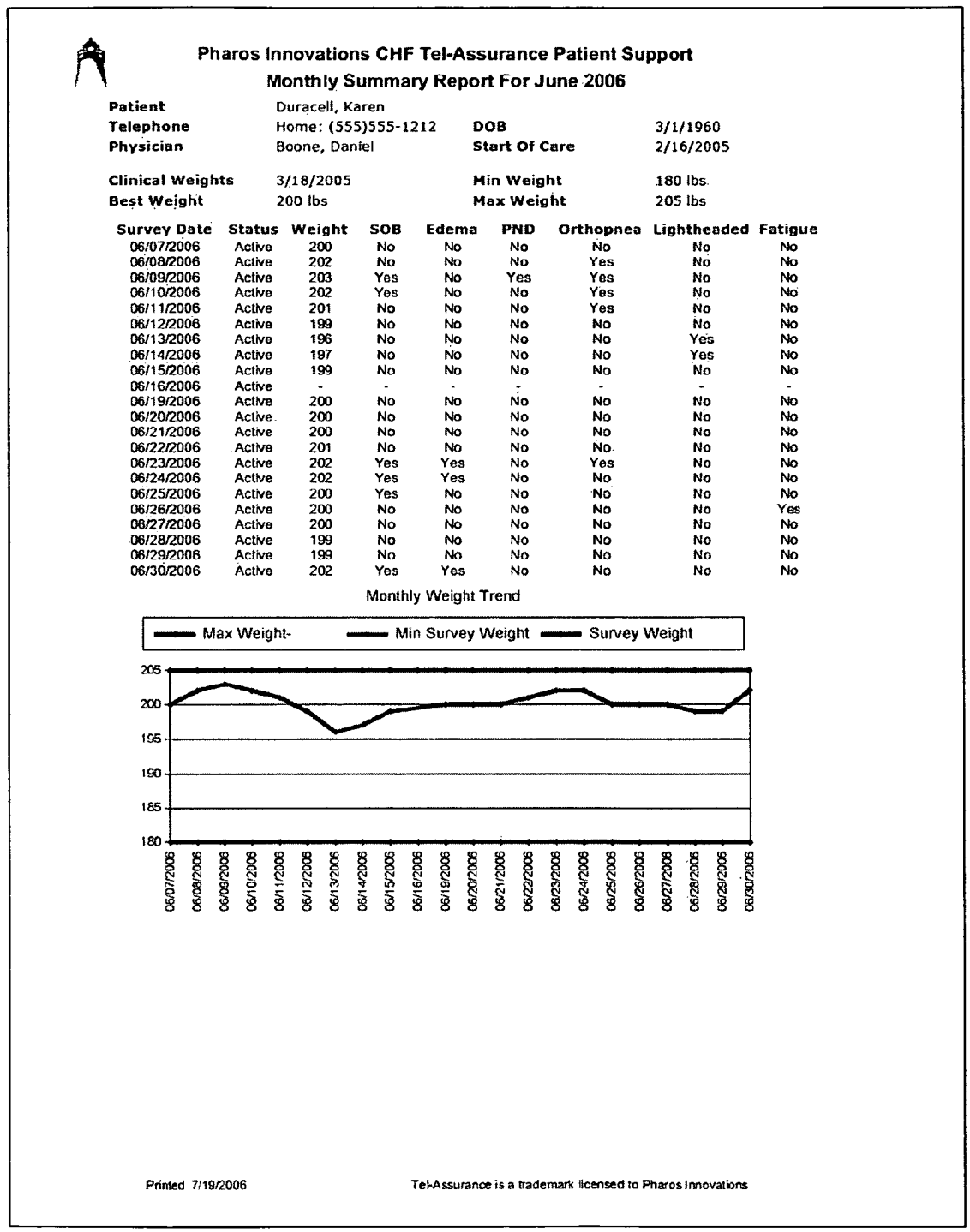
Figure 34:
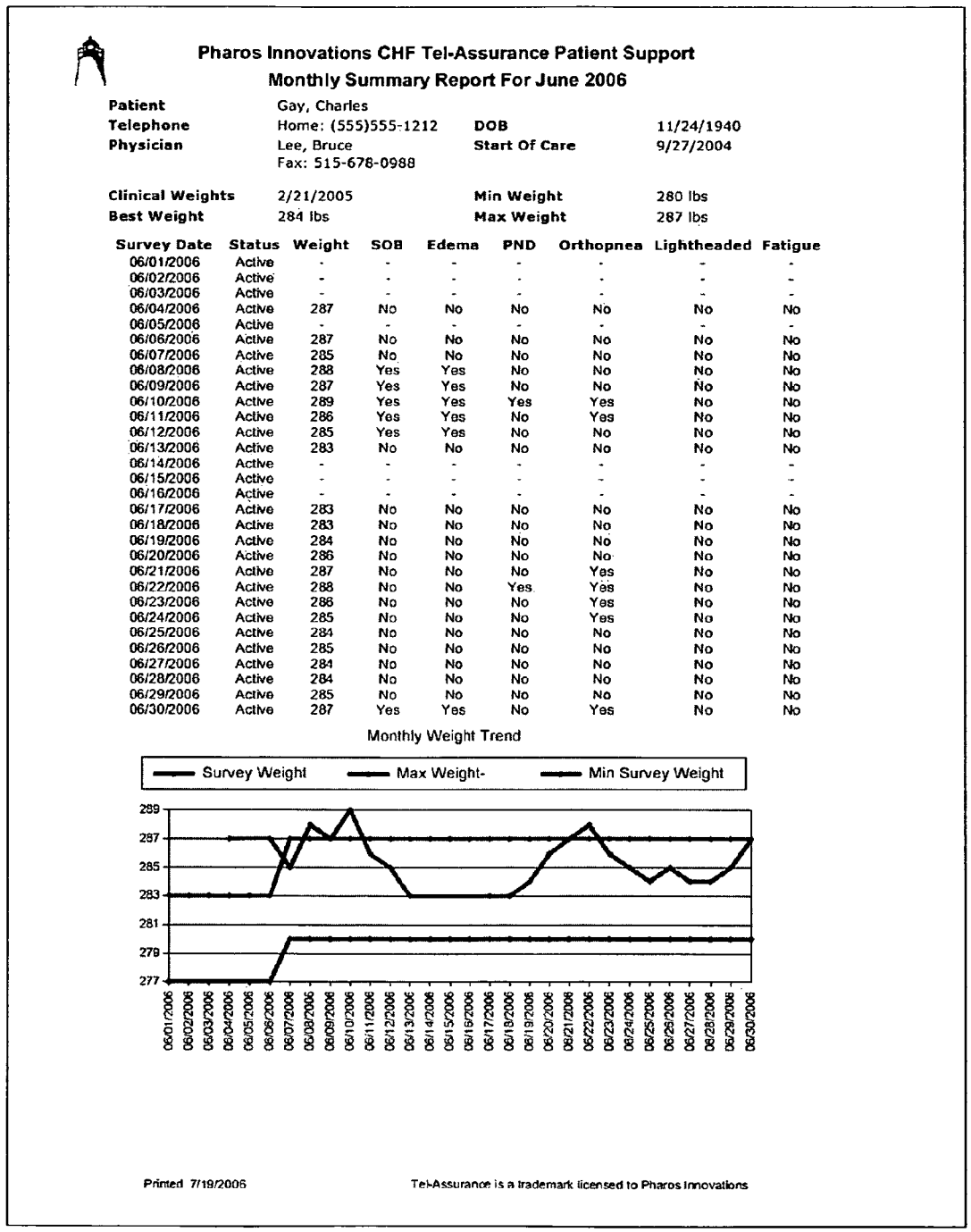
Figure 35:
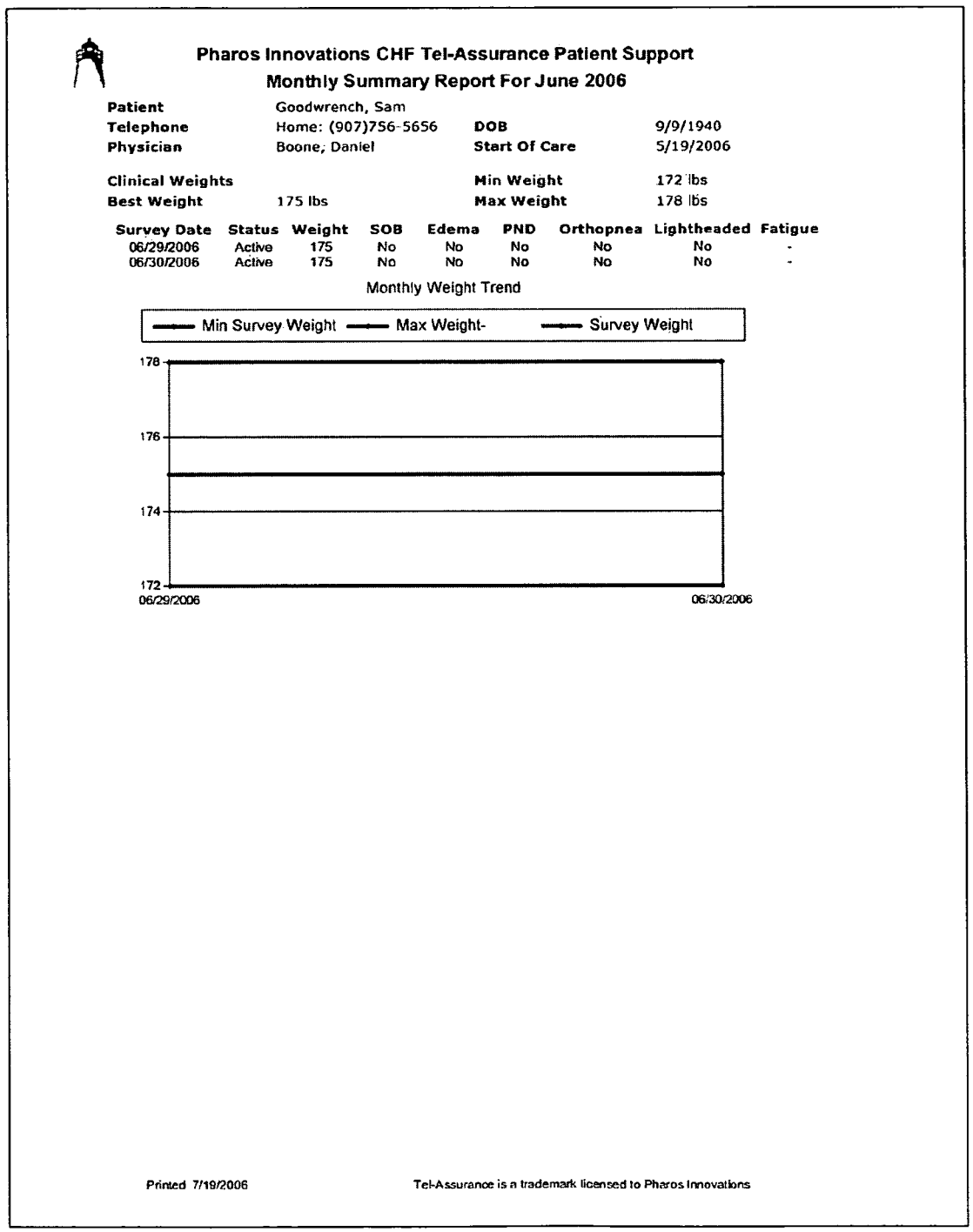
Figure 36:
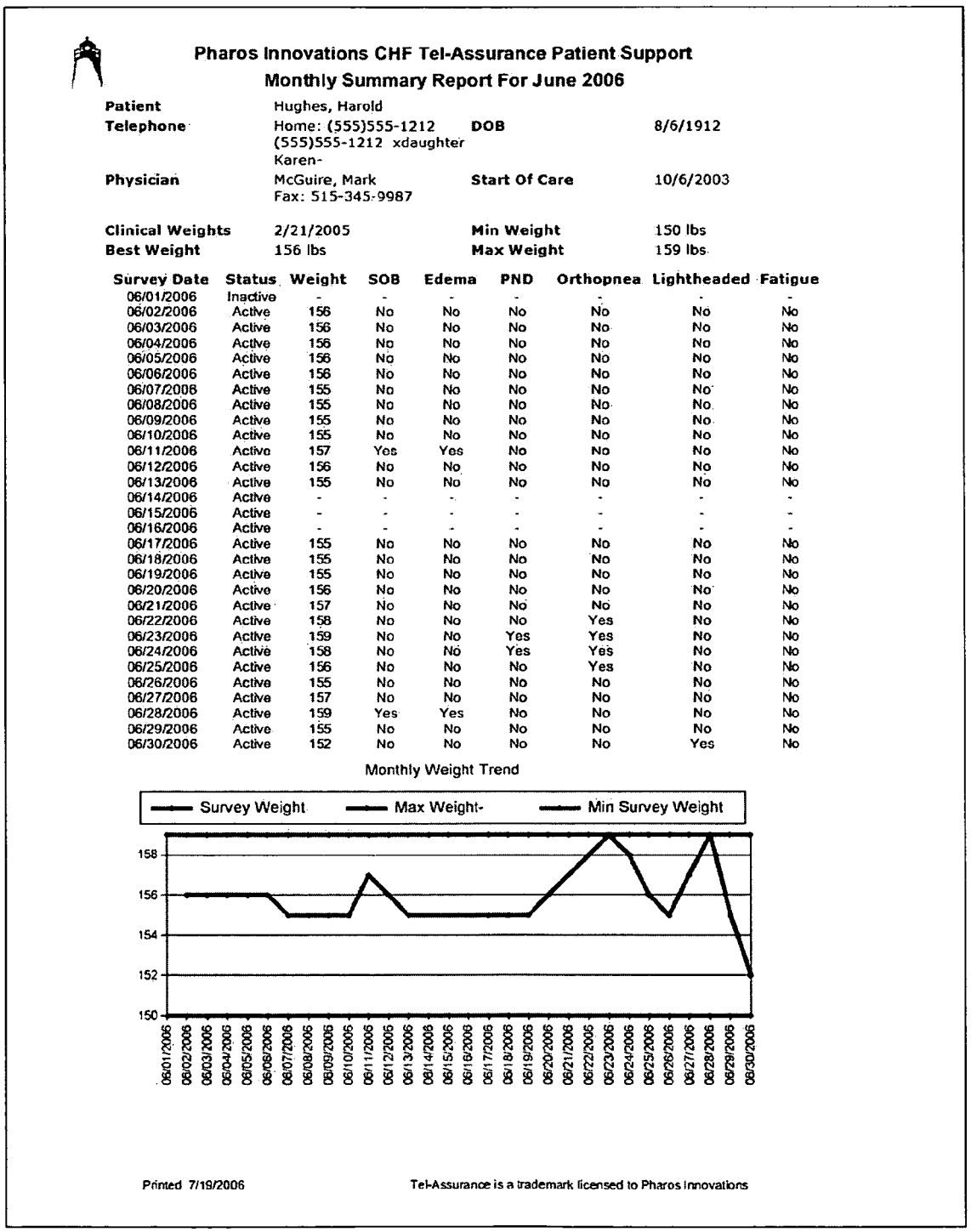
Figure 37:
Figure 38:
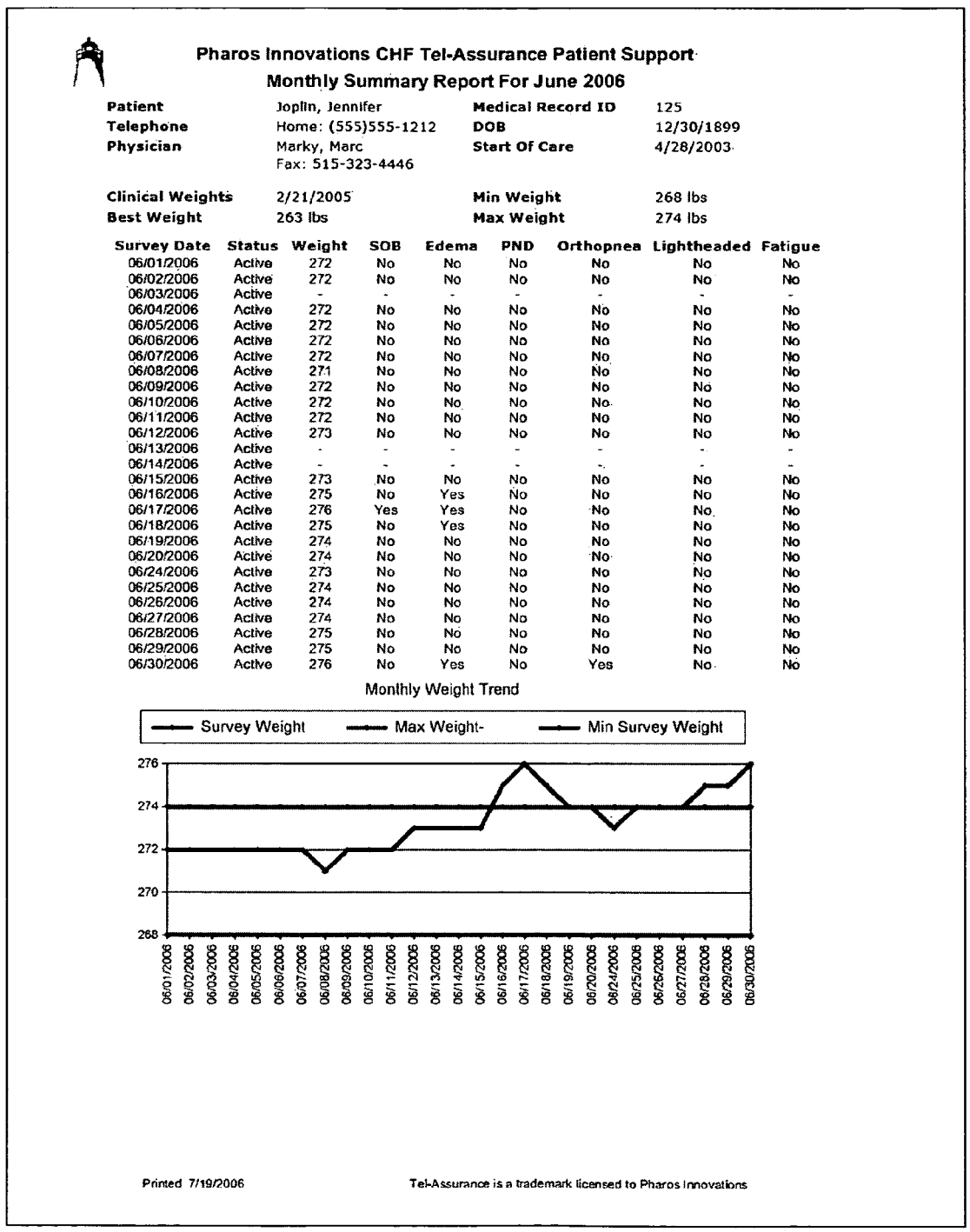
Figure 39:
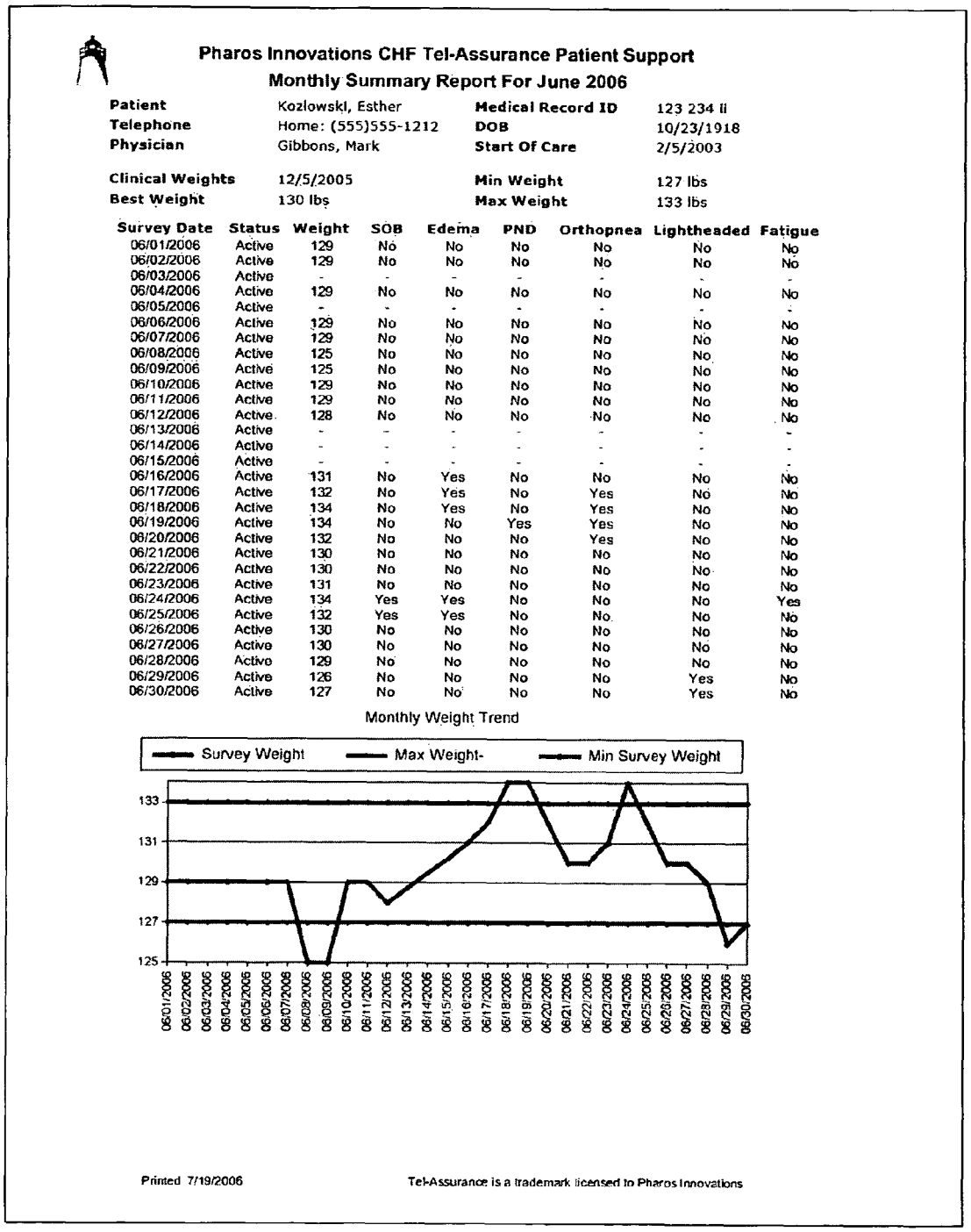
Figure 40:
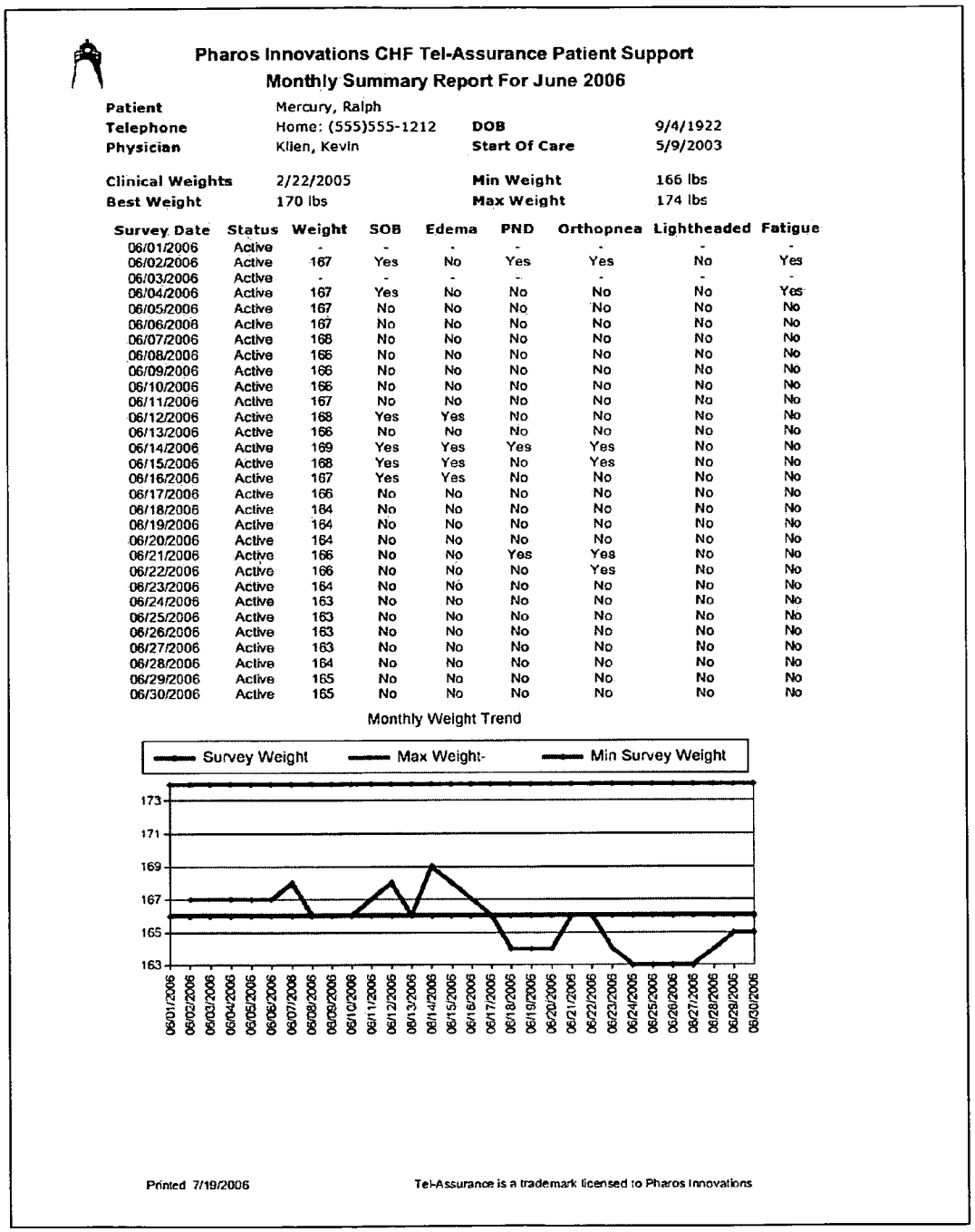
Figure 41:
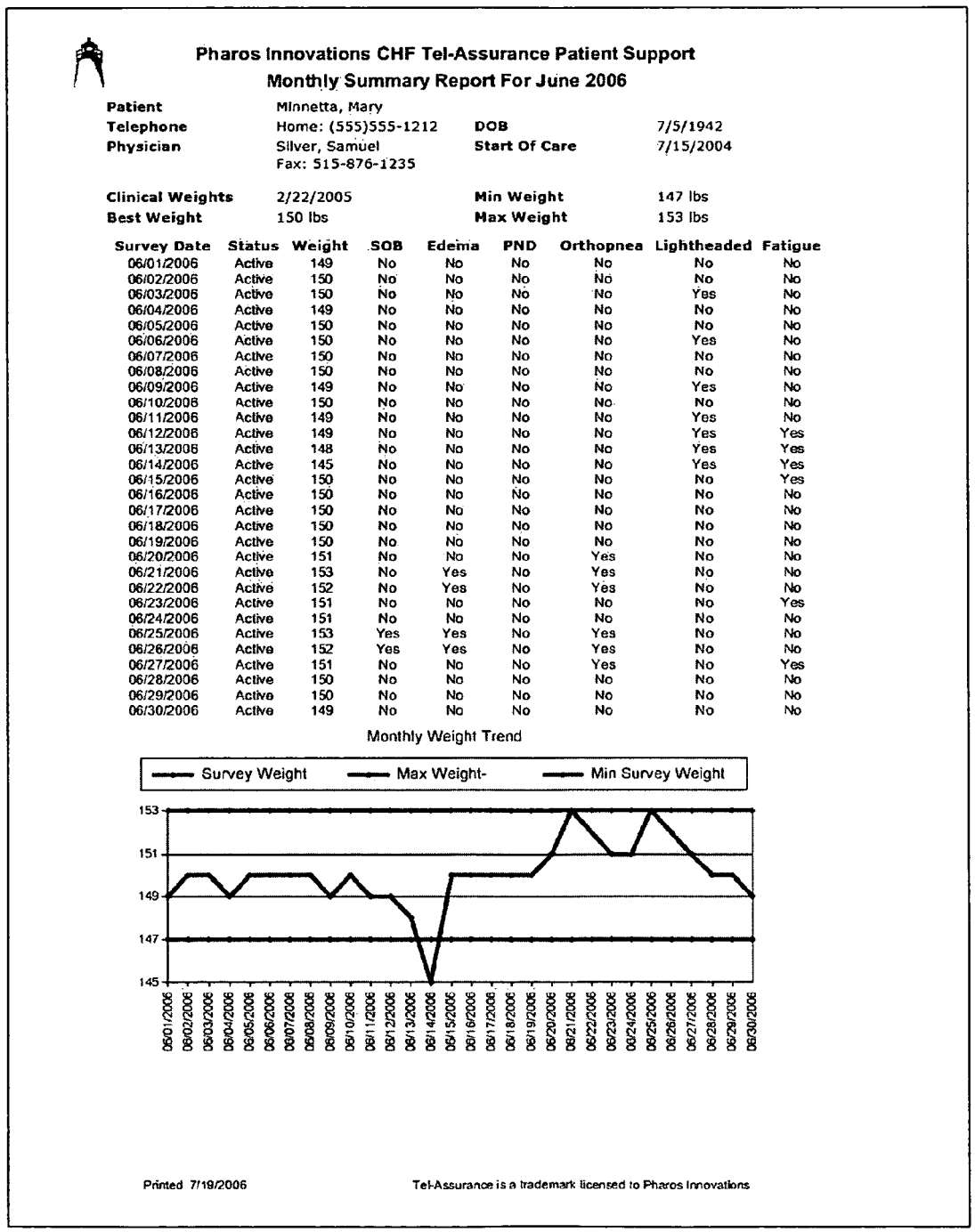
Figure 42:
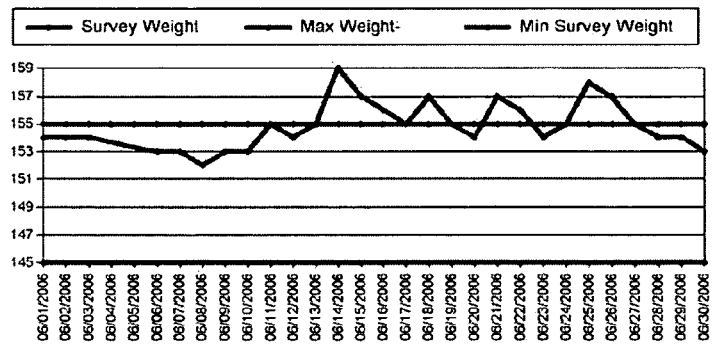
Figure 43:
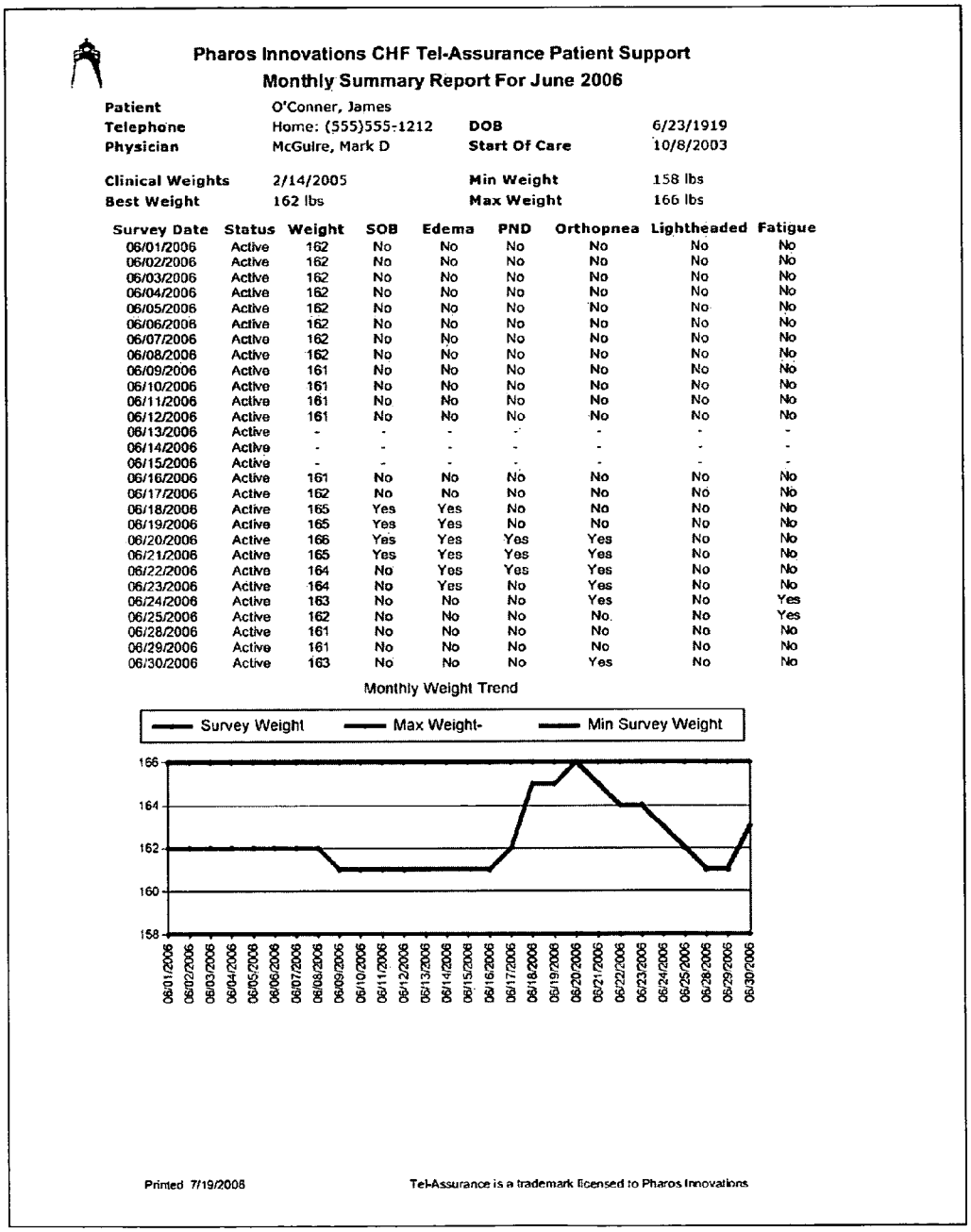
Figure 44:
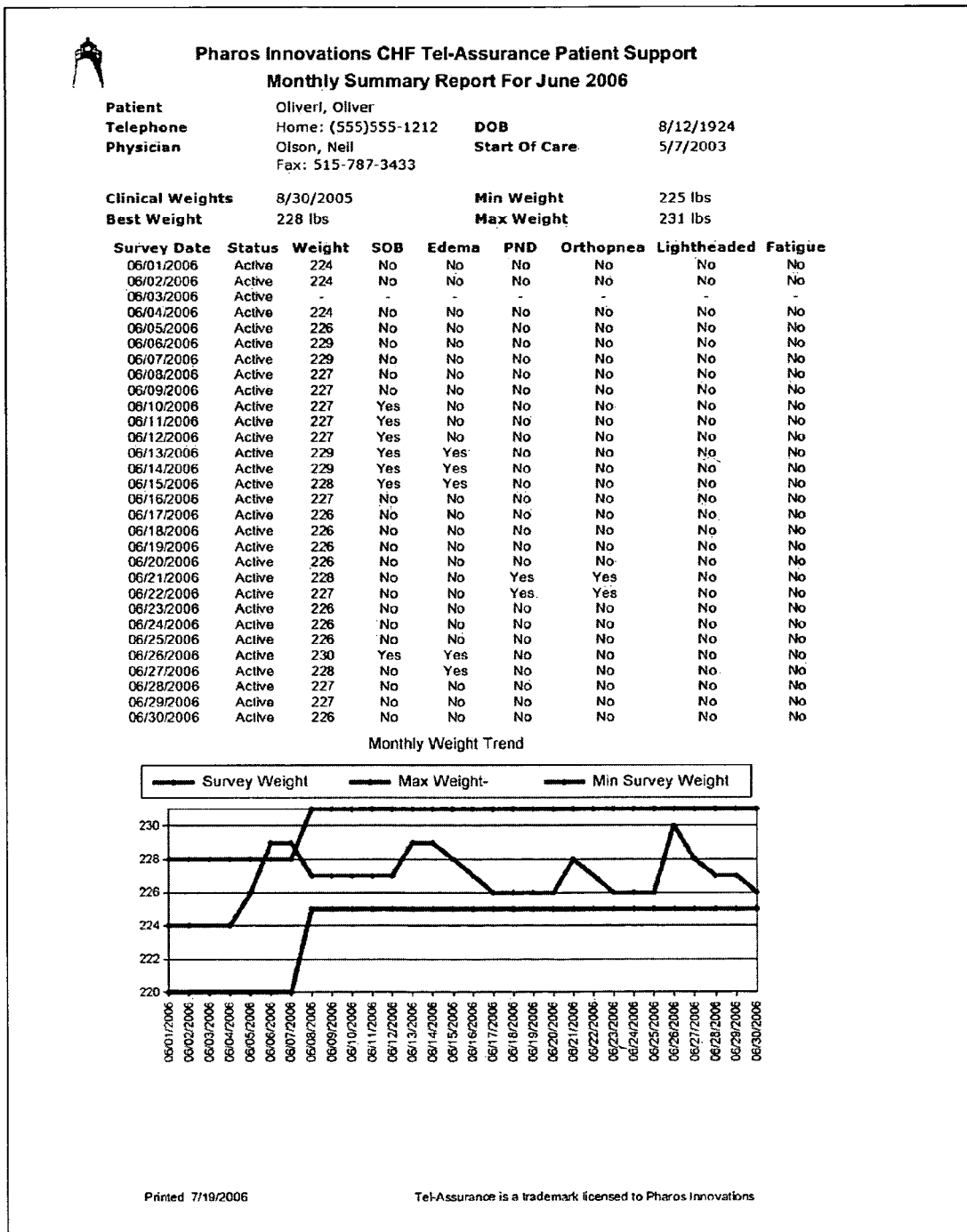
Figure 45:
Figure 46:
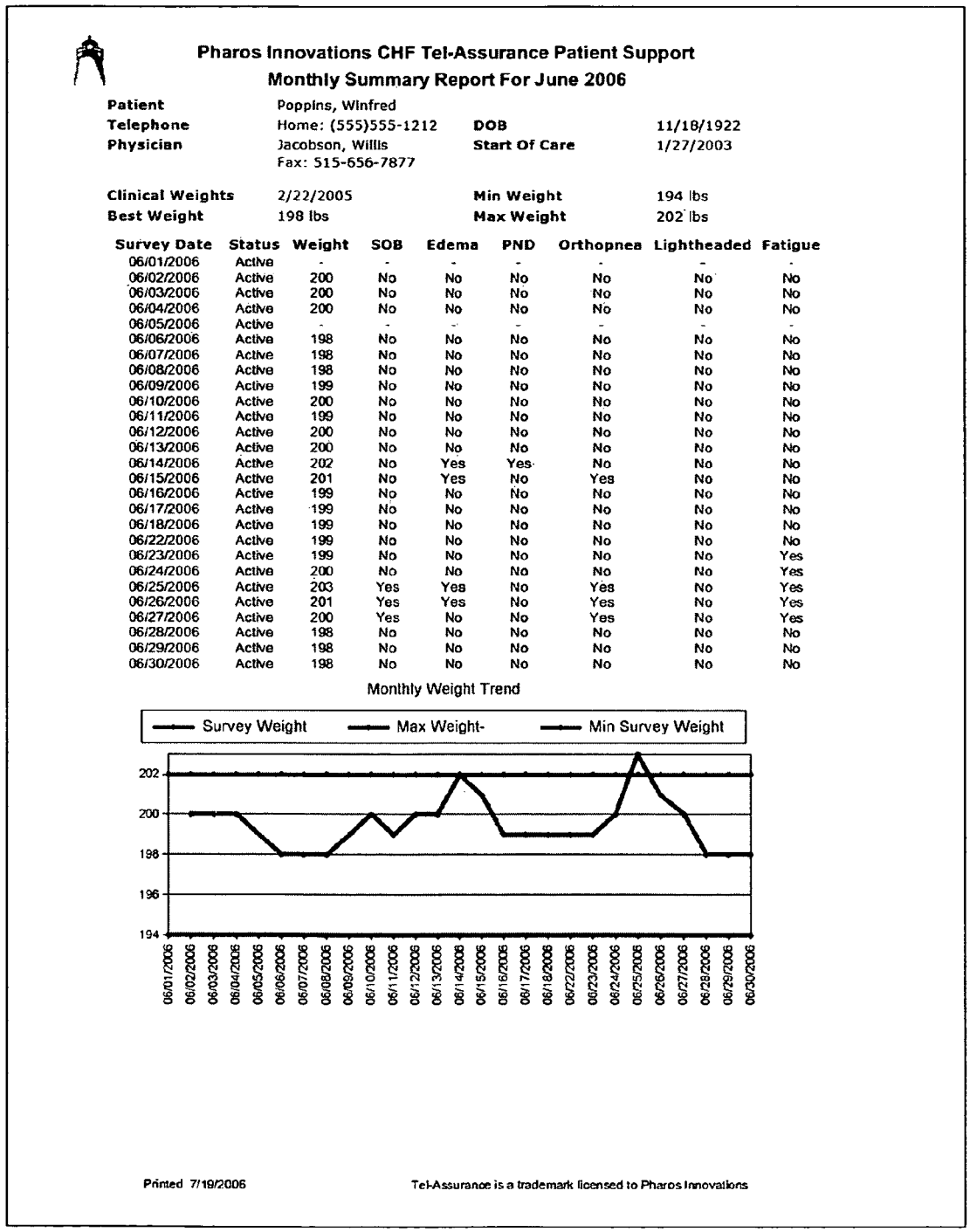
Figure 47:
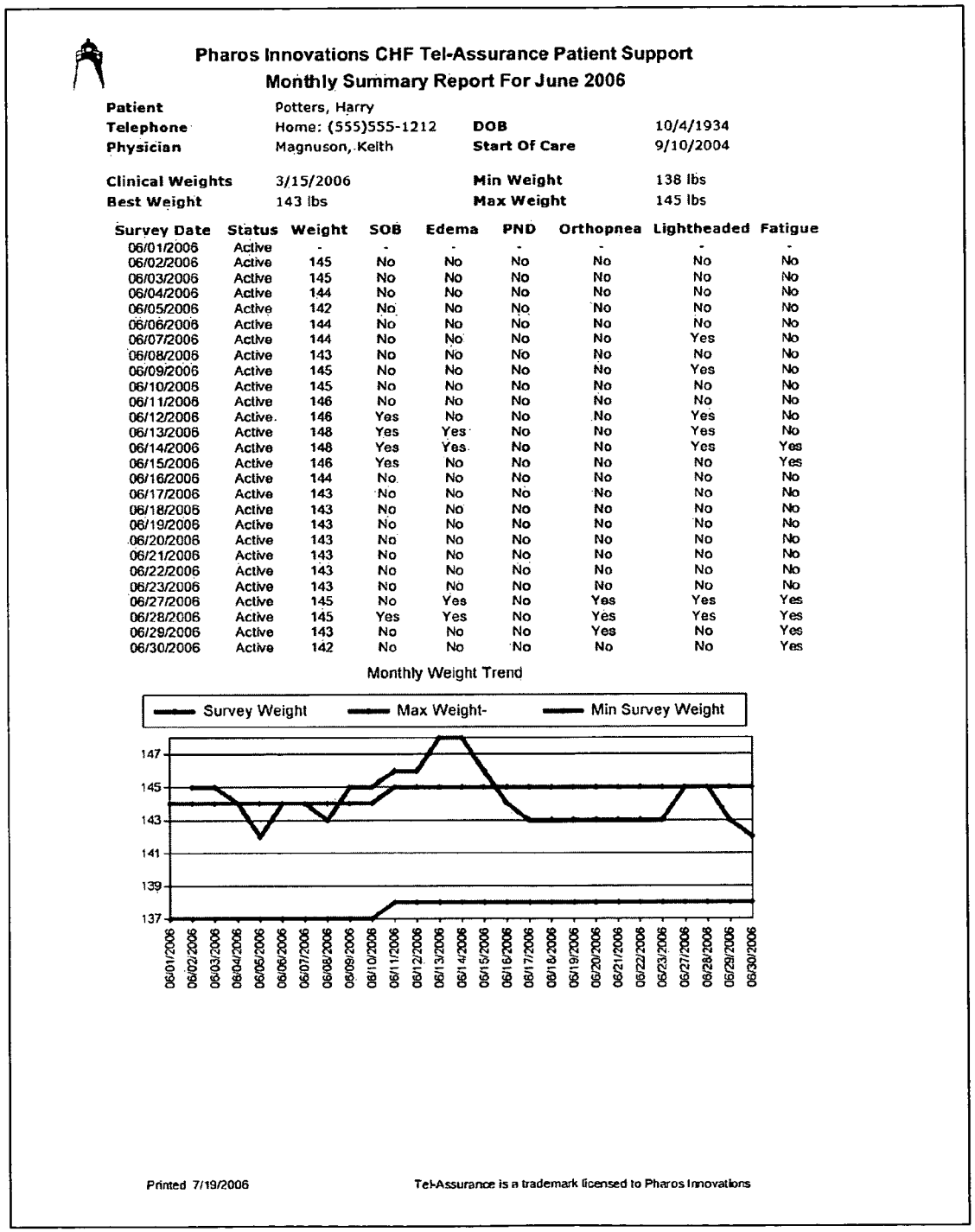
Figure 48:
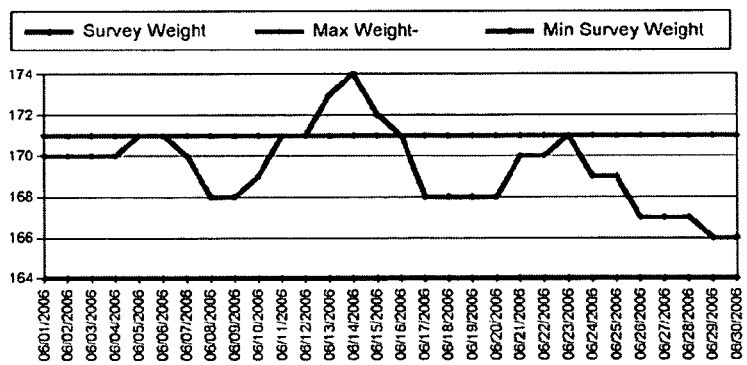
Figure 49:
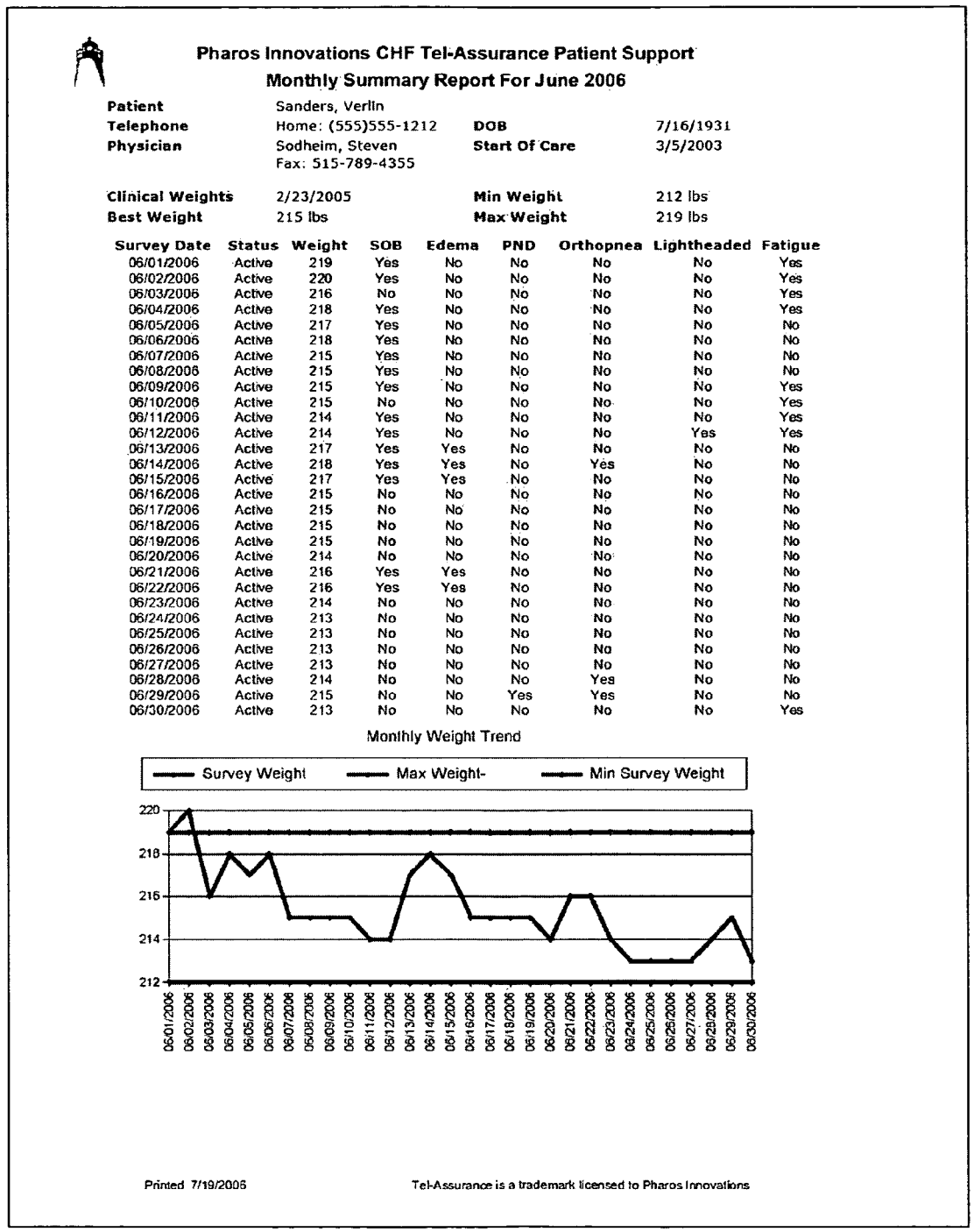
Figure 50:
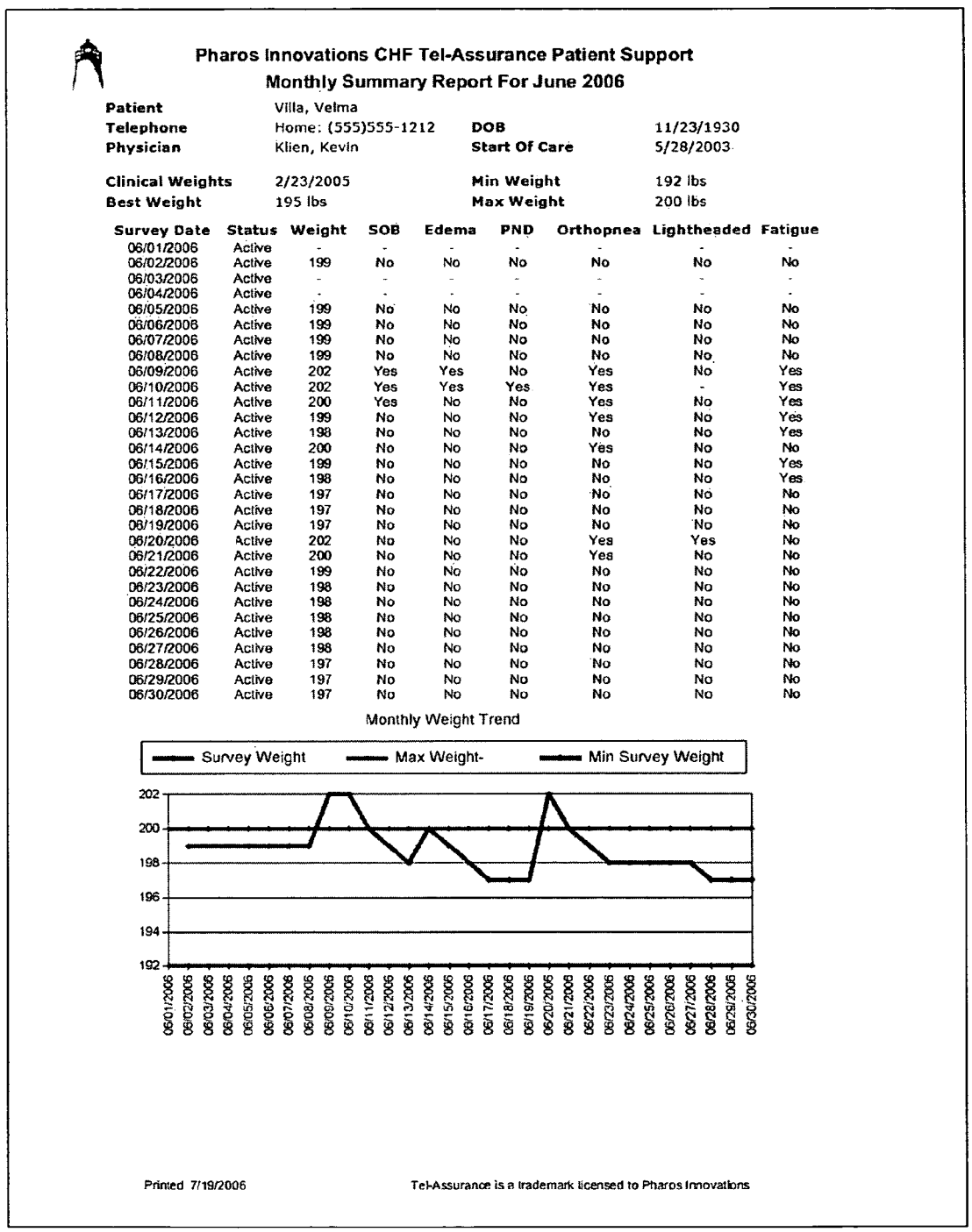
Figure 51:
Figure 52:
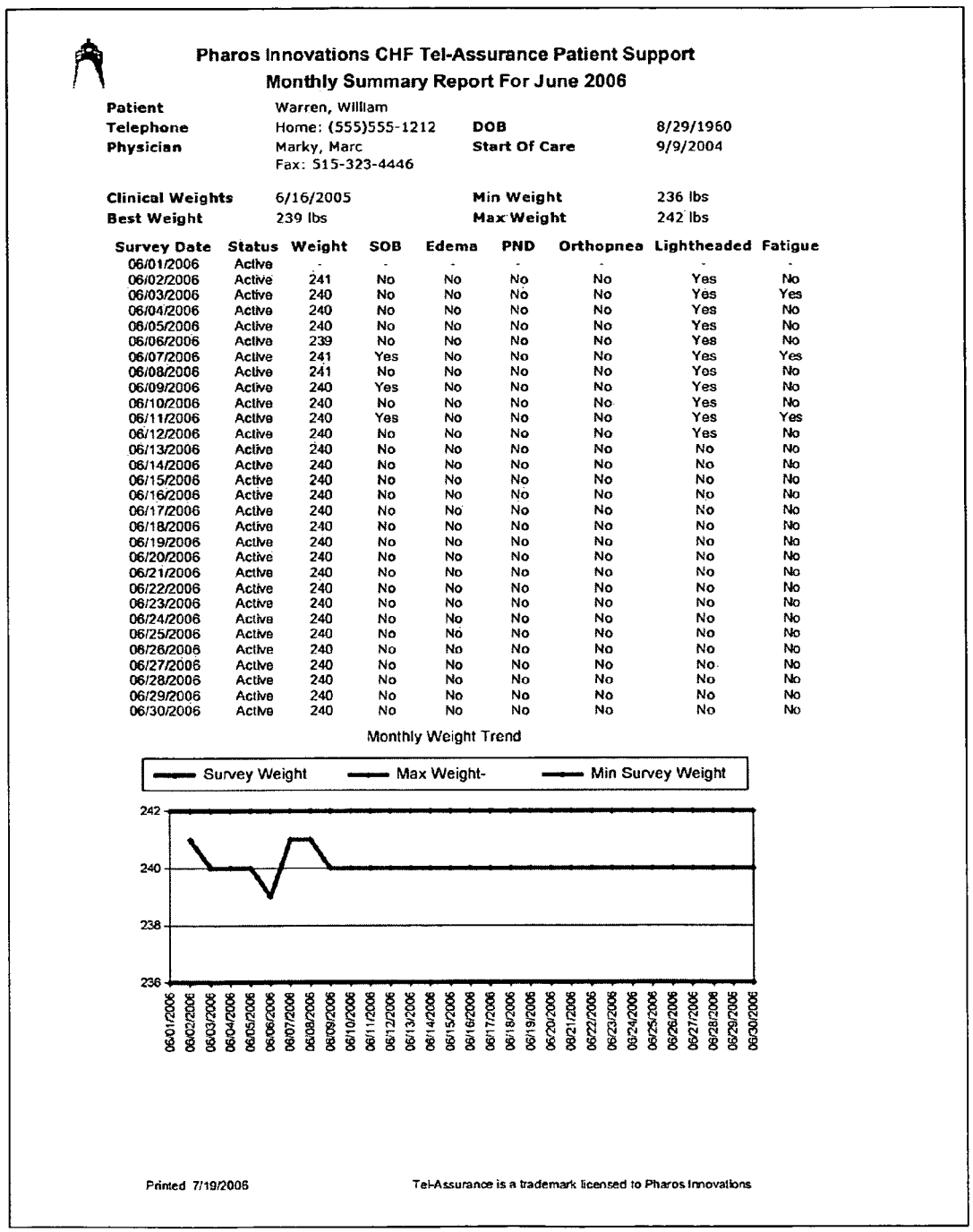
Figure 53:
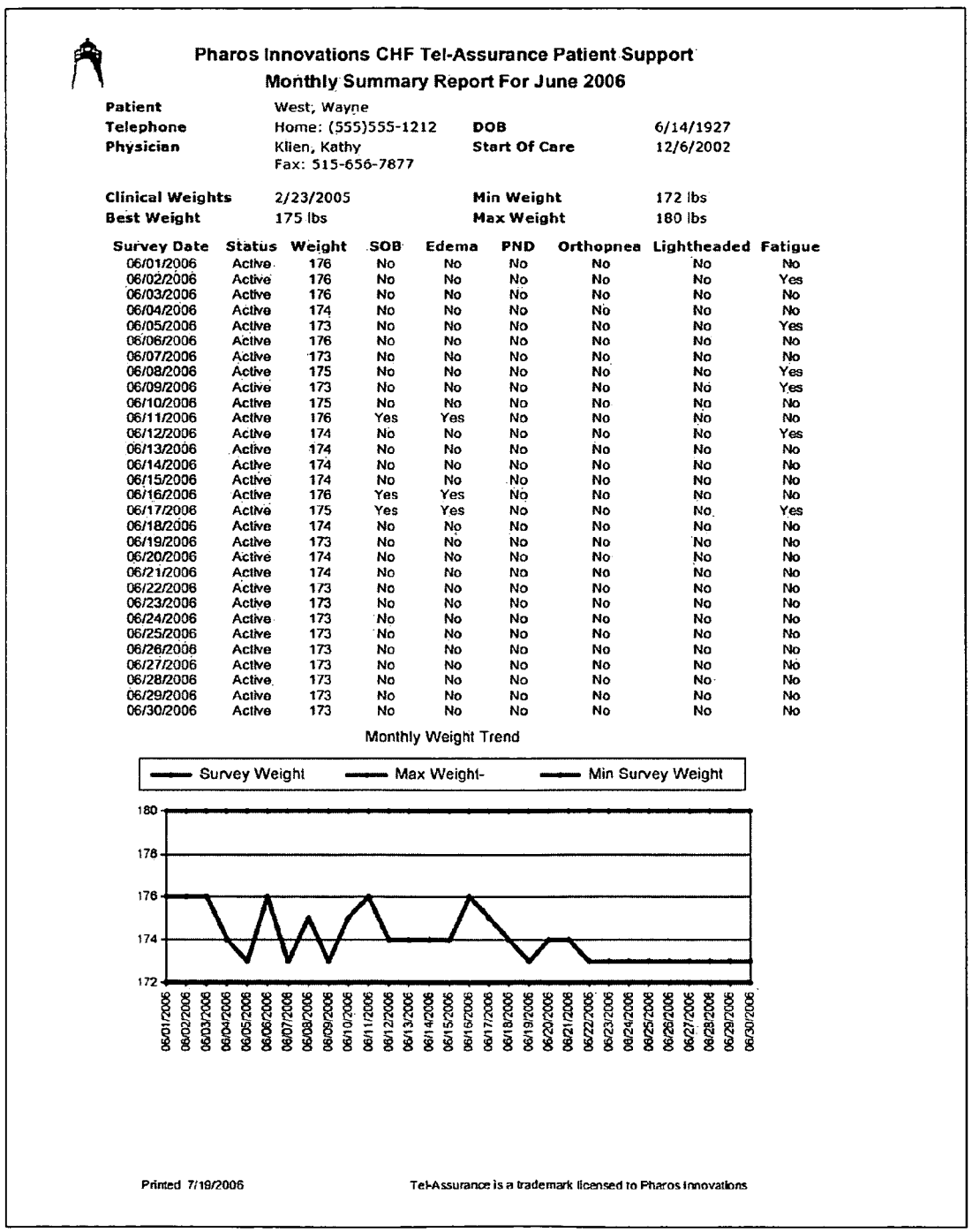

In providing a report of the patient record associated with a pre-existing patient statistical profile, the provided report may be based on a predetermined time frame, such as daily, weekly, monthly, yearly, or combinations thereof. The provided report could also be a dynamic report based on a selected timeframe chosen by the clinician 2102. In an alternative embodiment, the clinician 2102 may be able to access a compilation report of all patients that have similar characteristics, such as, similar objectives, goals, fault tolerances, statistical profiles, etc. FIG. 25 shows one example of a patient report generated using the patient monitoring system 2108. FIG. 25 may be produced based on the information in the patient record database 2116, the statistical profiles 2130, or a combination thereof. In one embodiment of the patient monitoring system 2108, the clinician 2102, the patient 2104, the external data source 2106, or a combination thereof, may add comments to the patient record stored in the patient record database 2116 for later reviewing in a patient report. FIG. 26 shows an exemplary report having comments entered into a patient record using the patient monitoring system 2108. The clinician 1502 may also generate monthly reports for individual patients. FIGS. 27-54 show other examples of individual monthly reports for patients involved in weight surveys. By way of example, FIG. 27 shows that the maximum survey weight was approximately 191 lbs., that the patient's weight fluctuated between 186 lbs. and 190 lbs, inclusive, and that the minimum survey weight was 184 lbs. Other individual reports are shown in FIGS. 28-54 and show similar graphical information, or no graphical information, depending on when the report was generated and the number of surveys the patient completed.

Figure 9:
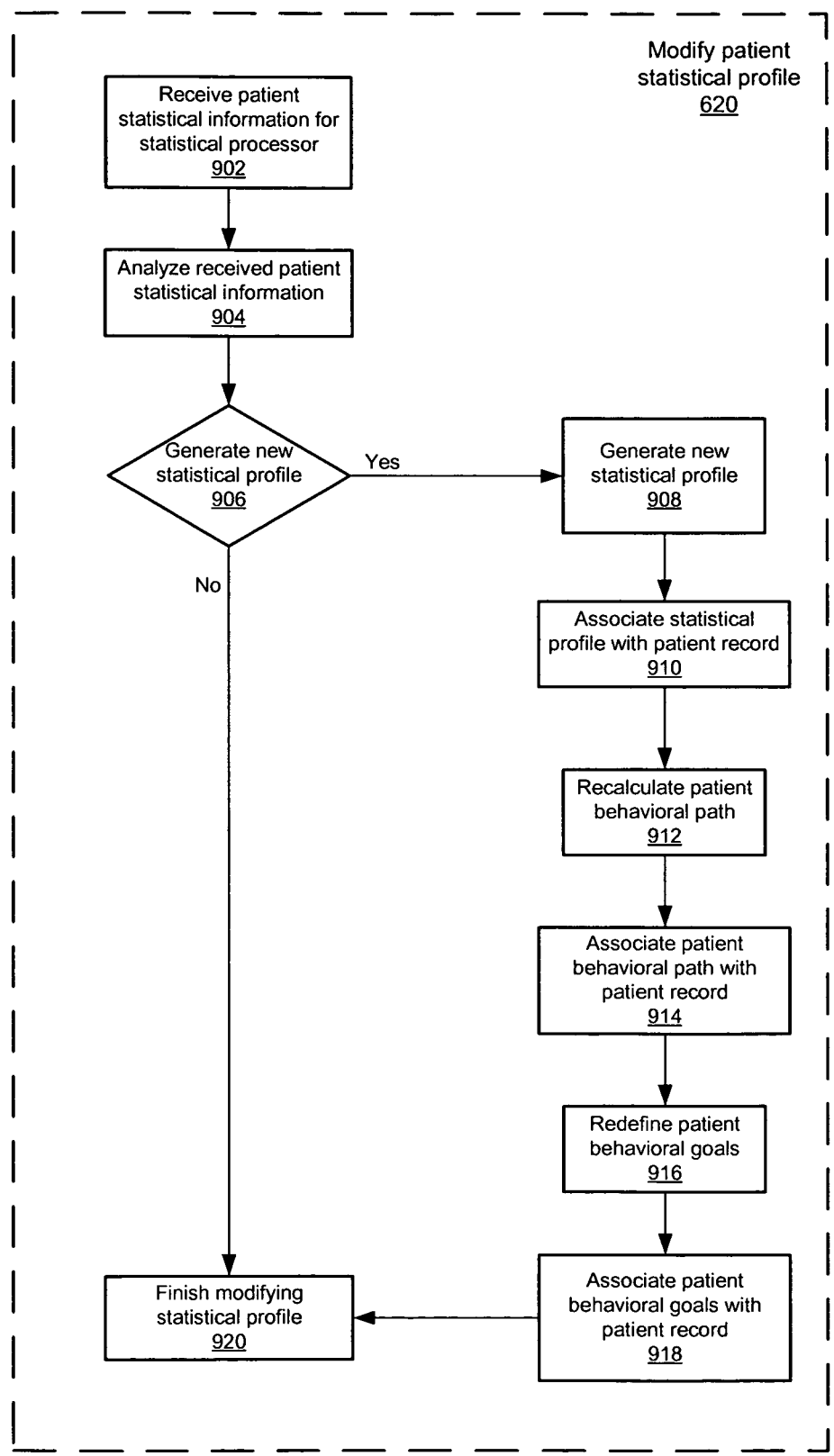
FIG. 9 is a flowchart of one embodiment of modifying a patient statistical profile.

FIG. 9 illustrates a flowchart depicting the operation of modifying an existing patient statistical profile according to one embodiment. For example, the clinician may provide additional information that affects the statistical profile associated with the patient record of the received patient identification information. As shown in FIG. 9, the statistical processor 2122 receives the patient statistical information from the patient monitoring processor 2120 (Block 902). The statistical processor 2122 may receive the statistical information from the patient monitoring processor 2122 over a wired link, a wireless link, or a combination thereof. In one embodiment, the patient monitoring processor 2120 formats the statistical information in a format understandable by the statistical processor 2122 as was described above.

After the statistical processor 2122 has received the patient statistical information from the patient monitoring processor 2120, the statistical processor 2122 then analyzes the received patient statistical information (Block 904). For example, the statistical processor 2122 may analyze the received patient statistical information to determine whether the received patient statistical information is in the correct format. The statistical processor 2122 may also analyze the received patient statistical information to determine whether the patient statistical information is capable of modifying the patient statistical profile, such as where the clinician provides information regarding the successfulness of a particular treatment. Other information affecting the statistical profile may include whether other patients have been successful in a particular line of treatments or, alternatively, if the particular treatments have had a high and/or low failure rate.

After the statistical processor 2122 analyzes the received patient statistical information, the statistical processor 2122 then determines whether to generate a new statistical profile (Block 906). If the statistical processor 2122 determines that the provided patient statistical information does not affect the previously existing statistical profile, the statistical processor 2122 may proceed to a finishing state of modifying the statistical profile (Block 920). In one embodiment, the statistical processor 2122 communicates with the patient monitoring processor 2120 to inform the patient monitoring processor 2120 that a new statistical profile is not needed.

Alternatively, the statistical processor 2122 may determine that a new statistical profile is needed. If the statistical processor 2122 makes this determination, the statistical processor 2122 generates a new statistical profile (Block 908). In one example, the statistical processor 2122 retains the information from the previously existing statistical profile and supplements the information of the pre-existing statistical profile with the received patient statistical information. In another example, the statistical processor 2122 generates a new statistical profile from the received patient statistical information. In generating the new statistical profile, the statistical processor 2122 may use the information from the pre-existing statistical profile, the received patient statistical information, or a combination thereof. The statistical processor 2122 may generate a patient statistical profile, a population statistical profile, or a combination thereof.

After generating a new statistical profile (Block 908), the statistical processor 2122 then associates the generated statistical profile with the patient record associated with the pre-existing statistical profile (Block 910). The statistical processor 2122 then communicates with the patient behavioral calculator 2124 to recalculate the patient behavioral path (Block 912) based on the generated statistical profile. For example, the patient behavioral calculator 2124 may calculate a new patient behavioral path that accounts for the success or failure rate of a particular treatment based on the new statistical profile.

Following the recalculation of the patient behavioral path, the patient behavioral calculator 2124 then associates the new patient behavioral path with the patient record (Block 914). After associating the patient behavioral path with the patient record (Block 914), the patient behavioral calculator 2124 proceeds to redefine the patient behavioral goal(s) (Block 916). The redefining of the patient behavioral goals may account for the recalculated patient behavioral path, the generated new statistical profile, or combination thereof. The patient behavioral calculator 2124 then associates the new patient behavioral goals with the patient record (Block 918). The patient behavioral calculator 2124 then informs the patient monitoring processor 2120 that the process of modifying a patient statistical profile is complete (Block 920) and, optionally, that it has finished calculating the behavioral path and redefining the behavioral goals.

Referring back to FIG. 1, after the clinician has finished accessing the patient monitoring system (Block 118), the patient monitoring system 2108 finishes the clinician session with the clinician (Block 122). In finishing the clinician session, the patient monitoring processor 2120 may review all of the accessing actions the clinician 2102 has taken during the accessing session. The patient monitoring processor 2120 could also provide an option for the clinician 2102 to review all of the previous clinician sessions (if any), and the actions taken during those previous clinician sessions. The patient monitoring processor 2120 could also verify the actions taken by the clinician 2102 during the clinician session and prompt whether the clinician 2102 wants to modify any (or all) of the actions taken during the clinician session. Once the clinician 2102 indicates that the clinician 2102 is satisfied with access session for the patient, the patient monitoring processor 2120 terminates the session between the clinician 2102 and the patient monitoring system 2108.

In addition to the access granted to a clinician 2102, a patient 2104, or a surrogate such as a clinician 2102 acting on behalf of a patient, as was described above, is also capable of accessing the patient monitoring system 2108. In one embodiment, the patient 2104 communicates with the patient monitoring system 2108 using an IVR interface. In another embodiment, the patient 2104 communicates with the patient monitoring system 2108 using an interface designed for Internet access, such as a web page provided by a web site associated with the system 2108. Other types of interfaces are also possible, such as an interface using both audible and visual prompts. The patient 2104 proceeds to communicate with the patient monitoring system 2108 by initiating a communication request (Block 102). The patient monitoring system 2108 then prompts the patient 2104 to provide user identification information (Block 104).

In one embodiment, the patient user identification is a personal identification number (PIN) associated with the patient record stored in the patient record database 2116. In another embodiment, the patient user identification is a combination of a username and password. The user identification information could further include biometric information associated with the patient record stored in the patient record database 2116. After the patient 2104 provides the user identification information, the patient monitoring system 2108 receives the user identification information (Block 106). The patient monitoring system 2108 receives the user identification information over communication link 2132. The communication link 2132 could be a packet-switched network, a circuit-switched network, or a combination thereof. The patient monitoring system 2108 then analyzes the user identification information (Block 108).

Analyzing the user identification information provided by the patient may include accessing the authorized users database 2134 by the information communication processor 2112. The information communication processor 2112 could also access the patient record database 2116 to determine whether the patient has authority to access the patient monitoring system 2108 based on the provided user identification information. In an alternative embodiment, the information communication processor 2112 could access both the authorized users database 2134 and the patient record database 2116 to determine whether the patient has access to the patient monitoring system 2108. After the information communication processor 2112 has analyzed the patient provided user identification information (Block 108), the information communication processor 2112 proceeds to the patient monitoring process (Block 120). When the patient 2104 completes the patient monitoring process (Block 120), the patient monitoring system 2108 finishes the patient session with the patient 2104 (Block 122).

Figure 10:
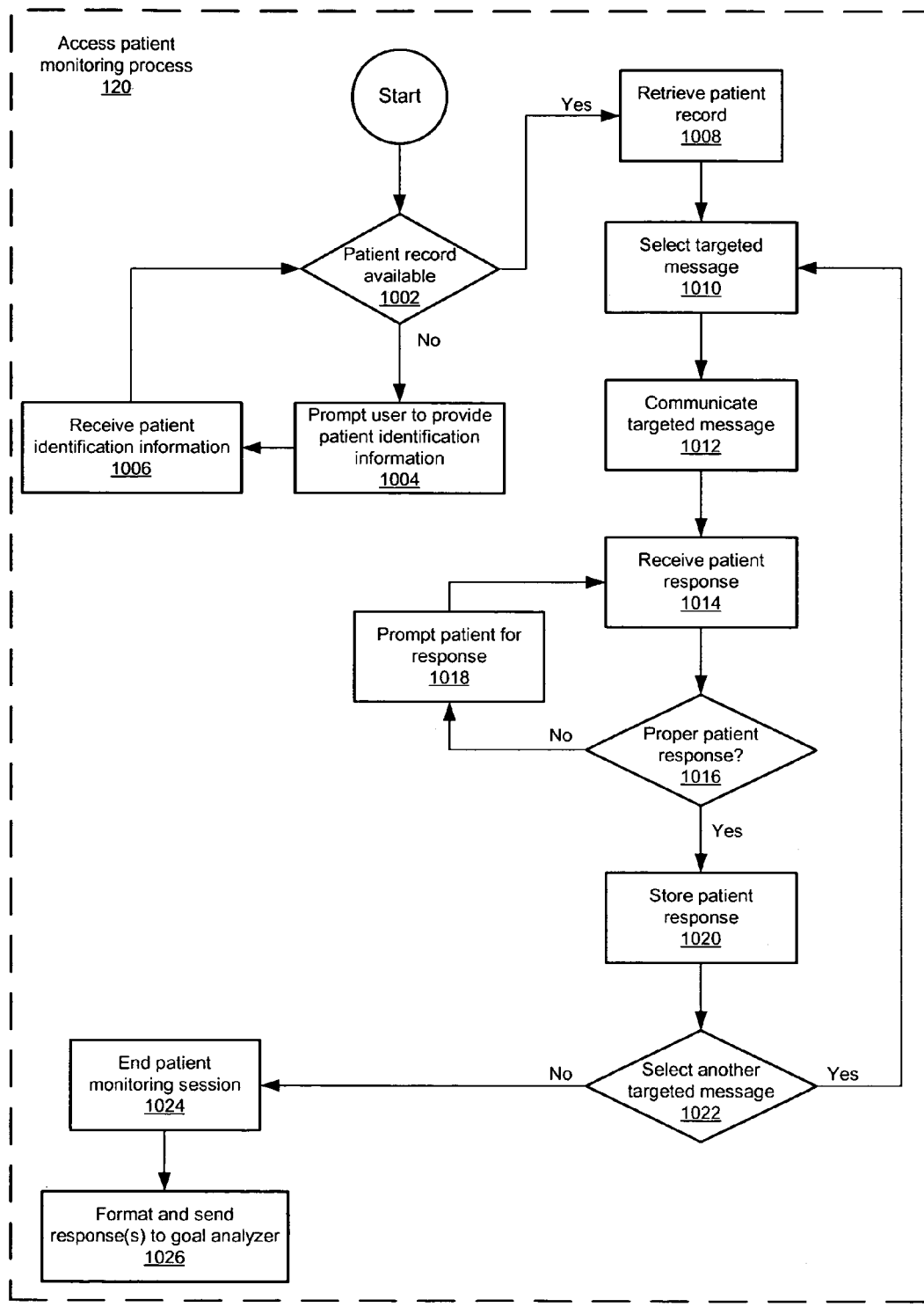
FIG. 10 is a flowchart of one embodiment of a patient accessing the patient monitoring system.

FIG. 10 is a flowchart of one example of a patient accessing the patient monitoring process (Block 120). The patient monitoring processor 2120 first determines whether a patient record is available based on the patient provided user identification information (1002). In one embodiment, the patient monitoring processor 2120 communicates with the patient enrollment processor 2114 to access the patient record database 2116. The patient monitoring processor 2120 provides the user identification information to the patient enrollment processor 2114 for retrieving a patient record from the patient record database 2116 associated with the user identification information. In another embodiment, the patient monitoring processor 2120 accesses the patient record database 2116 to determine whether a patient record exists associated with the patient provided identification information. If the patient monitoring processor 2120 or a patient enrollment processor 2114 determines that a patient record does not exist for the patient provided user identification information, the patient monitoring processor 2120 or the patient enrollment processor 2114 communicates with the information communication processor 2112 to prompt the patient to provide further patient identification information (Block 1004). For example, the patient may have provided incorrect user identification information and the patient monitoring system 2108 may have been unable to locate the patient record based on the incorrect patient provided user identification information. After the information communication processor 2112 has prompted the patient to provided further user identification information, the patient monitoring system 2108 then waits for the patient to provide further user identification information. In one embodiment, the patient monitoring system 2108 disconnects the patient from the patient monitoring system 2108 after a predetermined amount of time measured in seconds, minutes, hours, other measurements of time, or combinations thereof. Once the patient has provided further user identification information, the patient monitoring system 2108 then receives the further user identification information (Block 1006). The patient monitoring processor 2120 then determines whether a patient record exists in the patient record database 1516 based on the further provided user identification information.

If the patient monitoring processor 2120 determines that a patient record exists in the patient record database 2116 based on the patient provided user identification information, the patient monitoring processor 2120 then retrieves the patient record from the patient record database 2116 (Block 1008). Alternatively, or in addition to the information provided from the patient record, the patient 2104 may provide patient statistical information to the patient monitoring 2120 for selecting a targeted message to send to the patient 2104. The patient monitoring processor 2120 then selects a targeted message for the patient (Block 1010). A targeted message is a message intended to elicit a response from the patient indicating whether the patient is proceeding along a behavioral path towards achieving a behavioral objective. For example, the patient monitoring processor 2120 may select a targeted message based on the patient questionnaire associated with the patient record from the patient questionnaire database 2118. The patient monitoring processor 2120 may also select a targeted message based on the behavioral path associated with the patient record. The selected targeted message could also be based on previous responses to prior targeted messages sent by the patient monitoring system 2108.

In one embodiment, the selected targeted message is a question from the associated questionnaire, such as a message intended to elicit a direct response, such as an affirmative answer or a negative response, from the patient. For example, the desired behavioral objective by the patient may be to wake up earlier in the morning. In this example, the targeted message is a question, such as "Did you wake up at 6:00 a.m.?" In another example, the desired behavioral objective by the patient may be to stop smoking. In this example, the targeted question is a different question, such as "Did you smoke more than five cigarettes today?" In each example, the targeted message is designed to elicit a response from the patient. Other questions designed to elicit a response from the patient are also possible.

In another embodiment, the selected targeted message is a message intended to elicit an indirect response, such as a change in behavior by the patient. For example, the patient may be required to communicate with the patient monitoring system 2108 on a regular schedule to receive a particular positive or negative message. In this example, the targeted message is a statement, such as "Thank you for calling today, you are doing a great job!" The targeted message could also be a negatory statement, such as "You will not smoke today!"

When the patient monitoring processor 2120 has selected a targeted message, the patient monitoring processor then communicates the targeted message to the patient 2104 using the information communication processor 2112 (Block 1012). In one embodiment, the targeted message communicated to the patient 2104 is an audible message, such as where the patient 2104 communicates with the information communication processor 2112 using an IVR interface. In another embodiment, the targeted message communicated to the patient 2104 is a visual message, such as where the patient 2104 communicates with the information communication processor 2112 using a computer. The targeted message could also be communicated to the patient 2104 using a combination of audible and visual prompts.

After communicating the targeted message to the patient 2104 (Block 1012), the information communication processor 2112 then receives a patient response (Block 1014). In another embodiment, the information communication processor 2112 analyzes the targeted message before it is sent to determine whether a response is expected. For example, the information communication processor 2112 may expect to receive a response from the patient 2104 before sending the targeted message. When the patient response is received by the information communication processor 2112, the communication processor 2112 communicates the received response to the patient monitoring processor 2120. The patient monitoring processor 2120 then determines whether a proper patient response was received (Block 1016). In one embodiment, the patient monitoring processor 2120 has access to responses that are considered proper based on the selected targeted message. For example, if the selected targeted message was "Did you smoke more than five cigarettes today?", the patient monitoring processor 2120 would expect a response in the form of an affirmative or negative answer, such as "Yes" or "No." However, in this example, if the patient 2104 provides an answer such as "Blue," the patient monitoring processor 2120 would determine that this was not a proper response. The responses that are considered proper, or in a form considered proper, may be stored in a database coupled with the patient monitoring system 2108. In another embodiment, the patient response is reviewed by an external actor, such as a clinician or healthcare provider. If the patient monitoring processor 2120 determines that the response received from the patient is not a proper response, the patient monitoring processor 2120 prompts the patient for another response to the selected targeted message (Block 1018).

In another embodiment, the patient monitoring processor 2120 may present a survey comprised of targeted messages as a web page based form that the patient 2104 fills out entirely and then submits, e.g. all of the responses are submitted in batch to the patient monitoring system 2108. Alternatively, or in addition to the use of a web page, the patient monitoring processor 2120 may present the survey of targeted messages using the IVR interface. In this embodiment, the patient monitoring processor 2120 analyzes the responses submitted by the patient 2104 at one time as a group rather than analyzing the responses individually. The patient monitoring processor 2120 may then proceed, as described above, in selecting additional targeted messages, surveys, or combinations thereof, for answering by the patient 2104.

Once the patient monitoring processor 2120 has determined that a proper patient response has been received, the patient monitoring processor 2120 then stores the patient's response (Block 1020). In one embodiment, the patient monitoring processor 2120 stores the patient response directly in the patient record database 2116. For example, the patient monitoring processor 2120 could create a logical association between the patient record store in the patient record database 2116 and the patient response stored in the patient record database 2116. In another embodiment, the patient monitoring processor 2120 could store the patient response in the patient record of the patient record database 2116. For example, the patient monitoring processor 2120 could create a new field representing the patient's response in the patient record stored in the patient record database 2116. In yet another embodiment, the patient monitoring processor 2120 could store the patient's response in a separate database coupled with the patient monitoring processor 2120 and logically associated with the patient record stored in the patient record database 1560. The separate database could be part of the same system as the patient monitoring processor 2120, part of a different system, or a combination thereof.

The patient monitoring processor 2120 then determines whether to select another targeted message for the patient (Block 1022). In one embodiment, the patient monitoring processor 2120 makes this determination based on whether there is a subsequent question remaining from the patient questionnaire associated with the patient record. For example, the patient monitoring processor 2120 may select a patient questionnaire for the patient that has a series of questions, each of which are to be answered sequentially. In another embodiment, the patient monitoring processor 2120 selects another targeted message based on the received patient response. For example, the patient monitoring processor 2120 could employ branching logic that determines a subsequent targeted message to send based on the received patient response, such as directed by the questionnaire. In yet another embodiment, the patient monitoring processor 2120 could select another targeted message based on the behavioral path associated with the patient record when compared with the received patient response. For example, the patient monitoring processor 2120 could determine that the patient is no longer on the behavioral path based on the received patient response, and therefore select a targeted message designed to steer the patient back towards the patient behavioral path. The patient monitoring processor 2120 may also utilize a combination of the patient questionnaire associated with the patient record, the received patient response, and the patient behavioral path and/or behavioral objective to select another targeted message. If the patient monitoring processor 2120 determines to select another targeted message (Block 1022), the patient monitoring processor 2120 then selects the next targeted message (Block 1010).

If the patient monitoring processor 2120 determines not to select another targeted message, the patient monitoring processor 2120 then ends the patient monitoring session with the patient (Block 1024). In one embodiment, the patient monitoring processor 2120 communicates with the patient 2104 to inform the patient 2104 that the patient monitoring session has ended. For example, the patient monitoring processor 2120 or the information communication processor 2112 could send audible and/or visual prompt to the patient 2104 informing the patient 2104 of the end of the session, depending on the type of interface used. Where the patient 2104 communicates with the patient monitoring processor 2120 using an IVR interface, the patient monitoring processor 2120 or the information communication processor 2112 may send an audible prompt to the patient 2104 alerting the patient 2104 to the end of the patient monitoring session. Alternatively, where the patient 2104 communicates with the patient monitoring processor 2120 using an Internet interface, such as a web page, the patient monitoring processor 2120 or the information communication processor 2112 could send an audible/visual prompt to the patient 2104 allowing the patient 2104 to the end of the patient monitoring session. Other types of communication are also possible.

After the patient monitoring system 2108 has ended the patient monitoring session with the patient 2104 (Block 1024), the patient monitoring processor 2120 then formats and sends the one or more patient responses to the patient goal analyzer 2126 (Block 1026). For example, the patient goal analyzer 2126 may expect the patient response to be in a format different than the format received by the patient monitoring processor 2120. Such formats include, but are not limited to, text-files, binary files, comma-delimited files, proprietary formats, other types of files, or combinations thereof. Where the patient goal analyzer 2126 expects the one or more patient responses in a format different than one or more patient responses received by the patient monitoring processor 2120, the patient monitoring processor 2120 performs format conversion on the received one or more patient responses.

The patient goal analyzer 2126 is configured to analyze the received patient responses. In one embodiment, the patient goal analyzer 2126 is a programmable processor that analyzes the patient responses to determine whether the patient is meeting the patient behavioral goals.

Figure 11:
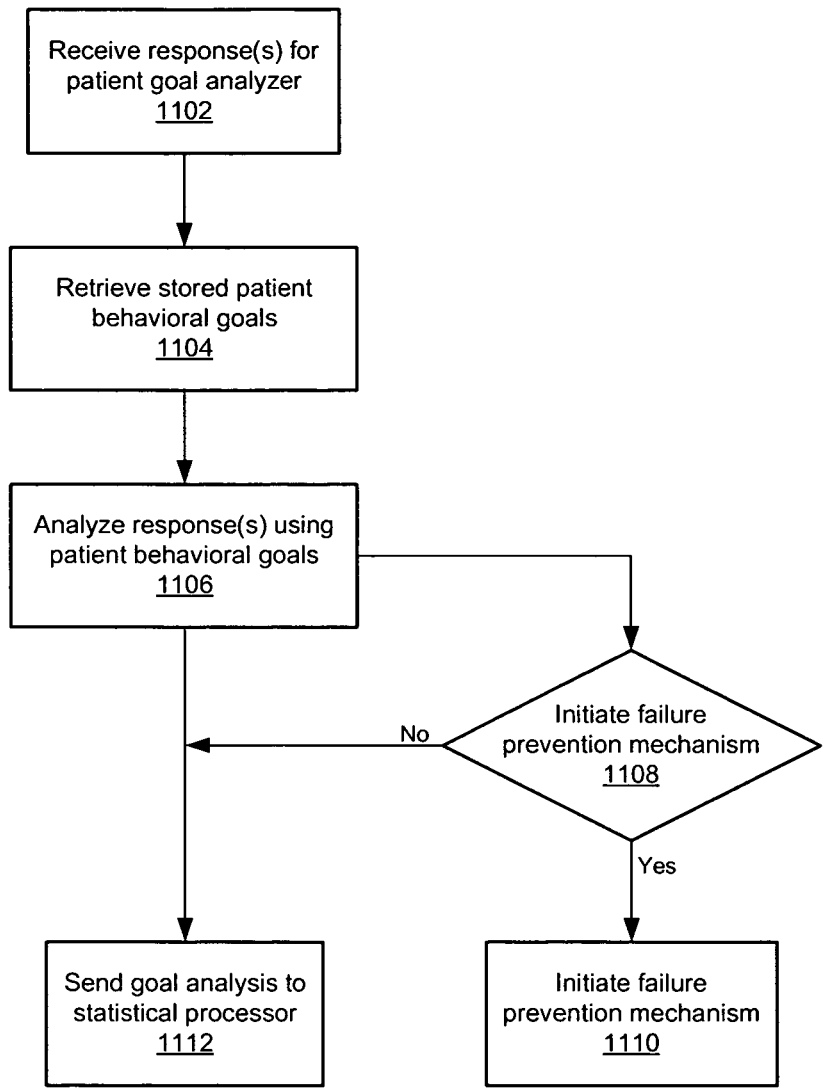
FIG. 11 is a flowchart of one embodiment of analyzing a patient response to a targeted message.

FIG. 11 depicts a flowchart of analyzing a patient's response to a targeted message. In one embodiment, the patient goal analyzer 2126 receives the one or more patient responses from the patient monitoring processor 2120 (Block 1102). When the patient goal analyzer 2126 has received the one or more patient responses from the patient monitoring processor 2120, the patient goal analyzer 2126 then retrieves the stored patient behavioral goals (Block 1104). Alternatively, the patient goal analyzer 2126 could have retrieved the stored patient behavioral goals before receiving the one or more patient responses from the patient monitoring processor 2120. In one embodiment, the patient goal analyzer 2126 retrieves the stored patient behavioral goals from the patient record stored in the patient record database 2126. In another embodiment, the patient goal analyzer 2126 retrieves the stored patient behavioral goals from the statistical profile associated with the patient record stored in the patient record database 2116. In yet another embodiment, the patient goal analyzer 2126 retrieves the stored patient behavioral goals from a patient behavioral goal database. Other types of retrieval are also possible.

After the patient goal analyzer 2126 has received both the one or more patient responses from the patient monitoring processor 2120 and the stored patient behavioral goals, the patient goal analyzer 2126 then performs an analysis on the one or more patient responses using the patient behavioral goals (Block 1106). In one embodiment, the patient goal analyzer 2126 compares the received one or more patient responses with the current behavioral goal. For example, the behavioral objectives could be for the patient to stop smoking entirely. To achieve that objective, there may be multiple intermediates behavioral goals, and the current behavioral goal may be to stop smoking four packs of cigarettes a day. The patient goal analyzer 2126 would been compared to received one or more patient responses with the current goal, being stop smoking four packs of cigarettes a day, and then produce a goal analysis indicating whether the patient is meeting the current behavioral goal. In another example, the behavioral objective could be for the patient to wake up at six o'clock in the morning. To achieve that objective, there may be multiple intermediates behavioral goals, and the current goal in maybe to wake of acts that clock in the morning. The patient goal analyzer 2126 within compare the received one or more patient responses with the current goal, being to wake up at nine o'clock in the morning and then produce a goal and office indicating whether the patient is meeting that current behavioral goal.

In another embodiment, the patient goal analyzer 2126 compares the received one or more patient responses with the set of intermediate goals along the behavioral path. For example, the behavioral objective may be for the patients to stop smoking entirely and there may be multiple intermediates behavioral goals along the behavioral path, such as to stop smoking five packs of cigarettes a day, then to stop smoking three packs of cigarettes a day, then to stop smoking one pack of cigarettes a day, and so forth. In this example, the patient goal analyzer 2126 would compare the received one or more responses with the set of intermediate goals to determine whether the patient is on a forward path in meeting those goals. If the received one or more patient responses indicate that the patient has smoked six packs of cigarettes for the day, the patient goal analyzer 2126 would indicate that the patient is no longer on a forward path to meeting the intermediate behavioral goals. In contrast, if the received one or more patient responses indicate that the patient has smoked to this packs of cigarettes for the day, the patient goal analyzer 2126 would indicate that the patient is on a forward path to meeting the intermediate behavioral goals.

In yet another embodiment, the patient goal analyzer 2126 compares the received one or more patient responses with the behavioral path associated with the patient. For example, the behavioral path may indicate a particular threshold which is considered acceptable to the patient monitoring system 2108. If the received one or more patient responses indicate that the patient is no longer on a net positive progress along the behavioral path the patient goal analyzer 2126 would indicate the failure in the net positive progress.

In yet a further embodiment, the patient goal analyzer 2126 compares the received one or more patient responses with the previously stored one or more patient responses with the stored patient behavioral goals. For example, the patient goal analyzer 2126 may account for the history of all the received one or more patient responses, including, or excluding, the current received one or more patient responses, and based on this history could determine whether the patient has been making progress towards achieving a behavioral goal and/or the behavioral objective. The patient goal analyzer 2126 could also assign priorities to different patient behavioral goals and indicates based on those priorities whether the patient is making progress towards achieving the patient behavioral objective.

After the patient goal analyzer 2126 has analyzed the one and more patient responses, the patient goal analyzer 2126 then communicates with the patient monitoring processor 2120 to determine whether to initiate the failure prevention mechanism 2128 of the patient monitoring system 2108 (Block 1108). The decision to initiate the failure prevention mechanism (Block 1108) may occur concurrently or subsequent to the patient goal analyzer 2126 sending an analysis of the received one or more patient responses to the statistical processor 2122 (Block 1112). If the patient goal analyzer 2126 determines that the received one or more patient responses indicates that the failure prevention mechanism should be initiated, the patient goal analyzer 2126 communicates with the patient monitoring processor 2120 to initiate the failure prevention mechanism (Block 1110) (See FIG. 13). In one embodiment, the decision to initiate the failure prevention mechanism is based on whether the patient has achieved the current behavioral goal. For example, if the current behavioral goal is to stop smoking four packs of cigarettes a day and the received one or more patient responses indicates that the patient has in fact smoked five packs of cigarettes for the day, the patient goal analyzer 2126 would then inform the patient monitoring processor 2120 to initiate the failure prevention mechanism 2128.

In another embodiment, the decision to initiate the failure prevention mechanism 2128 is based on the number of times the patient has failed to meet the current behavioral goal. For example, the patient goal analyzer 2126 may determine that the number of times a patient can fail a current behavioral goal is four times. If the received one or more patient responses indicates that the patients has failed to meet the current behavioral goal more than four times, the patient goal analyzer 2126 would then inform the patient monitoring processor 2120 to initiate the failure prevention mechanism 2128.

In yet another embodiment, the decision to initiate the failure prevention mechanism 2128 is based on whether that the patient has made net progress towards achieving the patient behavioral objective along the behavioral path. For example, if the received one or more patient responses indicate that the patient has not made progress or has made negative progress along the patient behavioral path, the patient goal analyzer 2126 would inform the patient monitoring processor 2120 to initiate the failure prevention mechanism 2128. Where the decision to initiate the failure prevention mechanism is based on a patient making net progress along the patient behavioral path, the patient goal analyzer 2126 could also account for the time elapsed between the last time the patient had net positive progress and the patient's current progress. Other factors the patient goal analyzer 2126 could consider include net failure, the different priorities assigned to the behavioral goals, the amount of time the patient has been on the behavioral path towards achieving the behavioral objective, or other combinations of factors.

Figure 12:
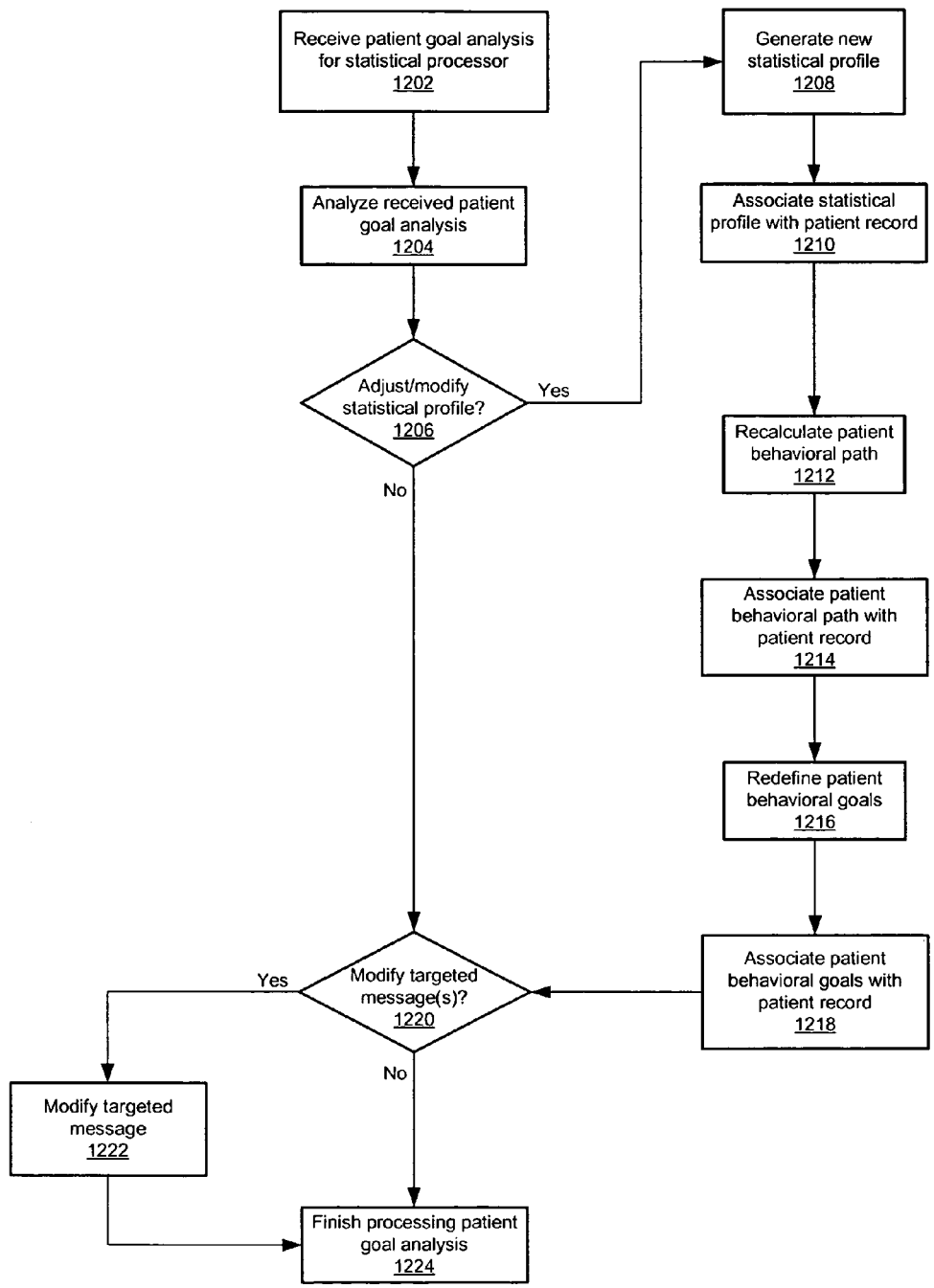
FIG. 12 is a flowchart of one embodiment of modifying a statistical profile.

When the patient goal analyzer 2126 has finished analyzing the received one or more patient responses, the patient goal analyzer 2126 sends the analysis to the statistical processor 2122. FIG. 12 is a flowchart depicting the operations of modifying a statistical profile of the disclosed patient monitoring system according to one embodiment. As shown in FIG. 12, the statistical processor 2122 receives the patient goal analysis from the patient goal analyzer 2126 (Block 1202). The statistical processor 2122 then analyzes the received patient goal analyses (Block 1204). In one embodiment, the statistical processor 2122 analyzes the patient goal analysis to determine whether a selected targeted message elicited a response that indicated progress towards a behavioral goal. For example, if the selected targeted message was "Did you smoke four packs of cigarettes today?", and the goal analysis indicated that the patient had not achieved a particular goal based on this selected targeted message, the statistical processor 2122 would note that the selected targeted message did not help the patient achieve a particular goal. In another example, if the selected targeted message was "You need to stop smoking or you will die!", and the patient goal analysis indicated that the patient had achieved a particular goal based on the selected targeted message, the statistical processor 2122 would indicate that this selected targeted message was helpful for the patient in the achieving a particular goal. In another embodiment, the statistical processor 2122 analyzes the patient goal analysis and the patient record stored in the patient records database 2116. For example, the statistical processor 2122 may analyze the patient's demographic information and compare that with the patient goal analysis to determine whether a selected targeted message or a particular method of treatment is helping that patient meet his/her behavioral goals for that patient in that demographic. In one example, the statistical processor 2122 may analyze the patient's age, and based on that patient's age in conjunction with the received patient goal analysis the statistical processor 2122 may determine whether a selected targeted message is helping a patient of that age achieve a patient behavioral goal. Other demographic, health history and physical exam information may include the patient's nationality, the patient's birthplace, the patient height, diabetes status, the patient's weight, and other such information. In yet a further embodiment, the statistical processor 2122 analyzes health related information of the patient, such as prior medical history, nutritional diet, and physical fitness, with the patient goal analysis to determine whether a selected targeted message or a particular treatment is beneficial in helping the patient achieve the patient's behavioral goal and/or the patient's behavioral objective.

After analyzing the received patient goal analysis (Block 1204), the statistical processor 2122 then determines whether to adjust/modify the statistical profile associated with the patient (Block 1206). In one embodiment, the statistical processor 2122 modifies the statistical profile associated with the patient where the analysis indicates that the patient is meeting a particular behavioral goal. For example, the statistical processor 2122 may modify the statistical profile to indicate that a selected targeted message helps a patient achieve a patient behavioral goal. In another example, the statistical processor 2122 modifies the statistical profile to indicate that a selected targeted message does not help a patient achieve the patient behavioral goal. In another embodiment, the statistical processor 2122 adjusts the statistical profile to include further information that may not have been previously present when the statistical profile was initially created. For example, the statistical processor 2122 may add further information that was not previously accounted for. In one embodiment the statistical processor may add new information reflecting changes to particular data over time acquired through analysis of the patient record database entries for similar patients or for the current patient. For example, through the use of statistical process controls, the statistical processor may update associated population statistical profiles and/or patient statistical profiles associated with one or more patients based on responses to targeted messages, surveys, additional input from the clinician 2102, patient 2104, or external data source 2106, through information requested by the patient monitoring system 2108, or combinations thereof.

In another embodiment the statistical processor may have updated the statistical profiles related to the current patient. Statistical processor 2122 could also remove information that the statistical processor 2122 determines is superfluous or detrimental for the patient. The statistical processor 2122 could determine that the statistical profile associated with the patient should only contain information that helps a patient achieve a patient goal. Alternatively, the statistical processor 2122 may also determine that the statistical profile should contain information about both the failures and successes for the patient in achieving a patient behavioral goal.

The statistical profile could also reflect the treatments and/or the selected targeted message that are beneficial in achieving a patient behavioral objective. The modifications to the statistical profile may also reflect the treatment analysis or the selected targeted message that are detrimental in achieving a patient behavioral objective. Furthermore, the statistical processor 2122 may also modify the statistical profile based on demographic or condition for a particular group of patients. For example, if the patient monitoring system 2108 is monitoring several patients, the statistical processor 2122 may determine that a particular exercise is more beneficial than a comparative exercise based on response received for those particular patients. The statistical processor 2122 may then incorporate this knowledge into future questions or questionnaires to prompt other monitored or future patients.

In adjusting/modifying the statistical profile associated with the patient, the statistical processor 2122 may generate a new statistical profile for the patient based on the analysis of the patient goal analysis (Block 1208). Generating a new statistical profile may include retaining the old statistical profile, supplementing the old statistical profile, removing the old statistical profile, or a combination thereof. After generating a new statistical profile (Block 1208), the statistical processor 2122 associates the generated statistical profile with the patient record of the received patient goal and analysis (Block 1210). The statistical processor 2122 then communicates with the patient behavioral calculator 2124 to recalculate the patient behavioral path (Block 1212). Alternatively, the patient behavioral calculator 2124 may determine not to recalculate the patient behavioral path based on the generated statistical profile. The patient behavioral calculator 2124 then proceeds to associate the patient behavioral path with the patient record (Block 1214) and to redefine the patient behavioral goals (Block 1216). The patient behavioral calculator 2124 then associates the patient behavioral goals with the patient record for the received patient goal analysis (Block 1218).

After determining whether to adjust/modify the statistical profile associated with the received patient goal analysis (Block 1206), the statistical processor 2122 then determines whether to modify the selected targeted message(s) or select one or more different messages sent to the patient (Block 1220). In an alternative embodiment, the clinician 2102 could instruct the statistical processor 2122 to modify the selected target message(s), or to select one or more different messages. In one embodiment, the statistical processor 2122 analyzes the targeted message(s) sent to the patient based on the received patient goal analysis and modifies a selected targeted message (Block 1222), if necessary. For example, if the selected targeted message sent to the patient was "Keep up the great job!", and the analysis of the patient goal analysis indicated that this selected targeted message did not help the patient achieve the patient behavioral goal and/or the patient behavioral objective, the statistical processor 2122 may modify the selected targeted message from "Keep up the great job!" to "I am very disappointed in you."

In another embodiment, the statistical processor 2122 also modifies the type and/or tone of the selected targeted message sent to the patient. For example, if the selected targeted message sent to the patient was "Did you smoke four packs of cigarettes today?", and the analysis of the patient goal analysis indicated that this selected targeted message did not help the patient achieve a patient behavioral goal analysis or the patient behavioral objective, the statistical processor 2122 may modify the selected targeted message from "Did you smoke four packs of cigarettes today?" to "You need to stop smoking four packs of cigarettes!"

In yet another embodiment, the statistical processor 2122 modifies future targeted messages for the patient. For example, if the statistical processor 2122 determines that a type of targeted message, such as a positive reinforcement targeted message, is not helping the patient to achieve a patient behavioral goal and/or a patient behavioral objective, the statistical processor 2122 may change future targeted messages to negative reinforcement targeted messages. Other types of modifications to future targeted messages include modifying the quantity mentioned in the targeted message, modifying the subject of the targeted message, or of the targeted message.

In yet a further embodiment, the statistical processor 2122 modifies the targeted messages where the statistical processor 2122 decides to adjust/modify the statistical profile associated with the patient record. For example, a newly generated statistical profile based on adjustments and/or modifications by the statistical processor 2122 may require a new set, or a different set, of targeted messages for the patient. Once the statistical processor 2122 has finished modifying the targeted messages 1222, the statistical processor 2122 then finishes processing the patient goal analysis (Block 1224). For example, the statistical processor 2122 may inform the patient monitoring processor that it has finished processing the patient goal analysis.

Figure 13:
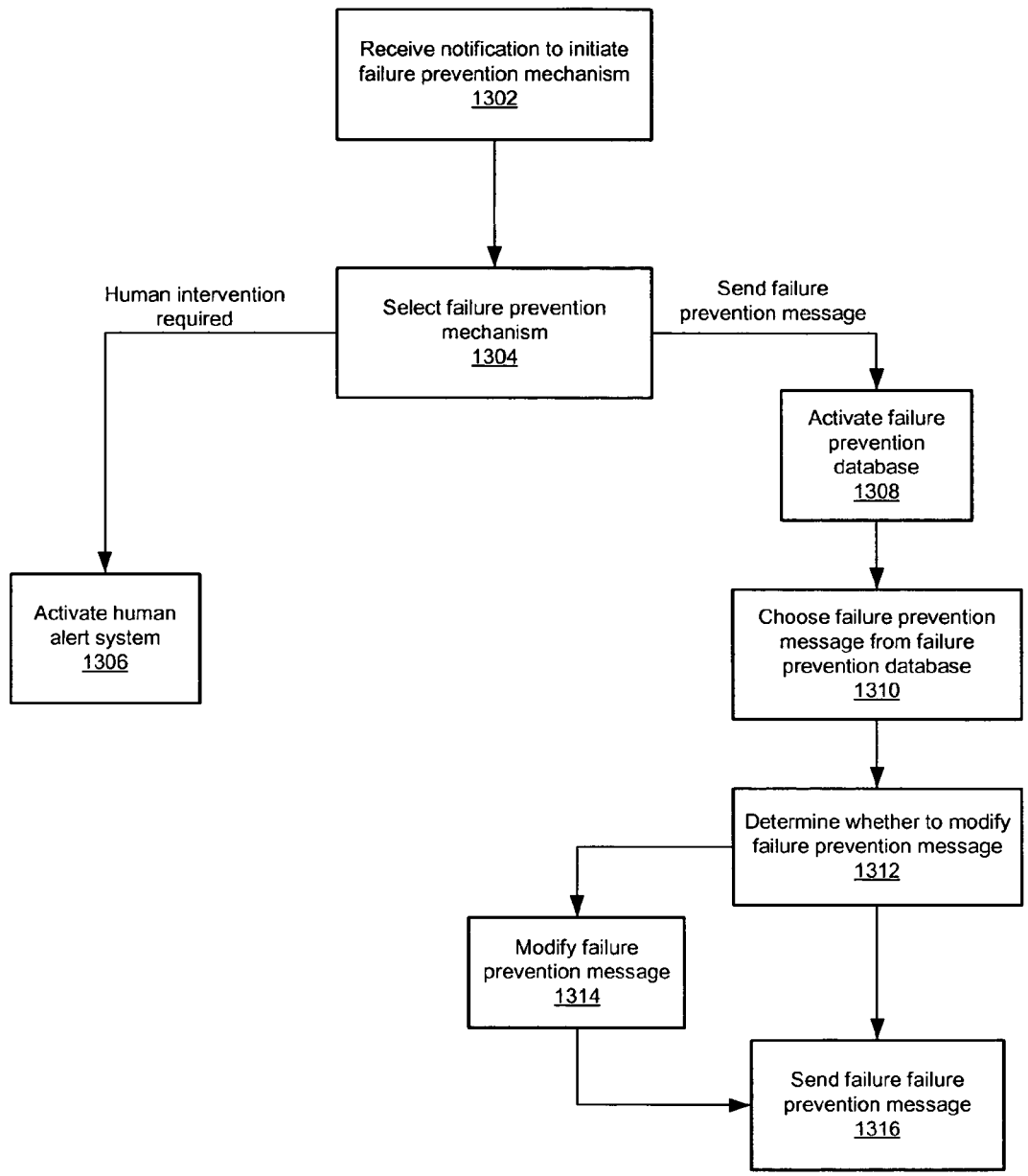
FIG. 13 is a flowchart of one embodiment of activating a failure prevention mechanism.

Referring to FIG. 13 is a flowchart for activating a failure prevention mechanism 2128 of the patient monitoring system 2108. The failure prevention mechanism 2128 of the patient monitoring system 2108 is a mechanism designed to prevent a patient from failing to achieve a behavioral objective and/or a particular behavioral goal along the behavioral path to the behavioral objective. In one embodiment, the failure prevention mechanism 2128 is a human alert system (See FIG. 23A). In another embodiment, the failure prevention mechanism 2128 is a failure prevention database (See FIG. 23B). According to the embodiment shown in FIG. 13, the patient monitoring processor 2120 receives notification to initiate the failure prevention mechanism 2128 (Block 1302). For example, the patient monitoring processor 2120 may receive a notification to initiate the failure prevention mechanism 2128 from the patient goal analyzer 2126. After receiving a notification to initiate the failure prevention mechanism 2128 (Block 1302), the patient monitoring processor 2128 then selects a failure prevention mechanism 2128 (Block 1304).

In one embodiment, the patient monitoring processor 2120 selects both the human alert system and the failure prevention database. In another embodiment, the patient monitoring processor 2120 selects the failure prevention mechanism 2128 based on predefined criteria. The predefined criteria includes factors such as the number of times the patient has failed to meet a behavioral goal, the total number of times the patient has failed to meet a behavioral goal, the severity of failing to meet a behavioral goal, whether the patients is no longer on the behavioral path, or a combination thereof. Other factors may also account for the demographic of the patient, the patient's history in achieving a behavioral objective, whether the patient record indicates a patient preference for a particular failure prevention mechanism 2128, or whether the patient requires human intervention.

The clinician 2102, in establishing the patient record, may also indicate whether the patient monitoring processor 2120 selects the human alert system or the failure prevention database as the failure prevention mechanism 2128. Once the patient monitoring processor 2120 has selected a failure prevention mechanism 2128, the patient monitoring processor 2120 then activates that failure prevention mechanism 2128. If the patient monitoring processor 2120 decides that human intervention is required, the patient monitoring processor 2120 then activates the human alert system as the failure prevention mechanism 2128 (Block 1306) (See above with reference to FIG. 23A). If the patient monitoring processor 2120 decides to send a failure prevention message, the patient monitoring processor 2120 then activates the failure prevention database as the failure prevention mechanism 2128 (Block 1308) (See above with reference to FIG. 23B).

After the patient monitoring processor 2120 has activated the failure prevention database (Block 1308), the patient monitoring processor 2120 then chooses a failure prevention message from the failure prevention database (Block 1310).

In an alternative embodiment, a separate failure prevention processor communicates with the patient monitoring processor 2120 to choose a failure prevention message from the failure prevention database. In one embodiment, choosing a failure prevention message from the failure prevention database is based on the severity of the patient in failing to achieve a particular behavioral goal and/or a behavioral objective. For example, if the patient goal analyzer 2126 communicates to the patient monitoring processor 2120 that the patient failed to achieve a particularly significant behavioral goal, the patient monitoring processor 2120 would then select a failure prevention message that communicates this severity, such as "You missed a really important goal and you need to continue in working towards that goal." In another embodiment, choosing a failure prevention message from the failure prevention database is based on the number of times a patient has failed to achieve a particular goal and/or a behavioral objective. For example, the failure prevention messages stored in the failure prevention database may be rated in severity and the rating may correspond to the number of times at patient has failed to meet a goal. In yet another embodiment, choosing a failure prevention message from the failure prevention database is sequentially based such that each failure prevention message is guaranteed to be sent at least once to the patient depending on the number of failures by the patient.

Before the failure prevention is sent, the patient monitoring processor 2120, or other failure prevention processor, determines whether to modify the failure prevention message (Block 1312). In one embodiment, the failure prevention messages are purposely generic but are tailored to the unique demographics of the patient before sending. In another embodiment, the failure prevention messages are modified to correspond to the severity of the failure by the patient in failing to achieve a behavioral goal and/or behavioral objective. The modifications to the failure prevention message could also be based on a temporal basis, such as adding or removing words that reflect the day, week, or month on which the failure prevention message was sent. Modifications to the failure prevention message may include, but are not limited to, additions, deletions, edits, insertions, or other modifying actions. The failure prevention message could also be modified to reflect personal information of the patient, such as the patient's name, home address, prior medical history, other personal information, or combination thereof. Once the patient monitoring processor 2120 has determined to modify a failure prevention message, the failure prevention message is then modified (Block 1314).

After a determination has been made as to whether to modify a failure prevention message (Block 1312), the patient monitoring system 2108 sends the failure prevention message (Block 1316). In one embodiment, the failure prevention message is an audible message sent to the patient 2104 over communication link 2132. For example, where the patient 2104 communicates with the patient monitoring system 2108 using an IVR interface, the failure prevention message would be sends as an audible message to the patient 2104. In another embodiments the failure prevention message is an audible and/or visual message sent to the patient 2104 over communication link 2132 such as where the patient 2104 communicates with the patient monitoring system 2108 using an interface designed for the Internet, such as a web page of a web site. In yet another embodiment, the failure prevention message is sent to the patient after the patient has finished the patient monitoring session with the patient monitoring system 2108. The failure prevention message could also be sent while the patient is communicating with the patient monitoring system 2108. The patient 2104 may also have the option of selecting when to receive the failure prevention message.

Figure 14:
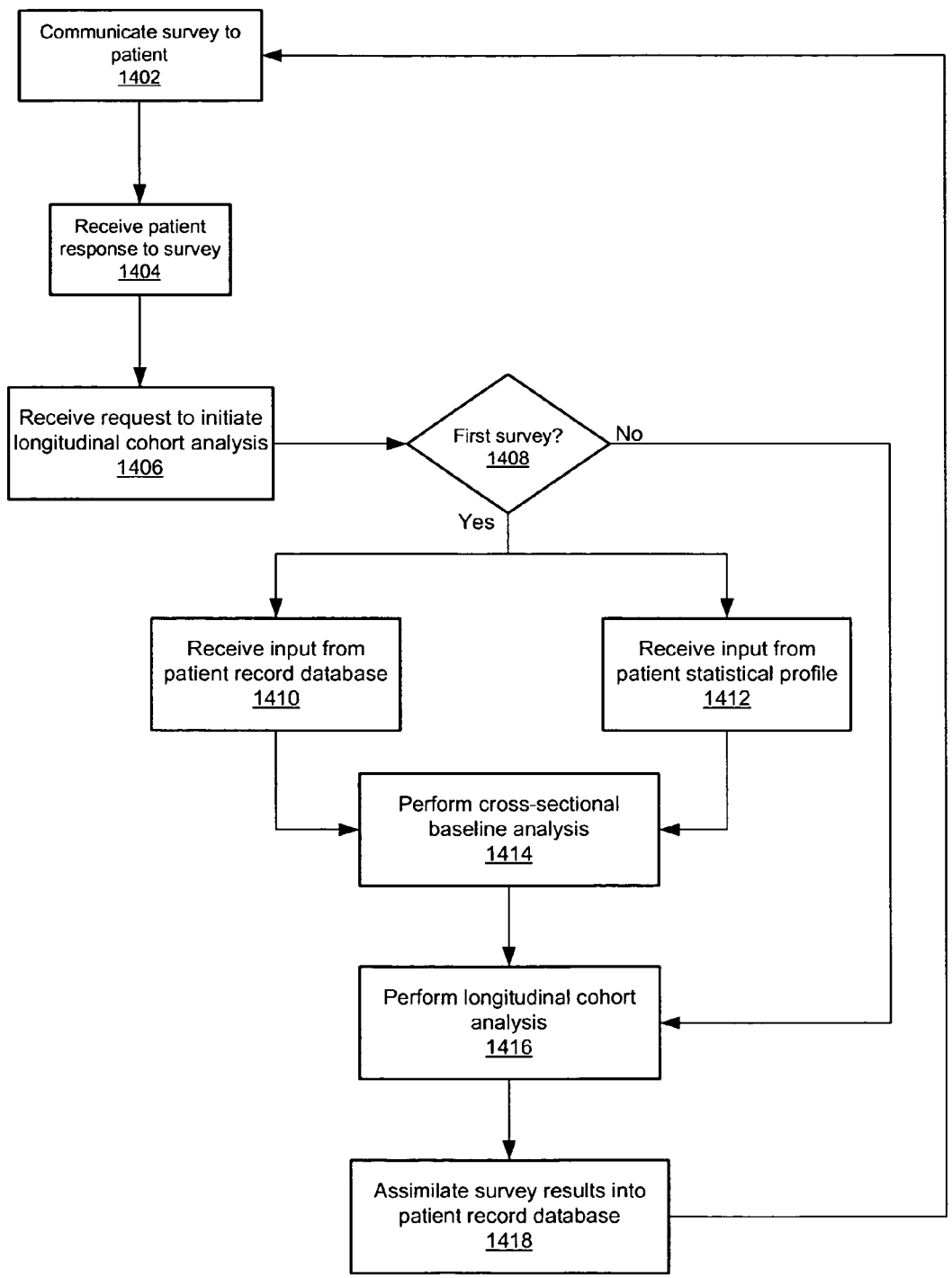
FIG. 14 is a flowchart of one embodiment of evaluating patient input using a statistical processor.

FIG. 14 is a flowchart of one embodiment of evaluating patient input using a statistical processor. The information communication processor 2112 communicates the survey to the patient 2104 according to the patient statistical profile 2130 (Block 1402) and receives the patient response to the survey (Block 1404). The survey communicated to the patient 2104 may contain one or more patient questionnaires associated with the patient record of the patient 2104. After receiving the patient response to the survey (Block 1404), the statistical processor 2122 receives a request from the patient monitoring processor 2120 to initiate a longitudinal cohort analysis (Block 1406). The statistical processor 2122 queries the patient monitoring processor 2120 to determine whether this is the first survey data for the patient 2104 using the current patient statistical profile 2130 (Block 1408). If this is the first survey, the statistical processor 2122 requests data from the patient record database 2116 (Block 1410) and from the patient statistical profile 2130 (Block 1412). The statistical processor uses input from patient record database 2116, the patient statistical profile 2130, or a combination thereof, to perform a cross-sectional baseline analysis (Block 1414), as explained below with reference to FIG. 15. In an alternative embodiment, a baseline analysis is performed (Block 1414) after any subsequent survey. After a baseline analysis has been performed (Block 1414), a longitudinal cohort analysis is then performed (Block 1416), as explained below with reference to FIG. 16. In an alternative embodiment, the longitudinal cohort analysis is performed if the survey communicated to the patient is not the first survey. After completing the longitudinal cohort analysis (Block 1416), survey results are assimilated into the patient record database 2116 (Block 1418).

In one embodiment, the patient monitoring processor 2120 directs the information communication processor 2112 to communicate a survey to the patient 2104 and receive the patient responses (Block 1404). The patient monitoring processor 2120 may then store the results in the patient record database 2116. The patient monitoring processor 2120 then requests the statistical processor 2122 to initiate the longitudinal cohort analysis (Block 1406). In an alternative embodiment, the clinician 2102, the patient 2104, the external data source 2106, or a combination thereof, instructs the statistical processor 2122 to initiate the longitudinal cohort analysis (Block 1406).

In one embodiment, the appropriate cohort set includes all subjects who share one or more characteristics that are related to either possible patient behavioral interventions or to desirable outcomes. In an alternative embodiment, the appropriate cohort set includes only a subset of patients who share one or more characteristics that are related to either possible patient behavioral interventions or to desirable outcomes. The appropriate cohort set is then stored in the statistical profile of the patient. In one embodiment the appropriate cohort may be identified by the system automatically based on the outcome of interest, treatment options, and the associated statistical profile. In another embodiment the appropriate cohort may be entered by the clinician 2102 directly, received from an external data source 2106, assigned a default value by the system 2108, or a combination thereof.

If the current survey is the first survey for the current patient, the statistical processor 2122 requests patient data from the patient monitoring processor 2120 for both the current patient and the appropriate cohort of patients, which abstracts the appropriate data from the patient record database 2116, reformats the data if necessary and forwards it to the statistical processor 2122. The statistical processor 2122 then performs a cross-sectional baseline analysis (Block 114) to determine whether the patient statistical profile should be changed, whether the appropriate cohort set should be changed and whether the patient behavioral goals should be recalculated.

Figure 15:
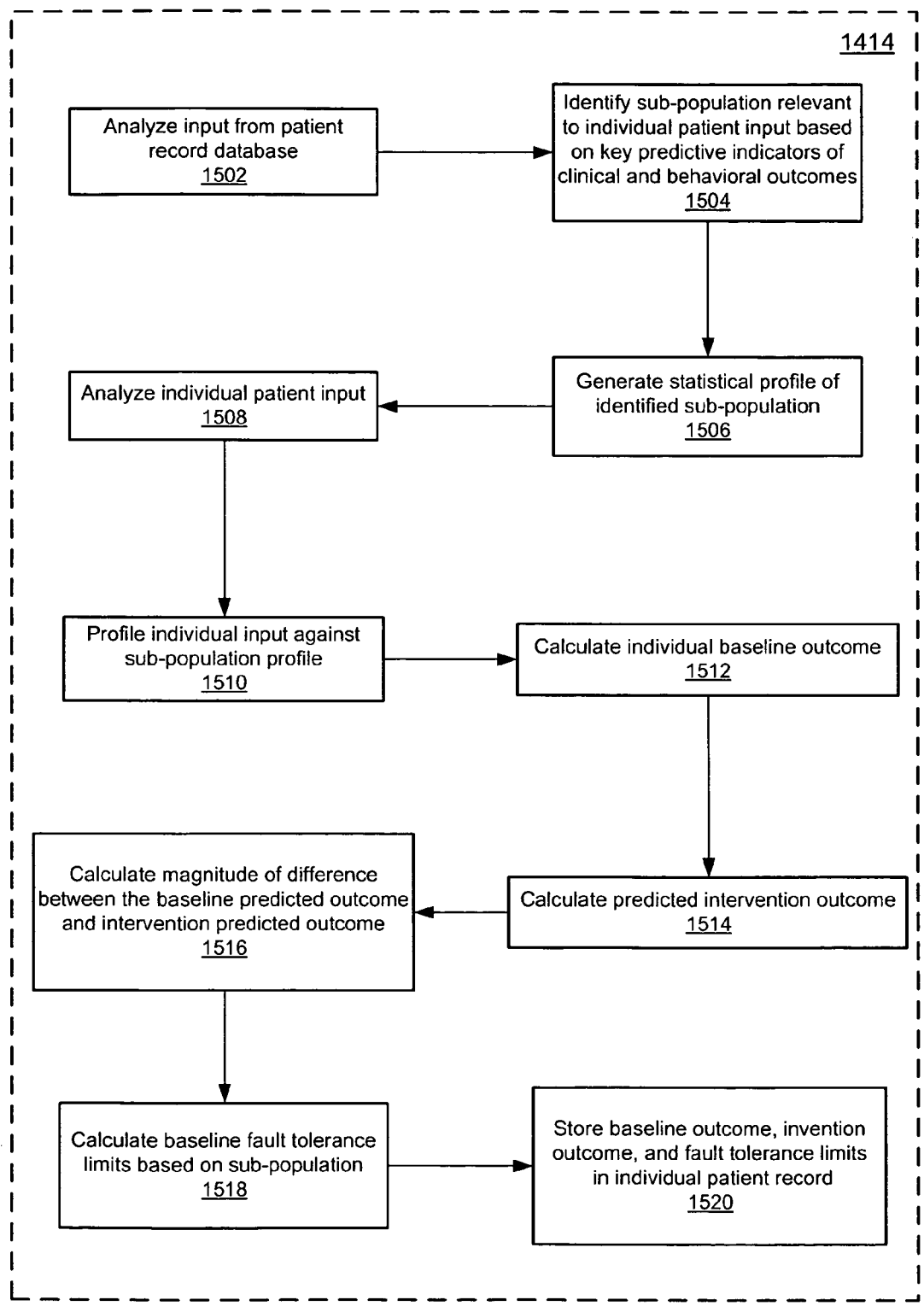
FIG. 15 is a flowchart of one embodiment of the statistical processor performing a cross-sectional baseline analysis.

FIG. 15 is a flowchart depicting operation of the statistical processor 2122 performing a cross-sectional baseline analysis according to one embodiment. In one embodiment, the input from the patient record database 2116 is analyzed (Block 1502) to automatically determine the appropriate cohort or sub-population for the current patient based on predictors of clinical and behavioral outcomes associated with the outcomes (Block 1504). In an alternate embodiment, these predictors are contained in the statistical profile 2130 for the current patient. In a further embodiment, these predictors are stored in the patent record database 2116. For example, if the desired outcome is related to a combination of lipid value goals, the characteristics identifying the cohort would include sex, diabetic status and statin usage as well as other predictors. A statistical profile of the cohort is then generated (Block 1506). This profile contains descriptions of the distributions of medical and behavioral outcome measures, including but not limited to, mean, standard deviation and percentiles of those distributions after appropriate transformations for continuous measures and percentages by category for categorical outcomes.

Input from the individual patient record is analyzed (Block 1508) and is profiled against the cohort profile (Block 1510). In one embodiment, the profile is limited to those predictors that are available for the current patient. In another embodiment, an imputation method, such as a model-based imputation, hot deck imputation, imputation to the mean or median or multiple imputations, are used to impute values that are missing in the current patient record.

Profiling may involve one or more medical or behavioral outcome measures, which in turn may be either continuous or categorical. Profiling, in one embodiment, may treat each outcome individually while another may treat them as a single multivariate outcome. For example, diabetes status may treated alone, but systolic and diastolic blood pressure may be treated as a single two-dimensional outcome. Continuous outcomes might be profiled using predictive modeling, including but not limited to methods such as generalized linear models, generalized mixed effects models, generalized estimating equations, time series models, tree-structured regression, Bayesian models, nearest neighbor methods, clustering or scaling algorithms or neural networks. Categorical models might be profiled using some of the same methods mentioned for continuous outcomes where appropriate, but might also include other techniques, including but not limited to discriminate analysis, Bayesian classifiers and tree-structured classifiers.

Individual baseline outcomes are then calculated (Block 1512). In one embodiment, these are calculated based on the predictive relationships determined when generating the statistical profile of the cohort (Block 1506). In another embodiment, these are calculated based on statistical profiles of patients derived from relevant literature. A third embodiment uses predictive relationships on advice solicited from an expert panel. Another embodiment combines the two or more approaches depending upon the nature of the outcomes and the strength of the evidence in the literature, expert panel or patient record database. Hence, the contribution of the patient record database grows with the number of subjects captured in it. Techniques for determining combining proportions may include, but are not limited to, fixed proportions, proportions based upon an information measure, any now known or later developed technique, or combination thereof. In one embodiment, the baseline outcome is a single number or category for each outcome measure. In another embodiment, the outcomes are probability distributions for each outcome measure, whether continuous, categorical, multivariate, or combination thereof.

Individual predicted intervention outcomes are then calculated (Block 1514). These are similar to the baseline outcomes, except that the impact of the intervention is factored into the calculation. These outcomes may be calculated individually for each medical and behavioral outcome or may be calculated jointly, as a single multivariate outcome. In one, embodiment this involves fitting new models as in calculating the individual baseline outcome (Block 1512), but restricting the cohort to subjects who complied with the planned intervention. In another embodiment, this involves including predictors that track with the active intervention. For subjects in the cohort that are missing information on interventions or compliance, models might include imputation, multiple imputation, or combinations thereof. As with individual baseline outcomes, predicted intervention outcomes may be a single number or may be probability distributions, indicating the likelihood of a variety of outcomes.

After calculating the predicted intervention outcome (Block 1514), the predicted difference between the baseline predicted outcome and the intervention predicted outcome is calculated (Block 1516). This difference may be calculated as a difference in value for a numerical measure, a difference in category, as a probability distribution for a difference in numerical or categorical outcome, or a combination thereof. In one embodiment, the difference is a single number derived from the difference of the individual baseline outcome and the predicted intervention outcome. In another embodiment, the difference is modeled directly. For example, a mixed effect model may be used to estimate the difference in rate of change over time resulting from an intervention. In another embodiment, a Bayesian predictive model is used to estimate the probability distribution of values over time based on the presence or absence of an intervention. In yet another embodiment, a Markov model is used to predict probabilities of a variety of possible outcome classes as a function of time and other predictors.

Baseline and predicted intervention fault tolerances are then calculated (Block 1518). In one embodiment, fault tolerances are derived from predictive models using model-based estimates of variability. In another embodiment, bootstrap analyses is used to estimate variability of estimates based on the cohort. In another embodiment, jackknife or split sample techniques (such as using a training and test sample approach) are used to estimate variability. Another embodiment uses a combination of some or all of the above approaches.

The baseline outcome, intervention outcome and fault tolerance limits are then stored in the individual patient record (Block 1520). The statistical processor communicates the requested results to the patient monitoring processor 2120, which then stores the information in the patient record database 2116.

Figure 16:
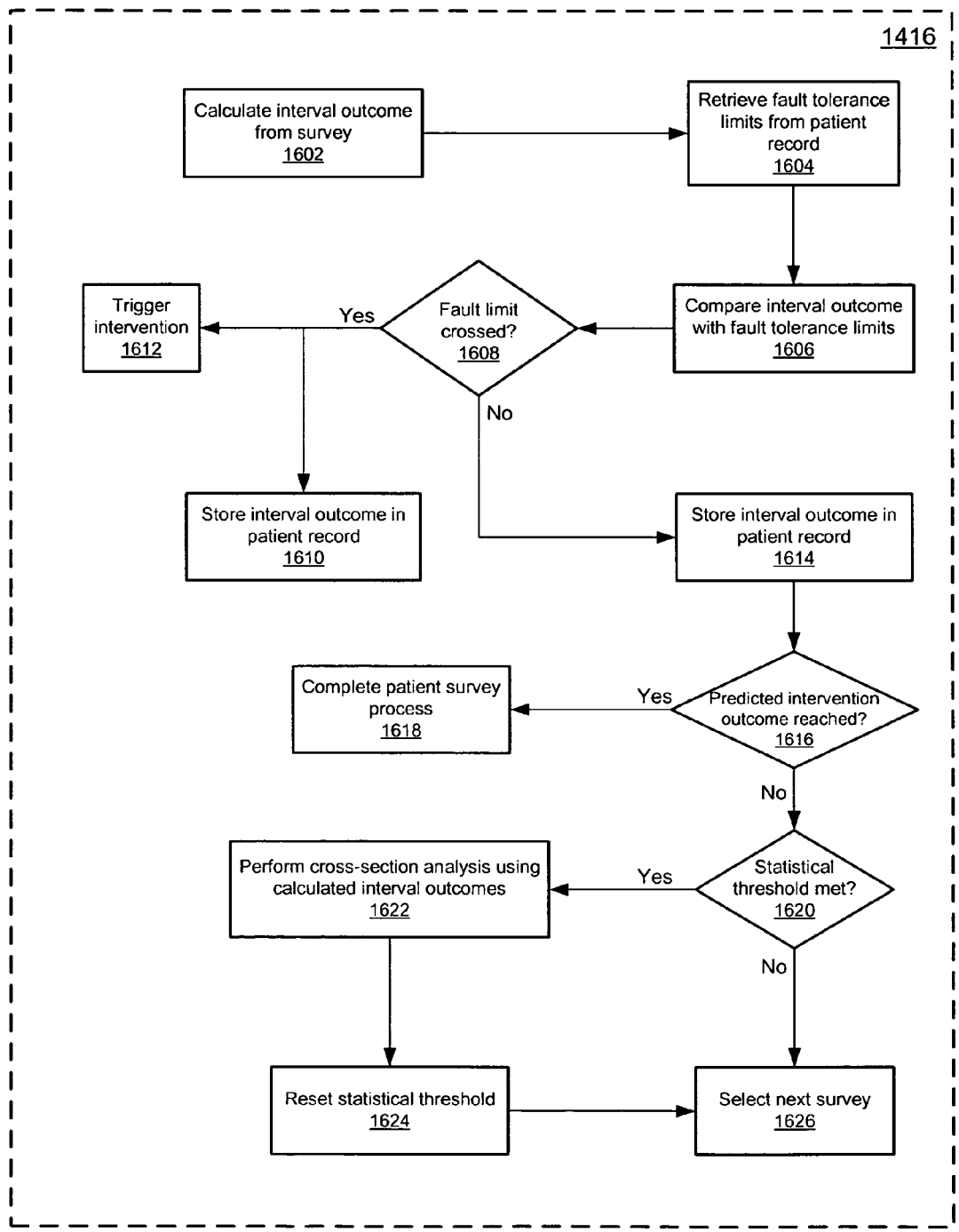
FIG. 16 is a flowchart of one embodiment of the statistical processor performing a longitudinal cohort analysis.

FIG. 16 is a flowchart depicting operation of the statistical processor 2122 performing a longitudinal cohort analysis according to one embodiment. The longitudinal cohort analysis begins by assessing the interval outcome of the patient based on the survey data (Block 1602). The fault tolerance limits are retrieved from the patient record (Block 1604), and these are compared with the interval outcome (Block 1606). The comparison of the interval outcome with the fault tolerance determines whether the fault limit has been crossed (Block 1608). If a fault limit has been crossed, then an intervention is triggered (Block 1612), and the interval outcome is stored in the patient record database 2116 (Block 1610). If a fault limit is not crossed, the interval outcome is stored in the patient record database 2116 (Block 1614), and an assessment occurs to determine whether the predicted intervention outcome has been reached (Block 1616). If the outcome has been reached, the patient survey process is completed (Block 1618). For example, if the predicted intervention outcome is to stop a patient from smoking and the statistical processor 2122, or other processor, determines that the patient has reached this predicted intervention outcome based on the patient's responses to the one or more surveys presented, the statistical processor 2122, or other processor, discontinues presenting surveys to the patient.

If the predicted intervention outcome has not been reached, such as where the statistical processor 2122 determines that the patient is continuing to smoke, the interval outcome is assessed to determine if one of the statistical thresholds has been met (Block 1620). For example, if the statistical threshold is that the patient is to reduce smoking down to five cigarettes a day, and the statistical processor 2122, or other processor, determines that the patient has reduced smoking down to 3 cigarettes day, the statistical processor 2122, or other processor, will determine that the statistical threshold has been met. As another example, a statistical threshold may be that the patient is to reach the predicted intervention outcome of not smoking within four sessions with the patient monitoring system 2108. If a threshold has been met, such as where the statistical processor 2122, or other processor, has determined that the patient is at his or her fifth session, a cross-section analysis based on the current interval outcome is calculated (Block 1622), and the statistical threshold is reset (Block 1624). The next survey may then be selected irrespective of whether the statistical threshold was met (Block 1626). In this fashion, a patient may proceed towards the predicted intervention outcome until the statistical processor 2122, or other processor, determines that the patient has met the predicted intervention outcome.

The comparison of the interval outcome with fault tolerance limits (Block 1606) may occur in a variety of ways. In one embodiment, the comparison is a simple comparison of a final value to a higher and lower boundary. In another embodiment, the comparison of the interval outcome with the fault tolerance limits stored in the patient record database 2116 follow process control guidelines, where various rules related to observations falling a certain distance above or below the mean result in a triggering event. In another embodiment, fault tolerance limits are related to stopping boundaries, such as O'Brien-Fleming boundaries or Pocock-boundaries, as those are used in clinical trials based upon spending functions. In another embodiment, the comparison is Bayesian model-based, with updated posterior distributions crossing a distributional tolerance limit.

The comparison of the interval outcome to the intervention outcome (Block 1616) may occur similar to the comparison with tolerance limits (Block 1606). Alternatively, the comparison may involve the comparison of the most recent value in the interval with a value indicating success. The comparison of the interval outcome with the statistical threshold (Block 1620) may also occur similar to the comparison with the fault tolerance limits (Block 1606).

Figure 17:
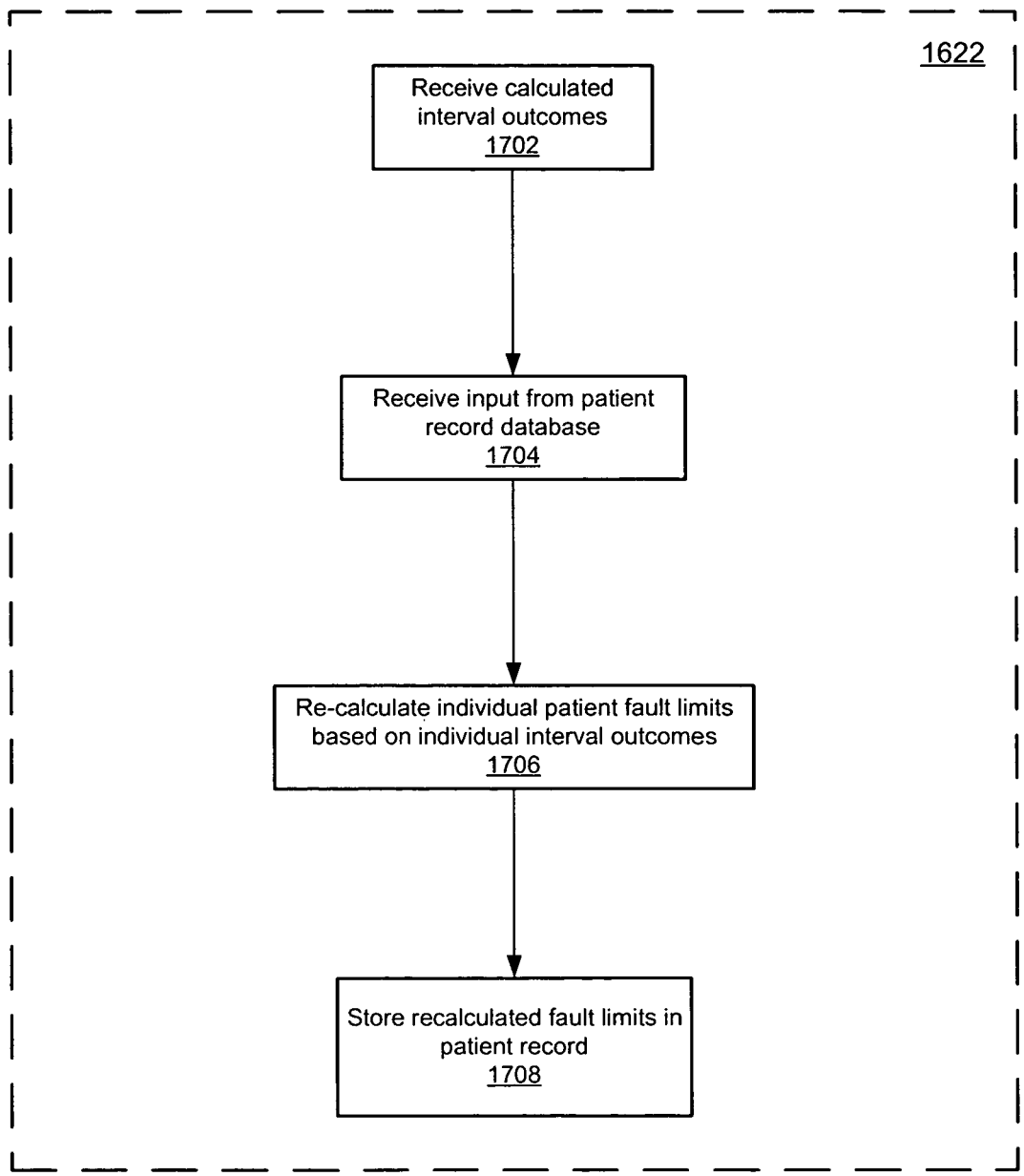
FIG. 17 is a flowchart of one embodiment of the statistical processor performing a cross-sectional analysis using calculated interval outcomes.

If a statistical threshold is met without reaching the intervention outcome, the behavioral goal is adjusted (Block 1622). FIG. 17 is a flowchart depicting operation of the statistical processor 2122 performing a cross-sectional analysis using calculated interval outcomes to adjust the behavioral objective according to one embodiment. The statistical processor 2122 first receives the calculated interval outcomes (Block 1702) and input from the patient record database 2116 relating to the interval outcomes (Block 1704). It is possible that the information stored in the patient record database 2116 will have changed since the previous cross-section baseline analysis. The statistical processor 2122 then uses the information from the patient record database 2116 and the calculated interval outcomes to calculate new fault limit values (Block 1706). In one embodiment, new fault limits are calculated using Bayesian averaging of a variability estimate from the patient record database 2116 together with an estimate derived from the interval outcome. In another embodiment, the new fault limits are based on a variability estimate derived from the interval outcome alone. The new fault limits are then stored in either the patient record database 2116, the patient statistical profiles 2130, or a combination thereof (Block 1708).

Referring back to FIG. 14, the assimilation of survey results into the patient record database 2116 (Block 1418) may occur in a variety of ways depending upon the type of survey data. For example, if data is received from an external data source 2106, such as a remote blood sugar monitor, this information may be stored directly in the patient record database 2116. If data is received from a an external data source 2106, derivative measures may also be calculated and stored. For example, a remote blood pressure monitor may report systolic and diastolic blood pressure, with pulse pressure calculated from these two and stored along with them. Alternatively, if data is received in the form of responses to a questionnaire, the raw responses, normalized responses, transformed responses, or scales and subscales, or combinations thereof may be stored in the patient record database 2116. The choice of assimilation method will vary from one embodiment to another and depend upon the type of data collected.

Figure 18:
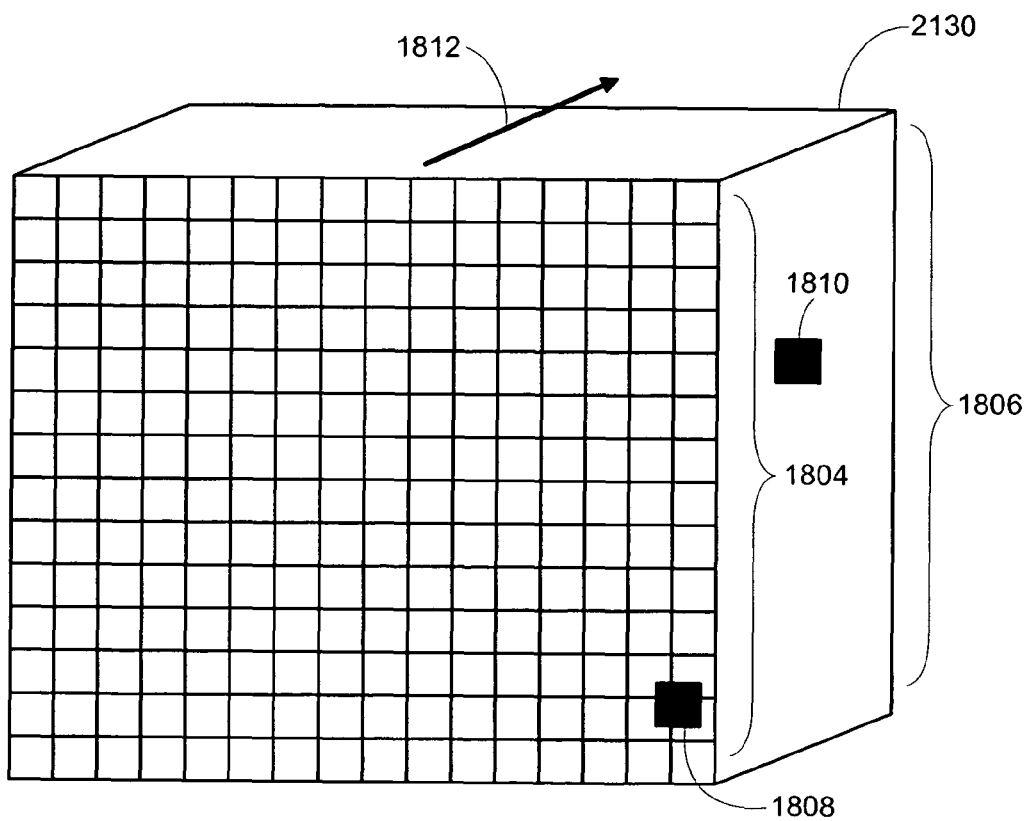
FIG. 18 is a graphical illustration of one embodiment of the patient statistical profiles.

FIG. 18 is a graphical illustration of one embodiment of the patient statistical profiles 1930 showing the time 1812 of a patient in moving from a baseline set of cohorts 1804 to a another set of cohorts 1806 associated with a predicted intervention outcome profile 1810. As explained above with reference to FIG. 15, when an enrolled patient answers the first survey, the statistical processor 2122 determines the baseline cohort set 1804 and profiles the patient provided responses to the first survey against the baseline cohort set 1804 to determine a baseline patient statistical profile 1808. Alternatively, or in addition to the answers provided by the patient 2104 in answering the first survey, the statistical processor 2122 may use previously provided information, such as from information stored in the patient record database 2116, to determine a baseline cohort set 1804 and a baseline patient statistical profile 1808. In another embodiment, the statistical processor 2122 may use statistical information provided by the clinician 2102, the patient 2104, or an external data source 2106, or combinations thereof, to determine the baseline cohort set 1804 and the baseline statistical profile 1808.

The statistical processor 2122 then calculates the predicted intervention outcome profile 1810. The statistical processor 2122 then calculates the difference between the baseline patient statistical profile 1808 and the predicted intervention outcome profile 1810. Based on the difference between the baseline patient statistical profile 1808 and the predicted intervention outcome profile 1810, the statistical processor 2122 is able to calculate a patient behavioral path to help the patient 2104 achieve the predicted intervention outcome profile 1810 and the set of patients 1806 associated with the predicted intervention outcome profile 1810.

Figure 19:
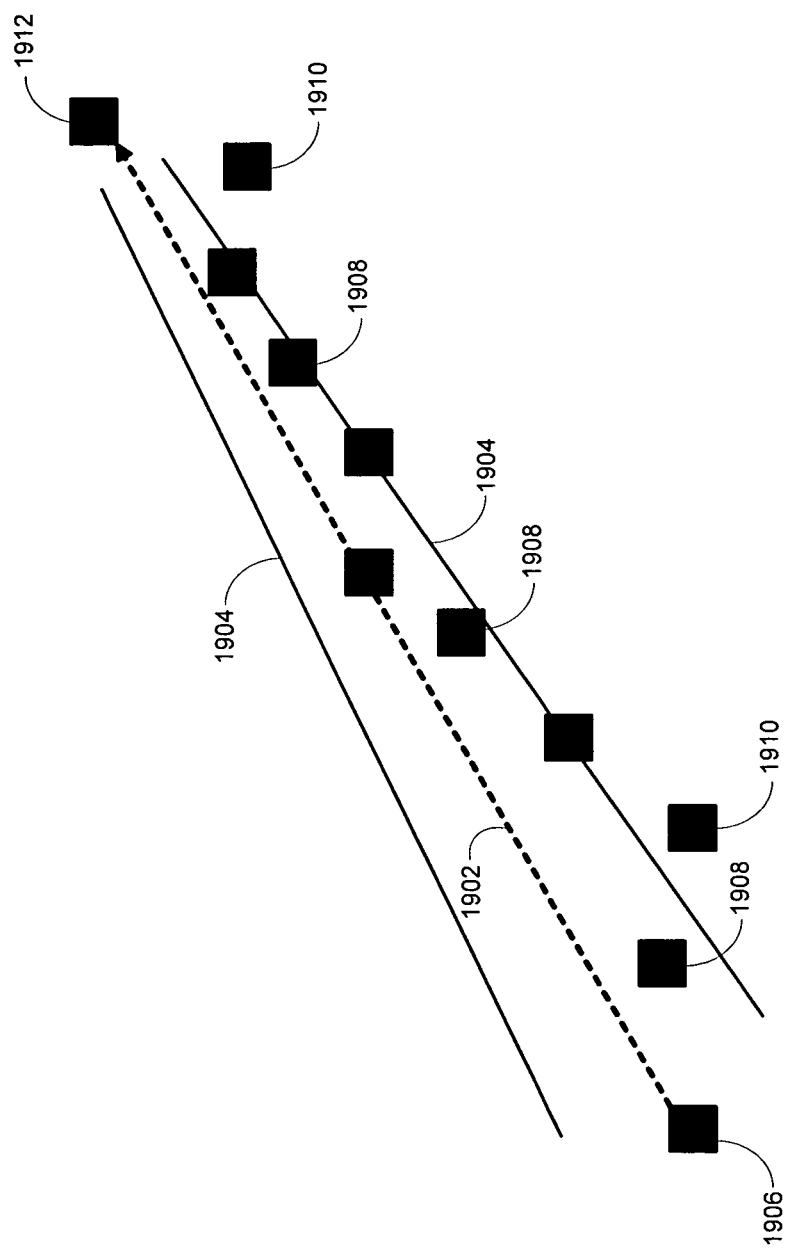
FIG. 19 is a diagram of one embodiment of a behavioral path.

FIG. 19 is a diagram of one embodiment of a patient behavioral path 1902. As described above with reference to FIG. 15, when the patient 2104 completes a first survey, the statistical processor 2122 calculates a baseline outcome 1906 based on the patient responses to that first survey. The statistical processor 2122 then calculates a patient behavioral path 1902 and a predicted intervention outcome 1912. Using the population cohort set, the statistical processor 2122 then calculates fault tolerance limits 1904 between the baseline outcome 1906 and the predicted intervention outcome 1912. As the patient 2104 completes each survey, the statistical processor 2122 calculates an interval outcome 1908 and compares the interval outcome 1908 with the fault tolerance limits 1904. Where the statistical processor 2122 calculates an interval outcome 1910 outside the fault tolerance limits 1904, the statistical processor 2122 triggers the failure prevention mechanism 2128. As the patient 2104 completes surveys, the statistical processor 2122 may re-calculate the fault tolerance limits 1904 based on the responses provided by the patient to those surveys. As shown in the embodiment of FIG. 19, the fault tolerance limits 1904 decrease as the statistical processor 2122 calculates each subsequent interval outcome 1908. Alternatively, the fault tolerance limits 1904 may also increase, or otherwise vary, as the patient 2104 answers each survey. The alterations in the fault tolerance limits 1904 encourage the patient 2104 to proceed along the patient behavioral path 1902 until the patient reaches the predicted intervention outcome 1912.

Figure 20:
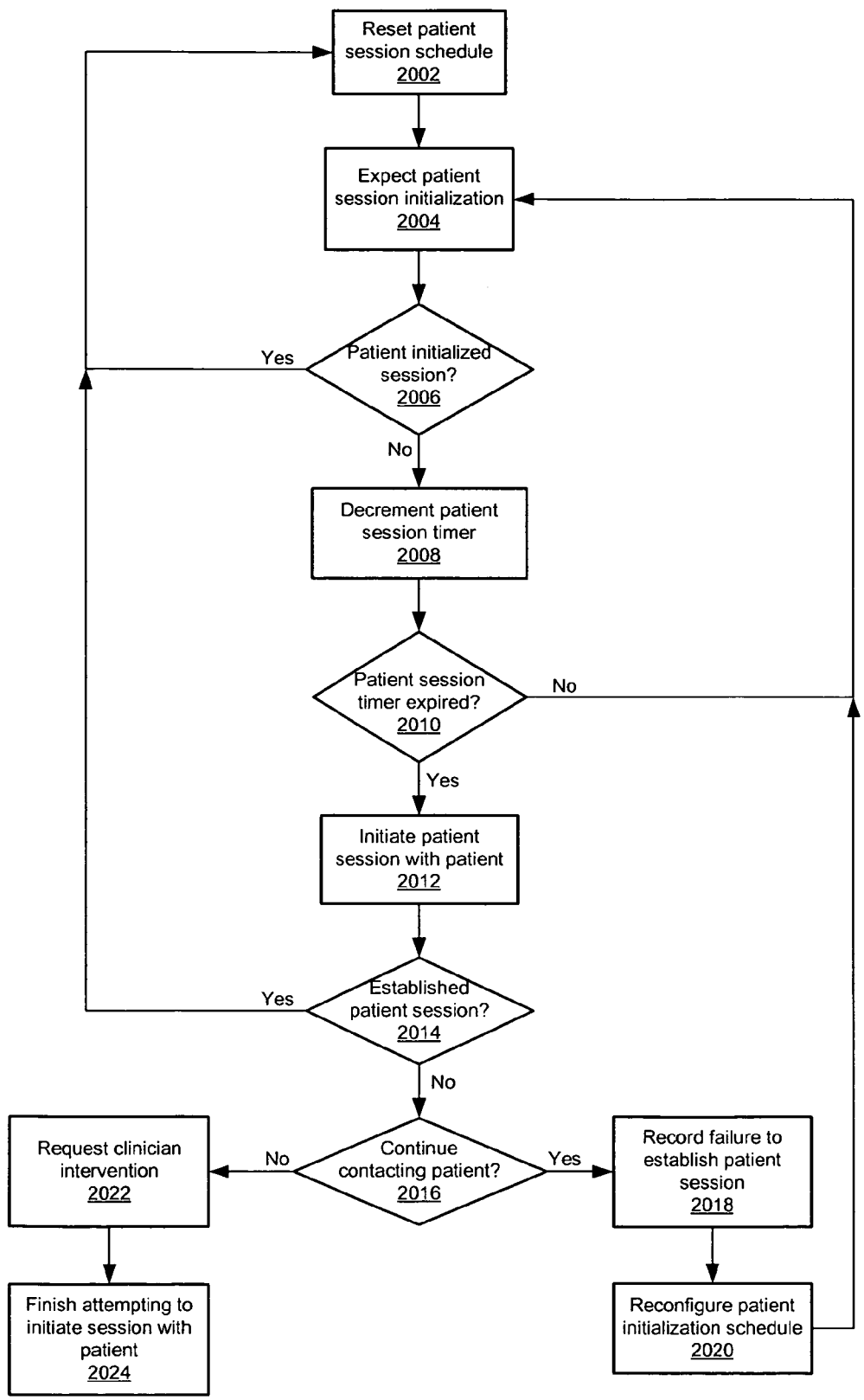
FIG. 20 is a flowchart of one embodiment of contacting a patient when the patient fails to contact the patient monitoring system.

FIG. 20 is a flowchart depicting the operation of contacting a patient when the patient fails to contact the patient monitoring system, according to one embodiment. In one embodiment, a patient associated with the patient monitoring system 2108 has a schedule that the patient is expected to adhere to while the patient is being monitored. For example, the patient may be expected to contact the patient monitoring system 2108 on a weekly basis. Each time the patient contacts the patient monitoring system 2108, the patient monitoring system 2108 resets the patient session schedule (Block 2002). The patient may contact the patient monitoring system 2108 according to schedule, ahead of the schedule, behind schedule, or combinations thereof. Where the patient contacts the patient monitoring system 2108 ahead of schedule, the patient monitoring system 2108 adjusts the patient contact schedule accordingly, such as by moving each subsequent scheduled contact period ahead proportionally.

As an example, suppose that the patient schedule starts on a Monday such that the patient monitoring system 2108 expects the patient to contact the patient monitoring system 2108 every Monday. After the patient monitoring system 2108 has reset the patient session schedule (Block 2002), the patient monitoring system 2108 then waits for the patient to initialize a patient session (Block 2004). In this example, the patient monitoring system 2108 checks whether it is to expect the patient to contact it. If the patient monitoring system 2108 expects the patient to contact it, the patient monitoring system 2108 then determines whether the patient has, in fact, initialized the patient session (Block 2006). If the patient initialized the patient session with the patient monitoring system 2108, the patient monitoring system 2108 then resets the patient schedule (Block 2002).

However, if the patient did not initialize a patient session, the patient monitoring system 2108 then decrements a patient session timer (Block 2008). In one embodiment, the patient session timer is a timer that extends to the patient a grace period before the patient monitoring system contacts the patient. In the example where the patient is expected to contact the patient monitoring system 2108 every Monday, the patient session timer may allow the patient a four-day grace period before contacting the patient. For example, if the patient was expected to contact the patient monitoring system 2108 on a Monday, but failed to contact the patient monitoring system 2108 and the day is now Tuesday, the patient monitoring system 2108 will decrement the patient session timer by one day. The patient session timer may be measured in other time increments such as seconds, minutes, and hours, weeks, months, or even years. Other temporal measurements are also possible.

The patient monitoring system 2108 then determines whether the patient session timer has expired (Block 2010). If the patient session timer has not expired, the system then proceeds to expect as patient session initialization (Block 2004). In the example where the patient is expected to contact the patient monitoring system 2108 every Monday, the patient monitoring system 2108 may wait one day before determining whether the patient initialize a patient session (Block 2006). The patient monitoring system 2108 continues in this manner until the patient monitoring system 2108 determines that the patient session timer has expired. If the patient monitoring system 2108 determines that the patient session timer has expired (Block 2010), the patient monitoring system 2108 then attempt to initiate a patient session with the patient (Block 2012). In the example where the patient is expected to contact the patient monitoring system 2108 every Monday, and there is a missed contact, the patient monitoring system 2108 will attempt to initiate contact with the patient, such as by telephone, the Internet, a mobile communication device, by mail, or other communication medium or device, or combination thereof.

Once the patient monitoring system has attempted to initiate a patient session with the patient (Block 2010), the patient monitoring system 2108 then determines whether it was successful in establishing a patient session (Block 2014). If the patient monitoring system 2108 was successful in establishing a patient session, the patient monitoring system 2108 then resets the patient session schedule (Block 2002). In the example of where the patient is expected to contact the patient monitoring system 2108 every Monday, if the patient monitoring system 2108 establishes the patient session with the patient, the patient monitoring system 2108 will reset the patient schedule such as to expect a patient session the following Monday. If the patient monitoring system 2108 was unsuccessful in establishing a patient session, the patient monitoring system 2108 may continue subsequent attempts to contact the patient. For example, the patient monitoring system 2108 may be preprogrammed to continue contacting a patient once every 24 hours. In another example, the patient record may reflect how often the patient monitoring system 2108 should continue contacting the patient after the patient monitors system 2108 was unsuccessful in establishing a patient session. The patient monitoring system 2108 continues contacting the patient until the patient monitoring system 2108 reaches a contacting limits that has been predefined by the system, by the patient, by the clinician, or combination thereof. When the patient monitoring system 2108 reaches the contacting limit, the patient monitoring system 2108 then determines whether it should continue contacting the patient (Block 2016).

If the patient monitoring system 2108 determines that it should not continue contacting the patient, the patient monitoring system requests clinician intervention (Block 2022). For example, the patient monitoring system 2108 may contact a clinician of associated with the patient record over a communication medium such as telephone, the Internet, a wireless communication device, postal mail, or combination thereof. In another embodiment, the patient monitoring system 2108 is preprogrammed to contact a specific clinician when the patient monitoring system 2108 determines that should not continue contacting the patient. In another embodiment, the patient monitoring system 2108 requests intervention by an entity other than the clinician, such as a health-care provider, or patient caregiver. After the patient monitoring system 2108 has requested clinician intervention (Block 2022), the patient monitoring system 2108 then finishes its attempts to initiate the patient session with the patient (Block 2024). In one embodiment, the patient monitoring system 2108 records the number of times it had attempted to contact the patient. In another embodiment, the patient monitoring system 2108 modifies the patient record to reflect that the patient may no longer be active in the patient monitoring system 2108.

If the patient monitoring system 2108 decides it should continue contacting the patient, the patient monitoring system 2108 records a failure to establish a patient session in the patient's record stored in the patient record database 2116 (Block 2018). The recorded failure may indicate the number of times the patient monitoring system 2108 attempted to contact the patient, the days on which the patient monitoring system 2108 attempted to contact the patient, the conditions under which the patient monitoring system 2108 attempted to contact the patient, or other related information. After recording the failure to establish the patient session, the patient monitoring system 2108 then reconfigures the patient initialization schedule such as to expected the patient to initialize a session more frequently (Block 2020). In another embodiment, the patient monitoring system 2108 reconfigures the patient initialization schedule such as to expect the patient to contact the patient monitoring system 2108 less frequently. In a further embodiment, the patient monitoring system 2108 reconfigures the patient initialization schedule based on a predefined schedule associated with the patient's record stored in the patient record database 2116. Other sources of information for reconfiguring the patient initialization schedule may include the clinician, the patient, a health-care provider, patient monitoring devices, or combination thereof. Alternatively, or in addition to, reconfiguring the patient initialization schedule, the patient monitoring system 2108 initializes a failure prevention mechanism 2128 to contact the patient 2104. Once the patient monitoring system 2108 has established contact with the patient after it has reconfigured the patient initialization schedule (Block 2020), the patient monitoring system 2108 then resets the patient session schedule to the initial schedule that was created for the patient (Block 2002).

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A computer-implemented method for directing behavior of a first patient of a plurality of patients towards behavioral objective, the method comprising:

calculating, with a statistical processor, a first statistical profile of the plurality of patients, the first statistical profile being operative, for an input of the first patient, to produce the most likely output from among a modeled patient-population, based on a comparison of the input of the first patient with the modeled patient-population, to allow the system to determine types of behavior modification treatments that are successful in achieving a particular behavioral goal based at least in part on a statistical distribution indicating a likelihood of a predicted outcome;

calculating, with a patient behavioral path calculator, a first behavioral path to the behavioral objective for the first patient based on an initial state of the first patient and the statistical profile of the plurality of patients;

determining an upper fault limit and a lower fault limit based on the statistical profile of the plurality of patients, each of the upper fault limit and the lower fault limit comprising a variability estimate with respect to the first behavioral path;

selecting, with a patient monitoring processor, a type of targeted message, wherein the type of targeted message includes a positive reinforcement targeted message or a negative reinforcement targeted message;

generating, with the patient monitoring processor, a first targeted message based on the calculated behavioral path and the selected type of targeted message;

establishing a first session;

sending, with an information communication processor, the first targeted message during the first session to motivate the first patient to achieve the behavioral objective and elicit a first response representative of a result thereof;

determining a relationship between the first response and the upper fault limit and the lower fault limit;

triggering, based on the determination of the relationship, an intervention when the upper fault limit or the lower fault limit is crossed;

modifying, with the statistical processor, the statistical profile based on the first response, the modified first statistical profile being further operative, for the first response, to produce the most likely output from among a modeled patient-population, updated based on the first response, to allow the system to redetermine the types of behavior modification treatments that are successful in achieving a particular behavioral goal based at least in part on a statistical distribution indicating a likelihood of the predicted outcome;

re-calculating, prior to the first patient achieving the behavioral objective, with the patient behavioral path calculator, the first behavioral path to the behavioral objective for the first patient based on the modified statistical profile of the plurality of patients;

re-selecting, with the patient monitoring processor, the selected type of targeted message based on the effectiveness of the first targeted message;

generating, with the patient monitoring processor, a second targeted message based on the re-calculated first behavioral path and the re-selected type of targeted message;

establishing a second session;

sending, with the information communication processor, the second targeted message during the second session to motivate the first patient to achieve the behavioral objective and elicit a second response representative of a result thereof, and modifying, with the statistical processor, based on the second response, the modified statistical profile based on the second response.

2. The computer-implemented method of claim 1, further comprising defining, with a patient goal calculator, a first plurality of intermediate behavioral goals along the calculated first behavioral path for achieving the behavioral objective.

3. The computer implemented method of claim 2 further comprising re-defining, with a patient goal calculator, a previously defined first plurality of intermediate behavioral goals using the re-calculated first behavioral path for achieving the behavioral objective, where the previously defined first plurality of intermediate behavioral goals were previously based on the calculated first behavioral path.

4. The computer implemented method of claim 1, further comprising:
calculating, with the patient behavioral path calculator, a second behavioral path to the behavioral objective for a second patient of the plurality of patients based on an initial state of the second patient and the modified statistical profile of the plurality of patients;
determining, with the patient monitoring processor, a targeted message based on the second behavioral path;
establishing a session with the second patient;
sending, with the information communication processor, the targeted message based on the second behavioral path to the second patient during the session with the second patient to motivate the second patient to achieve the behavioral objective of the second behavioral path and elicit a response from the second patient representative of a result thereof; and
modifying, with the statistical processor, the modified statistical profile based on the response from the second patient.

5. The computer implemented method of claim 4, wherein the second patient is more likely to achieve a first intermediate behavioral goal than the first patient.

6. The computer implemented method of claim 1, further comprising:
calculating, with the statistical processor, the statistical profile of the plurality of patients based on provided statistical information.

7. The computer implemented method of claim 1, further comprising:
determining, with a patient goal analyzer, whether a first intermediate behavioral goal has been achieved based on the first response.

8. The computer implemented method of claim 7, further comprising:
intervening, with a failure prevention mechanism, when the first patient fails to achieve the first intermediate behavioral goal.

9. The computer-implemented method of claim 1, further comprising:
determining a trend with respect to the behavioral objective, the determining comprising comparing at least the first response and the second response with the behavioral objective; and
triggering the intervention or another intervention when the trend is away from the behavioral objective.

10. A system for directing behavior of a first patient of a plurality of patients towards a behavioral objective, the system comprising:
a statistical processor operative to calculate a first statistical profile of the plurality of patients, the first statistical profile being operative, for an input of the first patient, to produce the most likely output from among a modeled patient-population, based on a comparison of the input of the first patient with the modeled patient-population, to allow the system to determine types of behavior modification treatments that are successful in achieving a particular behavioral goal based at least in part on a statistical distribution indicating a likelihood of a predicted outcome;
a patient behavioral path calculator operative to calculate a first behavioral path to the behavioral objective for the first patient based on an initial state of the first patient and the first statistical profile of the plurality of patients, wherein the statistical processor is further operative to determine an upper fault limit and a lower fault limit based on the first statistical profile of the plurality of patients, each of the upper fault limit and the lower fault limit comprising a variability estimate with respect to the first behavioral path;
a patient monitoring processor coupled with the patient behavioral path calculator operative to select a type of targeted message, wherein the type of targeted message includes a positive reinforcement targeted message or a negative reinforcement targeted message, wherein the patient monitoring processor is further operative to generate a first targeted message based on the calculated first behavioral path and the selected type of targeted message;
an information communication processor coupled with the patient monitoring processor operative to send the first targeted message during a first session to motivate the first patient to achieve the behavioral objective and to receive a first response representative of a result thereof, wherein the statistical processor is further operative to determine a relationship between the first response and the upper fault limit and the lower fault limit, and to trigger, based on the determination of the relationship, an intervention when the upper fault limit or the lower fault limit is crossed; and
wherein prior to the first patient achieving the behavioral objective,
the statistical processor is further operative to modify the first statistical profile of the plurality of patients, the modified first statistical profile being further operative, for the first response, to produce the most likely output from among a modeled patient-population, updated based on the first response, to allow the system to redetermine the types of behavior modification treatments that are successful in achieving a particular behavioral goal based at least in part on a statistical distribution indicating a likelihood of the predicted outcome;
the patient behavioral path calculator is further operative to recalculate the first behavioral path to the behavioral objective for the first patient based on the modified statistical profile of the plurality of patients;
the patient monitoring processor is further operative to re-select the selected type of targeted message based on the effectiveness of the first targeted message and generate a second targeted message based on the recalculated first behavioral path and the re-selected type of targeted message;
the information communication processor is further operative to send the second targeted message during a second session to motivate the first patient to achieve a first intermediate behavioral goal and to receive a second response representative of a result thereof; and
the statistical processor is further operative to modify the modified statistical profile based on the received second response.

11. The system of claim 10, further comprising a patient goal calculator coupled with the patient behavioral path calculator and operative to calculate a first plurality of intermediate behavioral goals along the first behavioral path for achieving the behavioral objective.

12. The system of claim 11, wherein the patient monitoring processor selects the first targeted message based on a first intermediate behavioral goal of the first plurality of intermediate behavioral goals.

13. The system of claim 11, wherein the patient goal calculator is further operative to recalculate a previously calculated first plurality of intermediate behavioral goals along the recalculated first behavioral path for achieving the behavioral objective, wherein the previously calculated first plurality of intermediate behavioral goals were calculated based on the calculated first behavioral path.

14. The system of claim 10, wherein:
the patient behavioral path calculator is further operative to calculate a second behavioral path to the behavioral objective for a second patient of the plurality of patients based on the modified statistical profile of the plurality of patients;
the patient monitoring processor is further operative to select a targeted message based on the calculated second behavioral path;
the information communication processor is further operative to send the targeted message based on the calculated second behavioral path to the second patient during a session with the second patient to motivate the second patient to achieve the behavioral objective and to receive a response from the second patient representative of a result thereof; and,
the statistical processor is further operative to modify the modified statistical profile based on the received response from the second patient.

15. The system of claim 10, wherein the second patient is more likely to achieve a first intermediate behavioral goal than the first patient.

16. The system of claim 10, wherein the statistical processor is operative to further calculate the statistical profile of the plurality of patients based on provided statistical information.

17. The system of claim 10, further comprising a patient goal analyzer coupled with the patient monitoring processor operative to determine whether a first intermediate behavioral goal has been achieved based on the first response.

18. The system of claim 10, further comprising a failure prevention mechanism coupled with the patient goal analyzer operative to intervene when the first patient fails to achieve a first intermediate behavioral goal.

19. The system of claim 10, wherein the first statistical profile of the plurality of patients further comprises at least one of a mean, a standard deviation, and a percentile associated with the statistical distribution.

20. The system of claim 10, wherein the predicted outcome is based on predictive modeling, the predictive modeling comprising at least one of: generalized linear modeling, generalized mixed effects modeling, generalized estimating equations, time series modeling, tree-structured regression, Bayesian modeling, near neighbor methods, clustering algorithms, scaling algorithms, neural networking, mixed effect modeling, and Markov modeling.

21. A computer implemented method for directing behavior of a first patient of a plurality of patients towards a behavioral objective, the method comprising:
calculating, with a statistical processor, a first statistical profile of the plurality of patients, the first statistical profile being operative, for an input of the first patient, to produce the most likely output from among a modeled patient-population, based on a comparison of the input of the first patient with the modeled patient-population, to allow the system to determine types of behavior modification treatments that are successful in achieving a particular behavioral goal based at least in part on a statistical distribution indicating a likelihood of a predicted outcome;
calculating, with a patient behavioral path calculator, a first behavioral path for the first patient of the plurality of patients based on an initial state of the first patient and a statistical profile of the plurality of patients, wherein the first behavioral path comprises a first individual baseline outcome and a first predicted intervention outcome determined based on the statistical profile of the plurality of patients;
calculating, with the patient behavioral path calculator, a first baseline fault tolerance limit based on a magnitude of difference between the first individual baseline outcome and the first predicted intervention outcome, the first baseline fault tolerance limit comprising a variability estimate;
selecting, with a patient monitoring processor, a type of targeted message, wherein the type of targeted message includes a positive reinforcement targeted message or a negative reinforcement targeted message;
determining, with the patient monitoring processor, a first survey based on the calculated first behavioral path and the selected type of targeted message;
sending, with an information communication processor, the first survey to motivate the first patient to achieve the first predicted intervention outcome and to elicit a first response indicative of a result thereof;
calculating, with a patient goal calculator, a first interval outcome based on the elicited first response;
re-selecting, with the patient monitoring processor, the selected type of targeted message based on the effectiveness of the first targeted message;
generating, prior to the first patient achieving the behavioral objective, with the patient monitoring processor, a second survey based on the calculated first behavioral path, the calculated first interval outcome, and the re-selected type of targeted message;
sending, with the information communication processor, the second survey to motivate the first patient to achieve the first predicted intervention outcome and to elicit a second response indicative of a result thereof;
determining a relationship between the first response and the first baseline fault tolerance limit;
triggering, based on the determination of the relationship, an intervention when the first baseline fault tolerance limit is crossed;
calculating, with the patient goal calculator, a second interval outcome based on the elicited second response; and
calculating, with the patient behavioral path calculator, a second fault tolerance limit based on comparing the first interval outcome and the second interval outcome with the first baseline fault tolerance limit.

22. The computer implemented method of claim 21, further comprising:
determining, with the patient monitoring processor, a third survey for communicating to the first patient based on the calculated first behavioral path and the calculated second fault tolerance limit;
sending, with the information communication processor, the third survey to the first patient to motivate the first patient to achieve the first predicted intervention outcome and to elicit a third response from the first patient indicative of a result thereof; and,
calculating, with the patient goal calculator, a third interval outcome based on the elicited third response.

23. The computer implemented method of claim 22, further comprising:
  comparing, with a patient goal analyzer, the first interval outcome with the calculated first baseline fault tolerance limit; and,
  intervening, with a failure prevention mechanism, when the first interval outcome exceeds the calculated first baseline fault tolerance limit.

24. The computer implemented method of claim 21, further comprising:
  modifying, with the statistical processor, the statistical profile of the plurality of patients based on the first interval outcome of the first patient;
  calculating, with the patient behavioral path calculator, a second behavioral path for a second patient of the plurality of patients based on an initial state of the second patient and the modified statistical profile of the plurality of patients, wherein the second behavioral path comprises a second individual baseline outcome and a second predicted intervention outcome;
  calculating, with the patient behavioral path calculator, a second baseline fault tolerance limit based on a magnitude of difference between the second individual baseline outcome and the second predicted intervention outcome;
  determining, with the patient monitoring processor, a survey for communicating to the second patient based on the calculated second behavioral path;
  sending, with the information communication processor, the survey to the second patient to motivate the second patient to achieve the second predicted intervention outcome and to elicit a response from the second patient indicative of a result thereof; and,
  calculating, with the patient goal calculator, an interval outcome based on the elicited response from the second patient.

25. The computer implemented method of claim 24, further comprising:
  comparing, with a patient goal analyzer, the second interval outcome with the calculated second baseline fault tolerance limit;
  calculating, with the patient behavioral path calculator, a third baseline fault tolerance limit based on the comparison of the interval outcome based on the elicited response from the second patient with the calculated second baseline fault tolerance limit;
  determining, with the patient monitoring processor, a third survey for communicating to the second patient based on the calculated second behavioral path and the calculated third fault tolerance limit;
  sending, with the information communication processor, the third survey to the second patient to motivate the second patient to achieve the second predicted intervention outcome and to elicit a third response from the second patient indicative of a result thereof; and,
  calculating, with the patient goal calculator, a third interval outcome based on the elicited third response.

26. The computer implemented method of claim 21, wherein the first statistical profile of the plurality of patients further comprises at least one of a mean, a standard deviation, and a percentile associated with the statistical distribution.

27. The computer implemented method of claim 21, wherein the predicted outcome is based on predictive modeling, the predictive modeling comprising at least one of: generalized linear modeling, generalized mixed effects modeling, generalized estimating equations, time series modeling, tree-structured regression, Bayesian modeling, near neighbor methods, clustering algorithms, scaling algorithms, neural networking, mixed effect modeling, and Markov modeling.

28. A system for directing behavior of a first patient of a plurality of patients towards a behavioral objective, the method comprising:
  means for calculating a first statistical profile of the plurality of patients, the first statistical profile being operative, for an input of the first patient, to produce the most likely output from among a modeled patient-population, based on a comparison of the input of the first patient with the modeled patient-population, to allow the system to determine types of behavior modification treatments that are successful in achieving a particular behavioral goal based at least in part on a statistical distribution indicating a likelihood of a predicted outcome;
  means for calculating a first behavioral path to the behavioral objective for the first patient based on an initial state of the first patient and the statistical profile of the plurality of patients;
  means for determining an upper fault limit and a lower fault limit based on the statistical profile of the plurality of patients, each of the upper fault limit and the lower fault limit comprising a variability estimate with respect to the first behavioral path;
  means for selecting a type of targeted message, wherein the type of targeted message includes a positive reinforcement targeted message or a negative reinforcement targeted message;
  means for generating a first targeted message based on the calculated behavioral path and the selected type of targeted message;
  means for establishing a first session;
  means for sending the first targeted message during the first session to motivate the first patient to achieve the behavioral objective and elicit a first response representative of a result thereof;
  means for determining a relationship between the first response and the upper fault limit and the lower fault limit;
  means for triggering, based on the determination of the relationship, an intervention when the upper fault limit or the lower fault limit is crossed;
  means for modifying the statistical profile based on the first response, the modified first statistical profile being further operative, for the first response, to produce the most likely output from among a modeled patient-population, updated based on the first response, to allow the system to redetermine the types of behavior modification treatments that are successful in achieving a particular behavioral goal based at least in part on a statistical distribution indicating a likelihood of the predicted outcome;
  means for re-calculating, prior to the first patient achieving the behavioral objective, the first behavioral path to the behavioral objective for the first patient based on the modified statistical profile of the plurality of patients;
  means for re-selecting the selected type of targeted message based on the effectiveness of the first targeted message;
  means for generating a second targeted message based on the re-calculated first behavioral path and the re-selected type of targeted message;
  means for establishing a second session;
  means for sending the second targeted message during the second session to motivate the first patient to achieve the behavioral objective and elicit a second response representative of a result thereof; and means for modifying, based on the second response, the modified statistical profile.

29. The system of claim 28, further comprising means for defining a first plurality of intermediate behavioral goals along the calculated first behavioral path for achieving the behavioral objective.

30. The system of claim 28, further comprising:
means for calculating a second behavioral path to the behavioral objective for a second patient of the plurality of patients based on an initial state of the second patient and the modified statistical profile of the plurality of patients;
means for determining a targeted message based on the second behavioral path;
means for establishing a second session with the second patient;
means for sending the targeted message based on the second behavioral path to the second patient during the second session to motivate the second patient to achieve the behavioral objective of the second behavioral path and elicit a response from the second patient representative of a result thereof, and means for modifying, based on the response from the second patient, the modified statistical profile.

31. The system of claim 30, wherein the second patient is more likely to achieve a first intermediate behavioral goal than the first patient.

32. The system of claim 28, further comprising:
means for calculating the statistical profile of the plurality of patients based on provided statistical information.

33. The system of claim 28, further comprising:
means for determining whether a first intermediate behavioral goal has been achieved based on the first response.

34. The system of claim 33, further comprising:
means for intervening when the first patient fails to achieve the first intermediate behavioral goal.

* * * * *